US012203091B2

(12) United States Patent
Chae

(10) Patent No.: US 12,203,091 B2
(45) Date of Patent: Jan. 21, 2025

(54) ENGINEERED PESTICIDAL PROTEINS AND METHODS OF CONTROLLING PLANT PESTS

(71) Applicant: Syngenta Participations AG, Basel (CH)

(72) Inventor: Hyunsook S. Chae, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 85 days.

(21) Appl. No.: 18/059,112

(22) Filed: Nov. 28, 2022

(65) Prior Publication Data
US 2023/0203529 A1 Jun. 29, 2023

Related U.S. Application Data

(62) Division of application No. 16/468,528, filed as application No. PCT/US2017/063722 on Nov. 29, 2017, now Pat. No. 11,535,862.

(60) Provisional application No. 62/432,909, filed on Dec. 12, 2016.

(51) Int. Cl.

| | |
|---|---|
| *C12N 15/82* | (2006.01) |
| *A01N 37/46* | (2006.01) |
| *A01N 63/50* | (2020.01) |
| *C07K 14/325* | (2006.01) |

(52) U.S. Cl.
CPC ......... *C12N 15/8286* (2013.01); *A01N 37/46* (2013.01); *A01N 63/50* (2020.01); *C07K 14/325* (2013.01)

(58) Field of Classification Search
CPC .................................................. C12N 15/8286
USPC .......................................................... 800/302
See application file for complete search history.

(56) References Cited

U.S. PATENT DOCUMENTS

| | | | |
|---|---|---|---|
| 6,780,408 B1 | 8/2004 | Bosch et al. | |
| 7,799,971 B2 | 9/2010 | Frank et al. | |
| 8,735,560 B1 | 5/2014 | English et al. | |
| 9,441,240 B2 * | 9/2016 | Burns | C12N 15/8218 |
| 11,535,862 B2 * | 12/2022 | Chae | C07K 14/325 |
| 2010/0017914 A1 | 1/2010 | Hart et al. | |
| 2011/0203015 A1 | 8/2011 | Sampson | |
| 2015/0148288 A1 | 5/2015 | Kennedy et al. | |

FOREIGN PATENT DOCUMENTS

| | | |
|---|---|---|
| JP | H06192295 A | 7/1994 |
| RU | 2007102339 | 6/2005 |
| WO | 9928477 A1 | 6/1999 |
| WO | 2003082910 A1 | 10/2003 |
| WO | 2011075587 A1 | 6/2011 |
| WO | 2011084631 A1 | 7/2011 |
| WO | 2011103248 A2 | 8/2011 |
| WO | 2016061197 A1 | 4/2016 |
| WO | 2016061377 A2 | 4/2016 |
| WO | 2016061391 A2 | 4/2016 |
| WO | 2017003811 A1 | 1/2017 |

OTHER PUBLICATIONS

International Search Report cited in Internation Application No. PCT/US2017/063722 filed Nov. 29, 2019 mailed on Feb. 16, 2018.
Deist, Benjamin et al.: "Bt Toxin Modification for Enhanced Efficacy", Toxins, vol. 6, No. 10, Oct. 22, 1994, pp. 3005-3027, XP055278078, DOI: 10.3390/toxins6103005.
Extended ESR for EP17880405.0, mailed on Oct. 1, 2020.
Pesticidal protein, partial [Bacillus thuringiensis], NCBI Reference Sequence: WP_033698688.1, Nov. 26, 2014.
GenBank Accession No. WP_033698688.1, 2014.

* cited by examiner

*Primary Examiner* — Li Zheng
(74) *Attorney, Agent, or Firm* — Katherine Seguin

(57) ABSTRACT

The invention provides nucleic acids, polypeptides, transgenic plants, compositions and methods for conferring pesticidal activity (e.g., insecticidal activity) to bacteria, plants, plant cells, tissues and seeds. Nucleic acids encoding the insecticidal proteins can be used to transform prokaryotic and eukaryotic organisms to express the insecticidal proteins. The recombinant organisms or compositions containing the recombinant organisms or insecticidal proteins or in combination with an appropriate agricultural carrier can be used to control an insect pest in various environments.

18 Claims, 8 Drawing Sheets

Specification includes a Sequence Listing.

```
BT-0029     1  --MEINNQN--------Q--CVPYNCLNNPESEILNVAIFS----------SEQVAEIHLKITRLILENFLPGGSFAFGLFDLIWGIFNEDQWSAF
BT-0022     1  --MKSKNQN--MHQSLSNNATVDKNFTGSLENNTNTELQNFNHEG---IEPFVSVSTIQTGIGIAGKILGNLGVPFAGQVASLYSFILGELWPKGKSQWEIF
Cry1Fa      1  --MENNIQN--------Q--CVPYNCLNNPEVEILNEERST---------GRLPLDISLSLTRFLLSEFVPGVGVAFGLFDLIWGFITPSDWSLF
Cry1Ka      1  MNSNRKNENEIINALSIPAVSNHSAQMDLSPDARIEDSLCVAEGNNIDPFVSASTVQTGISIAGRILGVLGVPFAGQLASFYSFLVGELWPSGRDPWEIF

BT-0029    75  LRQVEELIN-QRITEFARGQAIQRLVGFGRSYDEYILALKEWENDPDNPASKERVRTRFRTTDDALLTGVPLMAIPGFELATLSVYAQSANLHLALLRDA
BT-0022    96  MEHVEELIN-QKISTYARNKALADLKGLGDALAVYHESLESWIKNRNNTRTRSVVKSQYITLELMFVQSLPSFAVSGEEVPLLPIYAQAANLHLLLLRDA
Cry1Fa     75  LLQIEQLIE-QRIETLERNRAITTLRGLADSYEIYIEALREWEANPNNAQLREDVRIRFANTDDALITAINNFTLTSFEIPLLSVYVQAANLHLSLLRDA
Cry1Ka    101  MEHVEQIVRQQITDSVRDTAIARLEGLGRGYRSYQQALETWLDNRNDARSRSIIREYIALELDITTAIPLFSIRNEEVPLLMVYAQAANLHLLLLRDA

BT-0029   174  VFFGERWGLTQTNINDLYSRLKNSIRDYTNHCVRFYNIGLGNLNVIRP----EYYRFQRELTISVLDLVALFPNYDIRTYPIPTKSQLTREIYTDPIISP
BT-0022   195  SIFGKEWGLSDSEISTFYNRQVERTSDYSDHCTKWFDTGLNRLKGSNAEIWVKYNQFRRDMTLMVLDLVALFQSYDTHMYPIKTTAQLTREVYTNAIGTV
Cry1Fa    174  VSFGQWGLDIATVNNHYNRLINLIHRYTKHCLDTYNQGLENLRGTNTRQWARFNQFRRDLITLTVLDIVALFPNYDVRTYPIQTSSQLTREIYTSSVIED
Cry1Ka    201  SLFGSEWGMSSADVNQYYQEQIRYTEEYSNHCVQWYNTGLNRLRGTTAETWVRYNQFRRDLTIGVLDLVALFPSYDTRTYPIPTTAQLTREVYTDPNGVV

BT-0029   270  GAQAG-----------YTLQDVLREPHLMDFLNRLIIYTGEYRGIRHWAGHEVESSRTGMMTNIRFPLYGTAATAEPTRFITPSTFPGLNLFYRTL
BT-0022   295  HPHPSFTSTTWYNNAPSFSAIEAAVIRSPHLLDFLEQVTIYSLLSRWSNTQYMNMWGG-HKLEFRTIGG-TLNTSTQGSTNTSINPVTLPFTSRDIYRT
Cry1Fa    274  SPVSAN------IPNGFNRAEFGVRPPHLMDFMNSLFVTAETVRSQTVWGGHLVSS-RNTAGNRINFPSYGVFNPGAIWIADEDRP---FYRTL
Cry1Ka    301  AGP-----NNSWFRNGASFSAIENAIIRQPHLYDFLTNLTIYTRRS-QVGTTIMNLWAG-HRITFNRIQGGSTSEMVYGAITNPVSVSDIPFVNRDVYRT

BT-0029   355  SAPIFRDEPGANIIIRYRTSLVEGVGFIQPNNGEQLYRVGTLDSLDQLPLEGES--SLTEYSHRLCHVRFAQSLRNAEPLDYARVPM[SWTHRSATPTN]
BT-0022   393  ESLAGLNLFLTQPVNGVPRVDFHWKFVTHP-IASDNFYYPGYAGIGTQLQDSENELPETTGQPNYESYSHRLSHIGLISASHVKALV[SWTHRSADRTN]
Cry1Fa    360  SDPVFVRGGFGNPHYVLGLRGVAFQQTG--TNHTRTFRNSGTIDSLDEIPPQDNSGAPWNDYSHVLNHVTFVRWPGEISGSDSWRAPM[SWTHRSATPTN]
Cry1Ka    394  VSLAGGLGLSLSGIRYGLTRVDFDMIFRNHPDIVTGLFYHPGHAGIATQVKDSDTELPPETTEQPNYRAFSHLLSHISMGPTTQDVPPV[SWTHQSADRTN]
                                                                                                ↑
                                                                                               CB3

Domain III
BT-0029   453  TIDPDVITQIPLVKAFNLHSGATIVKGPGFT[GGDILRRTNVGSFGDMRVNITAPLSQRYRVRIRYASTTDLQFYTNINGTTINIGNFSSTMDSGDDLQYG
BT-0022   492  TIHSDSITQIPLVKAHTLQSGTTVVKGPGFT[GGDILRRTSGGPFAFSNVNLDWNLSQRYRARIRYASTTNLRMYVTIAGERIFAGQFNKTMNTGDPLTFQ
Cry1Fa    458  TIDPERITQIPLVKAHTLQSGTTVVRGPGFT[GGDILRRTSGGPFAYTIVNINGQLPQRYRARIRYASTTNLRIYVTVAGERIFAGQFNKTMDTGDPLTFQ
Cry1Ka    494  TINSDRITQIPLVKAHTLQSGTTVVKGPGFT[GGDILRRTSGGPFAFSNVNLDFNLSQRYRARIRYASTTNLRIYVTVAGERIFAGQFDKTMDAGAPLTFQ
                                              Domain III BT-0029   553  RFRVAGFTTPFTFSDAMSTFTIGAFSFSSNNEVYIDRIEFVPAEVTFEAEYDLEKAQKAVNALFTSSNQIGLKTDVT-DYHIDKVSNLIVECLSDEFCLDE
BT-0022   592  SFSYATIDTAFTFPTKASSLTVGADTFSSGNEVYVDRFELIPVTATLEAVTDLERAQKAVHELFTSNPGGLKTDVAKDHYTNTISKSVQSVFRCRCSER
Cry1Fa    558  SFSYATINTAFTFPMSQSSFTVGADTFSSGNEVYIDRFELIPVTATFEAEYDLERAQKAVNALFTSINQIGIKTDVT-DYHIDQVSNLVDCLSDEFCLDE
Cry1Ka    594  SFSYATINTAFTFPERSSSLTIGADTFSSGNEVYVDRFELIQVTATFEAESDLERARKAVNALFTSNPRGLKTDVT-DYHIDQVSNLVECLSDEFCLDK
```

Fig. 1A

```
BT-0029   652  KRELSEKVKHAKRLCDERNLLQDPNFRGINRQPDRGWRGSTDITIQGDDVFKENYVTLPGTFDECYPTYLYQKIDESKLKAYTRYELRGYIEDSQDLEI
BT-0022   692  TR------IYRWGYPSKKEYWIWGYTSKY---------------------------------------------------------------------
Cry1Fa    657  KRELSEKVKHAKRLSDERNLLQDPNFKGINRQLDRGWRGSTDITIQRGDDVFKENYVTLPGTFDECYPTYLYQKIDESKLKPYTRYQLRGYIEDSQDLEI
Cry1Ka    693  KRELLEEVKYAKRLSDERNLLQDPTFTSISGQTDRGWIGSTGISIQGGDDIFKENYVRLPGTVDECYPTYLYQKIDESQLKSYTRYQLRGYIEDSQDLEI

BT-0029   752  YLIRYNAKHETVNVPGTGSLMPLSAQSPIGKCGEPNRCATHLEWNPDLDCSCRDGEKCAHHSHHFSLDIDVGCTDLNEDLGWVIFKIKTQGHARLGNL
BT-0022   716  -------------------------------------------------------------------------------------------------
Cry1Fa    757  YLIRYNAKHETVNLGTGSLMPLSVQSPIRKCGEPNRCAPHLEWNPDLDCSCRDGEKCAHHSHHFSLDIDVGCTDLNEDLDVWIFKIKTQGHARLGNL
Cry1Ka    793  YLIRYNAKHETLSVPGTESPWPSSGVYPSGRCGEPNRCAPRIEWNPDLDCSCRYGEKCVHHSHHFSLDIDVGCTDLNEDLGWVIFKIKTQDGHAKLGNL

BT-0029   852  EFLEEKPLVGEALARVKRAEKKWRDKREKLELETNIVYKEAKKSVDALFVNSQYDRLQADTNIAIIHAADKRVHSIREAYLPELSVIPGVNAAIFEELEG
BT-0022   716  -------------------------------------------------------------------------------------------------
Cry1Fa    857  EFLEEKPLVGEALARVKRAEKKWRDKREKLELETNIVYKEAKESVDALFVNSQYDQLQADTNIAMIHAADKRVHRIREAYLPELSVIPGVNVDIFEELKG
Cry1Ka    893  EFIEEKPLLGKALSRVKRAEKKWRDKRDKYEKLQLETKRVYTEAKESVDALFVDSQYDKLQANTNIGIIHGADKQVHRIREPYLSELPVIPSINAAIFEELEG

BT-0029   952  RIFTAYSLYDARNVIKNGDFNNGLSCWNVKGHVDVEEQNNHRSVLVVPEWEAEVSQEVRVCPGRGYILRVTAYKEGYGEGCVTIHEIEDNTDELKFSNCV
BT-0022   716  -------------------------------------------------------------------------------------------------
Cry1Fa    957  RIFTAFFLYDARNVIKNGDFNNGLSCWNVKGHVDVEEQNNHRSVLVVPEWEAEVSQEVRVCPGRGYILRVTAYKEGYGEGCVTIHEIENNTDELKFSNCV
Cry1Ka    993  HIFKAYSLYDARNVIKNGDFNNGLSCWNVKGHVDVQQN--HHRSVLVLSEWEAEVSQKVRVCPDRGYILRVTAYKEGYGEGCVTIHEFEDNTDVLKFRNFV

BT-0029  1052  EEEIYPNNTVTCNDYTATQEEYEGTYTSRNR------GYDGAYESNSSVPADYASASAYEEKAYTDGRRDNTCESNRGYDYTPLPAGYVTKELEYFPETDK
BT-0022   710  -------------------------------------------------------------------------------------------------
Cry1Fa   1057  EEEVYPNNTVTCNDYTANQEEYGGAYTSRNR------GYDETYGSNSSVPADYASVYEEKSYTDGRRDNPCESNRGYGDYTPLPAGYVTKELEYFPETDK
Cry1Ka   1092  EEEVYPNNTVTCNDYTTNQSAEGSTDACNSYNRGYEDGYENRYEPNPSAPVNYTPTYEEGMYTDTQGYNHCVSDRGYRNHTPLPAGYVTLELEYFPETEQ

BT-0029  1146  VWIEIGETEGTFIVDSVELLLMEE
BT-0022   716  -----------------------
Cry1Fa   1151  VWIEIGETEGTFIVDSVELLLMEE
Cry1Ka   1192  VWIEIGETEGTFIVGSVELLLMEE
```

Fig.1B

```
BT-0029      1  MEINNQNQCVPYNCLNNPESEILNVAIFSSEQVAEIHLKITRLILENFLPGGSFAFGLFDLIWGIFNEDQWSAFLRQVEELINQRITEFARGQAIQRLVG
BT29-BT22    1  MEINNQNQCVPYNCLNNPESEILNVAIFSSEQVAEIHLKITRLILENFLPGGSFAFGLFDLIWGIFNEDQWSAFLRQVEELINQRITEFARGQAIQRLVG
BT29-1Fa     1  MEINNQNQCVPYNCLNNPESEILNVAIFSSEQVAEIHLKITRLILENFLPGGSFAFGLFDLIWGIFNEDQWSAFLRQVEELINQRITEFARGQAIQRLVG
BT29-1Ka     1  MEINNQNQCVPYNCLNNPESEILNVAIFSSEQVAEIHLKITRLILENFLPGGSFAFGLFDLIWGIFNEDQWSAFLRQVEELINQRITEFARGQAIQRLVG

BT-0029    101  FGRSYDEYILALKEWENDPDNPASKERVRTRFRTTDDALLTGVPLMAIPGFELATLSVYAQSANLHLALLRDAVFFGERWGLTQTNINDLYSRLKNSIRD
BT29-BT22  101  FGRSYDEYILALKEWENDPDNPASKERVRTRFRTTDDALLTGVPLMAIPGFELATLSVYAQSANLHLALLRDAVFFGERWGLTQTNINDLYSRLKNSIRD
BT29-1Fa   101  FGRSYDEYILALKEWENDPDNPASKERVRTRFRTTDDALLTGVPLMAIPGFELATLSVYAQSANLHLALLRDAVFFGERWGLTQTNINDLYSRLKNSIRD
BT29-1Ka   101  FGRSYDEYILALKEWENDPDNPASKERVRTRFRTTDDALLTGVPLMAIPGFELATLSVYAQSANLHLALLRDAVFFGERWGLTQTNINDLYSRLKNSIRD

BT-0029    201  YTNHCVRFYNIGLGNLNVIRPEYYRFQRELTISVLDLVALFPNYDIRTYPIPTKSQLTREIYTDPIISPGAQAGYTLQDVLREPHLMDFLNRLIIYTGEY
BT29-BT22  201  YTNHCVRFYNIGLGNLNVIRPEYYRFQRELTISVLDLVALFPNYDIRTYPIPTKSQLTREIYTDPIISPGAQAGYTLQDVLREPHLMDFLNRLIIYTGEY
BT29-1Fa   201  YTNHCVRFYNIGLGNLNVIRPEYYRFQRELTISVLDLVALFPNYDIRTYPIPTKSQLTREIYTDPIISPGAQAGYTLQDVLREPHLMDFLNRLIIYTGEY
BT29-1Ka   201  YTNHCVRFYNIGLGNLNVIRPEYYRFQRELTISVLDLVALFPNYDIRTYPIPTKSQLTREIYTDPIISPGAQAGYTLQDVLREPHLMDFLNRLIIYTGEY

BT-0029    301  RGIRHWAGHEVESSRTGMMTNIRFPLYGTAATAEPTRFITPSTFPGLNLFYRTLSAPIFRDEPGANIIIRYRTSLVEGVGFIQPNNGEQLYRVRGTLDSL
BT29-BT22  301  RGIRHWAGHEVESSRTGMMTNIRFPLYGTAATAEPTRFITPSTFPGLNLFYRTLSAPIFRDEPGANIIIRYRTSLVEGVGFIQPNNGEQLYRVRGTLDSL
BT29-1Fa   301  RGIRHWAGHEVESSRTGMMTNIRFPLYGTAATAEPTRFITPSTFPGLNLFYRTLSAPIFRDEPGANIIIRYRTSLVEGVGFIQPNNGEQLYRVRGTLDSL
BT29-1Ka   301  RGIRHWAGHEVESSRTGMMTNIRFPLYGTAATAEPTRFITPSTFPGLNLFYRTLSAPIFRDEPGANIIIRYRTSLVEGVGFIQPNNGEQLYRVRGTLDSL

┌─────────── Domain III ───────────
BT-0029    401  DQLPLEGESSLTEYSHRLCHVRFAQSLRNAEPLDYARVPMSWTHRSATPTNTIDPDVITQIPLVKAFNLHSGATIVKGPGFTGGDILRRTIVGSFGDMR
BT29-BT22  401  DQLPLEGESSLTEYSHRLCHVRFAQSLRNAEPLDYARVPMSWTHRSATPTNTIDPDVITQIPLVKAHTLQSGTTVVKGPGFTGGDILRRTSGGPFAFSN
BT29-1Fa   401  DQLPLEGESSLTEYSHRLCHVRFAQSLRNAEPLDYARVPMSWTHRSATPTNTIDPDVITQIPLVKAHTLQSGTTVVRGPGFTGGDILRRTSGGPFAYTI
BT29-1Ka   401  DQLPLEGESSLTEYSHRLCHVRFAQSLRNAEPLDYARVPMSWTHRSATPTNTIDPDVITQIPLVKAHTLQSGTTVVKGPGFTGGDILRRTSGGPFAFSN
                                                        └────────── CB3 ──────────┘
                └──── Domain III ─────

BT-0029    501  VNITAPLSQRYRIRYASTTDLQFYTNINGTTNINGNFSSTMDSGDDLQYGRFRVAGFTTPFTFSDAMSTFTIGAFSFSSNNEVYIDRIEFVPAEVTFE
BT29-BT22  501  VNLDWNLSQRYRARIRYASTTNLRMVVTIAGERIFAGQFNKTMNTGDPLTFQSFSYATIDTAFTFPTKASSLTVGADTFSSGNEVYIDRFELIPVTATFE
BT29-1Fa   501  VNINGQLPQRYRARIRYASTTNLRIYVTVAGERIFAGQFNKTMDTGDPLTFQSFSYATINTAFTFPMSQSSFTVGADTFSSGNEVYIDRFELIPVTATFE
BT29-1Ka   501  VNLDFNLSQRYRARIRYASTTNLRIYVTVAGERIFAGQFNKTMDAGAPLTFQSFSYATINTAFTFPERSSSLTIGADTFSSGNEVYVDRFELIQVTATFE

BT-0029    601  AEYDLEKAQKAVNALFTSSNQIGLKTDVTDYHIDKVSNLVECLSDEFCLDEKRELSEKVKHAKRLCDERNLLQDPNFRGINRQPDRGWRGSTDITIQGGD
BT29-BT22  601  AEYDLEKAQKAVNALFTSSNQIGLKTDVTDYHIDKVSNLVECLSDEFCLDEKRELSEKVKHAKRLCDERNLLQDPNFRGINRQPDRGWRGSTDITIQGGD
BT29-1Fa   601  AEYDLEKAQKAVNALFTSSNQIGLKTDVTDYHIDKVSNLVECLSDEFCLDEKRELSEKVKHAKRLCDERNLLQDPNFRGINRQPDRGWRGSTDITIQGGD
BT29-1Ka   601  AEYDLEKAQKAVNALFTSSNQIGLKTDVTDYHIDKVSNLVECLSDEFCLDEKRELSEKVKHAKRLCDERNLLQDPNFRGINRQPDRGWRGSTDITIQGGD
```

Fig.2A

```
BT-0029    701  DVFKENYVTLPGTFDECYPTYLYQKIDESKLKAYTRYELRGYIEDSQDLEIYLIRYNAKHETVNVPGTGSLWPLSAQSPIGKCGEPNRCATHLEWNPDLD
BT29-BT22  701  DVFKENYVTLPGTFDECYPTYLYQKIDESKLKAYTRYELRGYIEDSQDLEIYLIRYNAKHETVNVPGTGSLWPLSAQSPIGKCGEPNRCATHLEWNPDLD
BT29-1Fa   701  DVFKENYVTLPGTFDECYPTYLYQKIDESKLKAYTRYELRGYIEDSQDLEIYLIRYNAKHETVNVPGTGSLWPLSAQSPIGKCGEPNRCATHLEWNPDLD
BT29-1Ka   701  DVFKENYVTLPGTFDECYPTYLYQKIDESKLKAYTRYELRGYIEDSQDLEIYLIRYNAKHETVNVPGTGSLWPLSAQSPIGKCGEPNRCATHLEWNPDLD

BT-0029    801  CSCRDGEKCAHHSHHFSLDIDVGCTDLNEDLGVWVIFKIKTQDGHARLGNLEFLEEKPLVGEALARVKRAEKKWRDKREKLELETNIVYKEAKKSVDALF
BT29-BT22  801  CSCRDGEKCAHHSHHFSLDIDVGCTDLNEDLGVWVIFKIKTQDGHARLGNLEFLEEKPLVGEALARVKRAEKKWRDKREKLELETNIVYKEAKKSVDALF
BT29-1Fa   801  CSCRDGEKCAHHSHHFSLDIDVGCTDLNEDLGVWVIFKIKTQDGHARLGNLEFLEEKPLVGEALARVKRAEKKWRDKREKLELETNIVYKEAKKSVDALF
BT29-1Ka   801  CSCRDGEKCAHHSHHFSLDIDVGCTDLNEDLGVWVIFKIKTQDGHARLGNLEFLEEKPLVGEALARVKRAEKKWRDKREKLELETNIVYKEAKKSVDALF

BT-0029    901  VNSQYDRLQADTNIAIIHAADKRVHSIREAYLPELSVIPGVNAAIFEELEGRIFTAYSLYDARNVIKNGDFNNGLSCWNVKGHVDVEEQNNHRSVLVVPE
BT29-BT22  901  VNSQYDRLQADTNIAIIHAADKRVHSIREAYLPELSVIPGVNAAIFEELEGRIFTAYSLYDARNVIKNGDFNNGLSCWNVKGHVDVEEQNNHRSVLVVPE
BT29-1Fa   901  VNSQYDRLQADTNIAIIHAADKRVHSIREAYLPELSVIPGVNAAIFEELEGRIFTAYSLYDARNVIKNGDFNNGLSCWNVKGHVDVEEQNNHRSVLVVPE
BT29-1Ka   901  VNSQYDRLQADTNIAIIHAADKRVHSIREAYLPELSVIPGVNAAIFEELEGRIFTAYSLYDARNVIKNGDFNNGLSCWNVKGHVDVEEQNNHRSVLVVPE

BT-0029   1001  WEAEVSQEVRVCPGRGYILRVTAYKEGYGEGCVTIHEIEDNTDELKFSNCVEEEIYPNNTVTCNDYTATQEEYEGTYTSRNRGYDGAYESNSSVPADYAS
BT29-BT22 1001  WEAEVSQEVRVCPGRGYILRVTAYKEGYGEGCVTIHEIEDNTDELKFSNCVEEEIYPNNTVTCNDYTATQEEYEGTYTSRNRGYDGAYESNSSVPADYAS
BT29-1Fa  1001  WEAEVSQEVRVCPGRGYILRVTAYKEGYGEGCVTIHEIEDNTDELKFSNCVEEEIYPNNTVTCNDYTATQEEYEGTYTSRNRGYDGAYESNSSVPADYAS
BT29-1Ka  1001  WEAEVSQEVRVCPGRGYILRVTAYKEGYGEGCVTIHEIEDNTDELKFSNCVEEEIYPNNTVTCNDYTATQEEYEGTYTSRNRGYDGAYESNSSVPADYAS

BT-0029   1101  AYEEKAYTDGRRDNTCESNRGYGDYTPLPAGYVTKELEYFPETDKVWIEIGETEGTFIVDSVELLLMEE
BT29-BT22 1101  AYEEKAYTDGRRDNTCESNRGYGDYTPLPAGYVTKELEYFPETDKVWIEIGETEGTFIVDSVELLLMEE
BT29-1Fa  1101  AYEEKAYTDGRRDNTCESNRGYGDYTPLPAGYVTKELEYFPETDKVWIEIGETEGTFIVDSVELLLMEE
BT29-1Ka  1101  AYEEKAYTDGRRDNTCESNRGYGDYTPLPAGYVTKELEYFPETDKVWIEIGETEGTFIVDSVELLLMEE
```

Fig. 2B

```
Bt29-Bt22
SEQ ID NO:3     1  MEINNQNQCVPYNCLNNPESEILNVAIFSSEQVAEIHLKITRLILENFLPGGSFAFGLFDLIWGIFNEDQWSAFLRQVEE
SEQ ID NO:20    1  MEINNQNQCVPYNCLNNPESEILNVAIFSSEQVAEIHLKITRLILENFLPGGSFAFGLFDLIWGIFNEDQWSAFLRQVEE
SEQ ID NO:21    1  MEINNQNQCVPYNCLNNPESEILNVAIFSSEQVAEIHLKITRLILENFLPGGSFAFGLFDLIWGIFNEDQWSAFLRQVEE
SEQ ID NO:22    1  MEINNQNQCVPYNCLNNPESEILNVAIFSSEQVAEIHLKITRLILENFLPGGSFAFGLFDLIWGIFNEDQWSAFLRQVEE
SEQ ID NO:23    1  MEINNQNQCVPYNCLNNPESEILNVAIFSSEQVAEIHLKITRLILENFLPGGSFAFGLFDLIWGIFNEDQWSAFLRQVEE
SEQ ID NO:24    1  MEINNQNQCVPYNCLNNPESEILNVAIFSSEQVAEIHLKITRLILENFLPGGSFAFGLFDLIWGIFNEDQWSAFLRQVEE
SEQ ID NO:25    1  MEINNQNQCVPYNCLNNPESEILNVAIFSSEQVAEIHLKITRLILENFLPGGSFAFGLFDLIWGIFNEDQWSAFLRQVEE

Bt29-Bt22
SEQ ID NO:3    81  LINQRITEFARGQAIQRLVGFGRSYDEYILALKEWENDPDNPASKERVRTRFRTTDDALLTGVPLMAIPGFELATLSVYA
SEQ ID NO:20   81  LINQRITEFARGQAIQRLVGFGRSYDEYILALKEWENDPDNPASKERVRTRFRTTDDALLTGVPLMAIPGFELATLSVYA
SEQ ID NO:21   81  LINQRITEFARGQAIQRLVGFGRSYDEYILALKEWENDPDNPASKERVRTRFRTTDDALLTGVPLMAIPGFELATLSVYA
SEQ ID NO:22   81  LINQRITEFARGQAIQRLVGFGRSYDEYILALKEWENDPDNPASKERVRTRFRTTDDALLTGVPLMAIPGFELATLSVYA
SEQ ID NO:23   81  LINQRITEFARGQAIQRLVGFGRSYDEYILALKEWENDPDNPASKERVRTRFRTTDDALLTGVPLMAIPGFELATLSVYA
SEQ ID NO:24   81  LINQRITEFARGQAIQRLVGFGRSYDEYILALKEWENDPDNPASKERVRTRFRTTDDALLTGVPLMAIPGFELATLSVYA
SEQ ID NO:25   81  LINQRITEFARGQAIQRLVGFGRSYDEYILALKEWENDPDNPASKERVRTRFRTTDDALLTGVPLMAIPGFELATLSVYA

SEQ ID NO:3   161  QSANLHLALLRDAVFFGERWGLTQTNINDLYSRLKNSIRDYTNHCVRFYNIGLGNLNVIRPEYYRFQRELTISVLDLVAL
SEQ ID NO:20  161  QSANLHLALLRDAVFFGERWGLTQTNINDLYSRLKNSIRDYTNHCVRFYNIGLGNLNVIRPEYYRFQRELTISVLDLVAL
SEQ ID NO:21  161  QSANLHLALLRDAVFFGERWGLTQTNINDLYSRLKNSIRDYTNHCVRFYNIGLGNLNVIRPEYYRFQRELTISVLDLVAL
SEQ ID NO:22  161  QSANLHLALLRDAVFFGERWGLTQTNINDLYSRLKNSIRDYTNHCVRFYNIGLGNLNVIRPEYYRFQRELTISVLDLVAL
SEQ ID NO:23  161  QSANLHLALLRDAVFFGERWGLTQTNINDLYSRLKNSIRDYTNHCVRFYNIGLGNLNVIRPEYYRFQRELTISVLDLVAL
SEQ ID NO:24  161  QSANLHLALLRDAVFFGERWGLTQTNINDLYSRLKNSIRDYTNHCVRFYNIGLGNLNVIRPEYYRFQRELTISVLDLVAL
SEQ ID NO:25  161  QSANLHLALLRDAVFFGERWGLTQTNINDLYSRLKNSIRDYTNHCVRFYNIGLGNLNVIRPEYYRFQRELTISVLDLVAL

SEQ ID NO:3   241  FPNYDIRTYPIPTKSQLTREIYTDPIISPGAQAGYTLQDVLREPHLMDFLNRLIIYTGEYRGIRHWAGHEVESSRTGMMT
SEQ ID NO:20  241  FPNYDIRTYPIPTKSQLTREIYTDPIISPGAQAGYTLQDVLREPHLMDFLNRLIIYTGEYRGIRHWAGHEVESSRTGMMT
SEQ ID NO:21  241  FPNYDIRTYPIPTKSQLTREIYTDPIISPGAQAGYTLQDVLREPHLMDFLNRLIIYTGEYRGIRHWAGHEVESSRTGMMT
SEQ ID NO:22  241  FPNYDIRTYPIPTKSQLTREIYTDPIISPGAQAGYTLQDVLREPHLMDFLNRLIIYTGEYRGIRHWAGHEVESSRTGMMT
SEQ ID NO:23  241  FPNYDIRTYPIPTKSQLTREIYTDPIISPGAQAGYTLQDVLREPHLMDFLNRLIIYTGEYRGIRHWAGHEVESSRTGMMT
SEQ ID NO:24  241  FPNYDIRTYPIPTKSQLTREIYTDPIISPGAQAGYTLQDVLREPHLMDFLNRLIIYTGEYRGIRHWAGHEVESSRTGMMT
SEQ ID NO:25  241  FPNYDIRTYPIPTKSQLTREIYTDPIISPGAQAGYTLQDVLREPHLMDFLNRLIIYTGEYRGIRHWAGHEVESSRTGMMT
```

Fig. 3A

| | | |
|---|---|---|
| SEQ ID NO:3 | 321 | NIRFPLYGTAATAEPTRFITPSTFPGLNLFYRTLSAPIFRDEPGANIIIRYRTSLVEGVGFIQPNNGEQLYRVRGTLDSL |
| SEQ ID NO:20 | 321 | NIRFPLYGTAATAEPTRFITPSTFPGLNLFYRTLSAPIFRDEPGANIIIRYRTSLVEGVGFIQPNNGEQLYRVRGTLDSL |
| SEQ ID NO:21 | 321 | NIRFPLYGTAATAEPTRFITPSTFPGLNLFYRTLSAPIFRDEPGANIIIRYRTSLVEGVGFIQPNNGEQLYRVRGTLDSL |
| SEQ ID NO:22 | 321 | NIRFPLYGTAATAEPTRFITPSTFPGLNLFYRTLSAPIFRDEPGANIIIRYRTSLVEGVGFIQPNNGEQLYRVRGTLDSL |
| SEQ ID NO:23 | 321 | NIRFPLYGTAATAEPTRFITPSTFPGLNLFYRTLSAPIFRDEPGANIIIRYRTSLVEGVGFIQPNNGEQLYRVRGTLDSL |
| SEQ ID NO:24 | 321 | NIRFPLYGTAATAEPTRFITPSTFPGLNLFYRTLSAPIFRDEPGANIIIRYRTSLVEGVGFIQPNNGEQLYRVRGTLDSL |
| SEQ ID NO:25 | 321 | NIRFPLYGTAATAEPTRFITPSTFPGLNLFYRTLSAPIFRDEPGANIIIRYRTSLVEGVGFIQPNNGEQLYRVRGTLDSL |
| SEQ ID NO:3 | 401 | DQLPLEGESSLTEYSHRLCHVRFAQSLRNAEPLDYARVPMFSWTHRSATPTNTIDPDVITQIPLVKAHTLQSGTTVVKGP |
| SEQ ID NO:20 | 401 | DQLPLEGESSLTEYSHRLCHVRFAQSLRNAEPLDYARVPMFSWTHRSATPTNTIDPDVITQIPLVKAHTLQSGTTVVKGP |
| SEQ ID NO:21 | 401 | DQLPLEGESSLTEYSHRLCHVRFAQSLRNAEPLDYARVPMFSWTHRSATPTNTIDPDVITQIPLVKAHTLQSGTTVVKGP |
| SEQ ID NO:22 | 401 | DQLPLEGESSLTEYSHRLCHVRFAQSLRNAEPLDYARVPMFSWTHRSATPTNTIDPDVITQIPLVKAHTLQSGTTVVKGP |
| SEQ ID NO:23 | 401 | DQLPLEGESSLTEYSHRLCHVRFAQSLRNAEPLDYARVPMFSWTHRSATPTNTIDPDVITQIPLVKAHTLQSGTTVVKGP |
| SEQ ID NO:24 | 401 | DQLPLEGESSLTEYSHRLCHVRFAQSLRNAEPLDYARVPMFSWTHRSATPTNTIDPDVITQIPLVKAHTLQSGTTVVKGP |
| SEQ ID NO:25 | 401 | DQLPLEGESSLTEYSHRLCHVRFAQSLRNAEPLDYARVPMFSWTHRSATPTNTIDPDVITQIPLVKAHTLQSGTTVVKGP |
| SEQ ID NO:3 | 481 | GFTGGDILRRTSGGPFAFSNVNLDWNLSQRYRARIRYASTTNLRMYVTIAGERIFAGQFNKTMNTGDPLTFQSFSYATID |
| SEQ ID NO:20 | 481 | GFTGGDILRRTSGGPFAFSNVNLDWNLSQRYRARIRYASTTNLRMYVTIAGERIFAGQFNKTMNTGDPLTFQSFSYATID |
| SEQ ID NO:21 | 481 | GFTGGDILRRTSGGPFAFSNVNLDWNLSQRYRARIRYASTTNLRMYVTIAGERIFAGQFNKTMNTGDPLTFQSFSYATID |
| SEQ ID NO:22 | 481 | GFTGGDILRRTSGGPFAFSNVNLDWNLSQRYRARIRYASTTNLRMYVTIAGERIFAGQFNKTMNTGDPLTFQSFSYATID |
| SEQ ID NO:23 | 481 | GFTGGDILRRTSGGPFAFSNVNLDWNLSQRYRARIRYASTTNLRMYVTIAGERIFAGQFNKTMNTGDPLTFQSFSYATID |
| SEQ ID NO:24 | 481 | GFTGGDILRRTSGGPFAFSNVNLDWNLSQRYRARIRYASTTNLRMYVTIAGERIFAGQFNKTMNTGDPLTFQSFSYATID |
| SEQ ID NO:25 | 481 | GFTGGDILRRTSGGPFAFSNVNLDWNLSQRYRARIRYASTTNLRMYVTIAGERIFAGQFNKTMNTGDPLTFQSFSYATID |
| SEQ ID NO:3 | 561 | TAFTFPTKASSLTVGADTFSSGNEVYVDRFELIPVTATFEAEYDLEKAQKAVNALFTSSNQIGLKTDVTDYHIDKVSNLV |
| SEQ ID NO:20 | 561 | TAFTFPTKASSLTVGADTFSSGNEVYVDRFELIPVTATFEAEYDLEKAQKAVNALFTSSNQIGLKTDVTDYHIDKVSNLV |
| SEQ ID NO:21 | 561 | TAFTFPTKASSLTVGADTFSSGNEVYVDRFELIPVTATFEAEYDLEKAQKAVNALFTSSNQIGLKTDVTDYHIDKV---- |
| SEQ ID NO:22 | 561 | TAFTFPTKASSLTVGADTFSSGNEVYVDRFELIPVTATFEAEYDLEKAQKAVNALFTSSNQI----------------- |
| SEQ ID NO:23 | 561 | TAFTFPTKASSLTVGADTFSSGNEVYVDRFELIPVTATFEAEYDLEKAQKAVNALFTSSNQ------------------ |
| SEQ ID NO:24 | 561 | TAFTFPTKASSLTVGADTFSSGNEVYVDRFELIPVTATFEAEYDLEKAQK----------------------------- |
| SEQ ID NO:25 | 561 | TAFTFPTKASSLTVGADTFSSGNEVYVDRFELIPVTATFEAEY-------------------------------------- |

Fig. 3B

```
SEQ ID NO:3    641 ECLSDEFCLDEKRELSEKVKHAKRLCDERNLLQDPNFRGINRQPDRGWRGSTDITIQGGDDVFKENYVTLPGTFDECYPT
SEQ ID NO:20   641 ECLSDEFCLDEK-----------------------------------------------------------------
SEQ ID NO:21   637 -----------------------------------------------------------------------------
SEQ ID NO:22   623 -----------------------------------------------------------------------------
SEQ ID NO:23   611 -----------------------------------------------------------------------------
SEQ ID NO:24   608 -----------------------------------------------------------------------------
SEQ ID NO:25   604 -----------------------------------------------------------------------------

SEQ ID NO:3    721 YLYQKIDESKLKAYTRYELRGYIEDSQDLEIYLIRYNAKHETVNVPGTGSLWPLSAQSPIGKCGEPNRCATHLEWNPDLD
SEQ ID NO:20   653 -----------------------------------------------------------------------------
SEQ ID NO:21   637 -----------------------------------------------------------------------------
SEQ ID NO:22   623 -----------------------------------------------------------------------------
SEQ ID NO:23   611 -----------------------------------------------------------------------------
SEQ ID NO:24   608 -----------------------------------------------------------------------------
SEQ ID NO:25   604 -----------------------------------------------------------------------------

SEQ ID NO:3    801 CSCRDGEKCAHHSHHFSLDIDVGCTDLNEDLGVWVIFKIKTQDGHARLGNLEFLEEKPLVGEALARVKRAEKKWRDKREK
SEQ ID NO:20   653 -----------------------------------------------------------------------------
SEQ ID NO:21   637 -----------------------------------------------------------------------------
SEQ ID NO:22   623 -----------------------------------------------------------------------------
SEQ ID NO:23   611 -----------------------------------------------------------------------------
SEQ ID NO:24   608 -----------------------------------------------------------------------------
SEQ ID NO:25   604 -----------------------------------------------------------------------------

SEQ ID NO:3    881 LELETNIVYKEAKKSVDALFVNSQYDRLQADTNIAIIHAADKRVHSIREAYLPELSVIPGVNAAIFEELEGRIFTAYSLY
SEQ ID NO:20   653 -----------------------------------------------------------------------------
SEQ ID NO:21   637 -----------------------------------------------------------------------------
SEQ ID NO:22   623 -----------------------------------------------------------------------------
SEQ ID NO:23   611 -----------------------------------------------------------------------------
SEQ ID NO:24   608 -----------------------------------------------------------------------------
SEQ ID NO:25   604 -----------------------------------------------------------------------------
```

Fig. 3C

```
Bt29-Bt22    961  DARNVIKNGDFNNGLSCWNVKGHVDVEEQNNHRSVLVVPEWEAEVSQEVRVCPGRGYILRVTAYKEGYGEGCVTIHEIED
SEQ ID NO:20 653  --------------------------------------------------------------------------------
SEQ ID NO:21 637  --------------------------------------------------------------------------------
SEQ ID NO:22 623  --------------------------------------------------------------------------------
SEQ ID NO:23 611  --------------------------------------------------------------------------------
SEQ ID NO:24 608  --------------------------------------------------------------------------------
SEQ ID NO:25 604  --------------------------------------------------------------------------------

Bt29-Bt22   1041  NTDELKFSNCVEEEIYPNNTVTCNDYTATQEEYEGTYTSRNRGYDGAYESNSSVPADYASAYEEKAYTDGRRDNTCESNR
SEQ ID NO:20 653  --------------------------------------------------------------------------------
SEQ ID NO:21 637  --------------------------------------------------------------------------------
SEQ ID NO:22 623  --------------------------------------------------------------------------------
SEQ ID NO:23 611  --------------------------------------------------------------------------------
SEQ ID NO:24 608  --------------------------------------------------------------------------------
SEQ ID NO:25 604  --------------------------------------------------------------------------------

Bt29-Bt22   1121  GYGDYTPLPAGYVTKELEYFPETDKVWIEIGETEGTFIVDSVELLMEE
SEQ ID NO:20 653

ENGINEERED PESTICIDAL PROTEINS AND METHODS OF CONTROLLING PLANT PESTS

RELATED APPLICATION INFORMATION

This application is a divisional of granted U.S. Pat. No. 11,535,862, filed Jun. 11, 2019, which is a national stage application of International Application No. PCT/US2017/063722, filed Nov. 29, 2017, which claims priority to U.S. Provisional Application No. 62/432,909, filed Dec. 12, 2016, the contents of all of which are incorporated herein by reference herein.

STATEMENT REGARDING ELECTRONIC SUBMISSION OF A SEQUENCE LISTING

A Sequence Listing in xml format, submitted under 37 C.F.R. § 1.821, entitled 81090-US-REG-D-P-1_sequence listing.xml, 96.0 kilobytes in size, generated on Nov. 16, 2022 and filed via EFS-Web is provided in lieu of a paper copy. This Sequence Listing is hereby incorporated by reference into the specification for its disclosures.

FIELD OF THE INVENTION

This invention relates to engineered pesticidal proteins and the nucleic acid molecules that encode them, as well as compositions and methods for controlling plant pests.

BACKGROUND

*Bacillus thuringiensis* (Bt) is a gram-positive spore forming soil bacterium characterized by its ability to produce crystalline inclusions that are specifically toxic to certain orders and species of plant pests, including insects, but are harmless to plants and other non-target organisms. For this reason, compositions comprising *Bacillus thuringiensis* strains or their insecticidal proteins can be used as environmentally-acceptable insecticides to control agricultural insect pests or insect vectors of a variety of human or animal diseases.

Crystal (Cry) proteins from *Bacillus thuringiensis* have potent insecticidal activity against predominantly lepidopteran, dipteran, and coleopteran pest insects. These proteins also have shown activity against pests in the Orders Hymenoptera, Homoptera, Phthiraptera, Mallophaga, and Acari pest orders, as well as other invertebrate orders such as Nemathelminthes, Platyhelminthes, and Sarcomastigorphora (Feitelson, J. 1993. The *Bacillus Thuringiensis* family tree. In Advanced Engineered Pesticides. Marcel Dekker, Inc., New York, N.Y.). These proteins were originally classified as CryI to CryVI based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as CryIA, CryIB, CryIC, etc. Even more closely related proteins within each division were given names such as CryIC(a), CryIC(b), etc.

The terms "Cry toxin" and "delta-endotoxin" have been used interchangeably with the term "Cry protein." Current nomenclature for Cry proteins and genes is based upon amino acid sequence homology rather than insect target specificity (Crickmore et al. (1998) Microbiol. Mol. Biol. Rev. 62:807-813). In this more accepted classification, each toxin is assigned a unique name incorporating a primary rank (an Arabic number), a secondary rank (an uppercase letter), a tertiary rank (a lowercase letter), and a quaternary rank (another Arabic number). In the current classification, Roman numerals have been exchanged for Arabic numerals in the primary rank. For example, "CryIA(a)" under the older nomenclature is now "Cry1Aa" under the current nomenclature. According to Ibrahim et al. (2010, Bioeng. Bugs, 1:31-50), the Cry toxins can still be separated into six major classes according to their insect host specificities and include: Group 1—lepidopteran (e.g., Cry1, Cry9 and Cry15); group 2—lepidopteran and dipteran (e.g., Cry2); group 3—coleopteran (Cry3, Cry7 and Cry8); group 4—dipteran (Cry4, Cry10, Cry11, Cry16, Cry17, Cry19 and Cry20); group 5—lepidopteran and coleopteran (Cry1I); and group 6—nematodes (Cry6). The Cry1I, Cry2, Cry3, Cry10 and Cry11 toxins (73-82 kDa) are unique because they appear to be natural truncations of the larger Cry1 and Cry4 proteins (130-140 kDa).

Cry proteins are globular protein molecules which accumulate as protoxins in crystalline form during the sporulation stage of Bt. After ingestion by a pest, the crystals are typically solubilized to release protoxins, which can range in size, for example, from 130-140 kDa for many of the lepidopteran-active Cry proteins, such as Cry1 and Cry9, and 60-80 kDa for the coleopteran-active Cry3 proteins and the lepidopteran/dipteran-active Cry2 proteins. After the crystals are solubilized by a susceptible insect the released protoxins are processed by proteases in the insect gut, for example trypsin and chymotrypsin, to produce a protease-resistant core Cry protein toxin. This proteolytic processing involves the removal of amino acids from different regions of the various Cry protoxins. For example, Cry protoxins that are 130-140 kDa are typically activated through the proteolytic removal of an N-terminal peptide of 25-30 amino acids and approximately half of the remaining protein from the C-terminus resulting in an approximately 60-70 kDa mature Cry toxin. The protoxins that are 60-80 kDa, e.g. Cry2 and Cry3, are also processed but not to the same extent as the larger protoxins. The smaller protoxins typically have equal or more amino acids removed from the N-terminus than the larger protoxins but less amino acids removed from the C-terminus. For example, proteolytic activation of Cry2 family members typically involves the removal of approximately 40-50 N-terminal amino acids. Many of the Cry proteins are quite toxic to specific target insects, but many have narrow spectrums of activity.

The toxin portions of Cry proteins generally have five conserved sequence blocks, and three conserved structural domains (see, for example, de Maagd et al. (2001) Trends Genetics 17:193-199). The first conserved structural domain, called Domain I, typically consists of seven alpha helices and is involved in membrane insertion and pore formation. Domain II typically consists of three beta-sheets arranged in a Greek key configuration, and domain Ill typically consists of two antiparallel beta-sheets in 'jelly-roll' formation (de Maagd et al., 2001, supra). Domains II and III are involved in receptor recognition and binding, and are therefore considered determinants of toxin specificity.

The five conserved sequence blocks are numbered CB1 to CB5 from N-terminus to C-terminus of the Cry protein (Hofte & Whitely, 1989, Microbiol. Rev. 53:242-255). Conserved block 1 (CB1) comprises approximately 29 amino acids, conserved block 2 (CB2) comprises approximately 67 amino acids, conserved block 3 (CB3) comprises approximately 48 amino acids, conserved block 4 (CB4) comprises approximately 10 amino acids and conserved block 5 (CB5)

comprises approximately 12 amino acids. The sequences before and after these five conserved blocks are highly variable and thus are designated the "variable regions," V1-V6. Domain I of a Bt delta-endotoxin typically comprises variable region 1, conserved block 1, variable region 2, and the N-terminal 52 amino acids of conserved block 2. Domain II typically comprises approximately the C-terminal 15 amino acids of conserved block 2, variable region 3, and approximately the N-terminal 10 amino acids of conserved block 3. Domain III typically comprises approximately the C-terminal 38 amino acids of conserved block 3, variable region 4, conserved block 4, variable region 5, and conserved block 5. The Cry1 lepidopteran active toxins, among other delta-endotoxins, have a variable region 6 with approximately 1-3 amino acids lying within domain Ill.

Numerous commercially valuable plants, including common agricultural crops, are susceptible to attack by plant pests including insect and nematode pests, causing substantial reductions in crop yield and quality. For example, plant pests are a major factor in the loss of the world's important agricultural crops. About $8 billion are lost every year in the United States alone due to infestations of invertebrate pests including insects. Insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Biological pest control agents, such as *Bacillus thuringiensis* strains expressing pesticidal toxins such as Cry proteins, have also been applied to crop plants with satisfactory results, offering an alternative or complement to chemical pesticides. The genes coding for some of these Cry proteins have been isolated and their expression in heterologous hosts such as transgenic plants have been shown to provide another tool for the control of economically important insect pests.

Good insect control can thus be reached, but the continued use of certain chemical and biological control methods heightens the chance for insect pests to develop resistance to such control measures. This has been partially alleviated by various resistance management practices, but there remains a need to develop new and effective pest control agents. Particularly needed are control agents that can target to a wider spectrum of economically important insect pests and/ or that efficiently control insect strains that are or could become resistant to existing insect control agents.

SUMMARY

The invention provides nucleic acids, polypeptides, compositions and methods for conferring pesticidal activity (e.g., insecticidal activity) to bacteria, plants, plant cells, tissues and seeds. In particular, the invention provides novel chimeric pesticidal proteins (e.g., chimeric insecticidal proteins), optionally with altered or enhanced activity as compared with the parent molecule.

In embodiments, the chimeric proteins of the invention are toxic to economically important insect pests (e.g., by inhibiting the ability of the insect pest to survive, grow and/or reproduce), particularly insect pests that infest plants. For example, in embodiments, the chimeric insecticidal proteins of the invention can be used to control one or more economically important lepidopteran pests including without limitation black cutworm (*Agrotis ipsilon*), European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*), rice leaffolder (*Cnaphalocrocis medinalis*), and the like. In embodiments, the chimeric insecticidal protein has activity against a fall armyworm insect pest that is resistant to a Vip3A protein and/or a Cry1F protein.

Accordingly, as one aspect, the invention provides a chimeric insecticidal protein that is toxic to a lepidopteran insect pest comprising in an N-terminal to C-terminal direction: (a) an N-terminal region of a first Cry1 protein, which is optionally an N-terminal region of a BT-0029 protein of SEQ ID NO:2 or an amino acid sequence that is substantially identical thereto, fused to (b) a C-terminal region of a different Cry1 protein; wherein a crossover position between the first Cry1 protein and the different Cry1 protein is located in conserved block 3. In representative embodiments, the different Cry1 protein is a Cry1F (e.g., a Cry1Fa), a Cry1G, a Cry1I (e.g., a Cry1Ia or a Cry1If, such as BT-0022), a Cry1C (e.g. a Cry1Ca) or a Cry1K protein.

In embodiments, the chimeric insecticidal protein according to the invention has insecticidal activity against a *Spodoptera frugiperda* insect pest or an insect pest population with resistance to a Vip3A protein and/or a Cry1F protein.

As a further aspect, the invention provides a nucleotide sequence encoding the chimeric insecticidal proteins of the invention, and expression cassettes and vectors comprising the same. In embodiments, the polynucleotide is codon optimized for expression in a plant (e.g., a monocot plant such as maize or a dicot plant such as soybean).

As a further aspect, the invention provides a transgenic cell (e.g., a transgenic plant cell such as a dicot cell or monocot cell, or a transgenic bacterial cell), transgenic plant part, transgenic plant culture, and transgenic plant seed that comprises a nucleotide sequence, expression cassette, vector and/or chimeric insecticidal protein of the invention.

As still a further aspect, the invention encompasses transgenic plants comprising a plant cell, plant part, nucleotide sequence, expression cassette, vector and/or chimeric insecticidal protein of the invention.

As a further aspect are seeds that produce the transgenic plants of the invention and seeds produced by the transgenic plants of the invention.

Also provided are harvested products derived from the transgenic plants of the invention, wherein the harvested product optionally comprises a nucleotide sequence, expression cassette, vector and/or chimeric insecticidal protein of the invention. Further provided are processed products derived from the harvested products of the invention, wherein the harvested product optionally comprises a nucleotide sequence, expression cassette, vector and/or chimeric insecticidal protein of the invention. In embodiments, the harvested product or processed product comprises an chimeric insecticidal protein of the invention and has increased resistance to an insect pest (e.g., a lepidopteran insect pest).

As still a further aspect, the invention provides an insecticidal composition comprising a chimeric insecticidal protein of the invention and an agriculturally acceptable carrier.

Still further, the invention provides as an additional aspect a method of producing a transgenic plant with increased resistance to an insect pest (e.g., a lepidopteran insect pest).

In embodiments, the method comprises introducing into a plant a polynucleotide, expression cassette, or vector of the invention, wherein the chimeric insecticidal protein is expressed in the plant, thereby producing a transgenic plant with increased resistance to an insect pest. Optionally, the introducing step comprises: (i) transforming a plant cell with the polynucleotide, expression cassette or vector and regenerating a transgenic plant; or (ii) crossing a first plant comprising the polynucleotide, expression cassette or vector with a second plant. In embodiments, the method further comprises producing a seed from the transgenic plant. In embodiments, the method further comprises obtaining a progeny plant from the transgenic plant, wherein the progeny plant comprises the polynucleotide, the expression cassette or the vector, expresses the chimeric insecticidal protein and has increased resistance to an insect pest.

As yet another aspect, the invention provides a method of producing a transgenic plant with increased resistance to an insect pest (e.g., a lepidopteran insect pest), the method comprising: (a) planting a seed comprising a polynucleotide, expression cassette or vector of the invention; and (b) growing a transgenic plant from the seed, wherein the transgenic plant comprises the polynucleotide, expression cassette or vector and produces the chimeric insecticidal protein and has increased resistance to an insect pest. In embodiments, the method further comprises: (c) harvesting a seed from the transgenic plant of (b), wherein the harvested seed comprises the polynucleotide, expression cassette, vector and/or the chimeric insecticidal protein. Optionally, the seed has increased resistance against an insect pest (e.g., a lepidopteran insect pest).

Still further, as another aspect, the invention provides a method of producing a seed. In embodiments, the method comprises: (a) providing a transgenic plant that comprises a polynucleotide, expression cassette or vector of the invention; and (b) harvesting a seed from the transgenic plant of (a), wherein the harvested seed comprises the polynucleotide, expression cassette or vector and/or a chimeric insecticidal protein of the invention. Optionally, the seed has increased resistance against an insect pest (e.g., a lepidopteran insect pest).

The invention further contemplates a method of producing a hybrid plant seed. In representative embodiments, the method comprises: (a) crossing a first inbred plant, which is a transgenic plant comprising a polynucleotide, expression cassette or vector of the invention with a different inbred plant, which may or may not comprise a polynucleotide, expression cassette or vector of the invention; and (b) allowing a hybrid seed to form. In embodiments, the hybrid seed comprises a polynucleotide, expression cassette or vector and/or a chimeric insecticidal protein of the invention. Optionally, the seed has increased resistance against an insect pest (e.g., a lepidopteran insect pest).

As another aspect, the invention provides a method of controlling an insect pest (e.g., a lepidopteran insect pest, such as fall armyworm), the method comprising delivering to the insect pest or an environment thereof a composition comprising an effective amount of a chimeric insecticidal protein or insecticidal composition of the invention. In embodiments, the method is a method of controlling a lepidopteran insect pest (e.g., fall armyworm) that is resistant to a Vip3A protein and/or a Cry1F protein.

Accordingly, as another aspect, the invention provides methods of reducing the development of resistance to a Vip3A protein and/or a Cry1F protein in a population of a target lepidopteran insect pest (e.g., fall armyworm). In embodiments, the method comprises delivering to the target population or an environment thereof a transgenic plant comprising: (i) a polynucleotide, expression cassette, or vector according to the invention; and (ii) a polynucleotide comprising a nucleotide sequence encoding a Vip3A protein and/or a nucleotide sequence encoding a Cry1F protein; wherein the chimeric insecticidal protein and the Vip3A protein and/or the Cry1F protein are produced in the transgenic plant.

The invention is also drawn to methods of using the polynucleotides of the invention, for example, in DNA constructs or expression cassettes or vectors for transformation and expression in organisms, including plants and microorganisms, such as bacteria. The nucleotide or amino acid sequences may be native or synthetic sequences that have been designed for expression in an organism such as a plant or bacteria. The invention is further drawn to methods of making the insecticidal proteins of the invention and to methods of using the polynucleotide sequences and insecticidal proteins, for example in microorganisms to control insects or in transgenic plants to confer protection from insect damage.

Another aspect of the invention includes insecticidal compositions and formulations comprising the chimeric insecticidal proteins of the invention, and methods of using the compositions or formulations to control insect populations, for example by applying the compositions or formulations to insect-infested areas, or to prophylactically treat insect-susceptible areas or plants to confer protection against the insect pests. Optionally, the compositions or formulations of the invention may, in addition to the chimeric insecticidal protein of the invention, comprise other pesticidal agents such as chemical pesticides, other pesticidal proteins, or dsRNA, e.g., in order to augment or enhance the insect-controlling capability of the composition or formulation and/or for insect resistance management.

The compositions and methods of the invention are useful for controlling insect pests that attack plants, particularly crop plants. The compositions of the invention are also useful for detecting the presence of a chimeric insecticidal protein or a nucleic acid encoding the same in commercial products or transgenic organisms.

The invention also provides for uses of the chimeric insecticidal proteins, nucleic acids, transgenic plants, plant parts, seed and insecticidal compositions of the invention, for example, to control an insect pest, such as a lepidopteran pest.

In embodiments, the invention provides a method of using a polynucleotide, expression cassette, vector or host cell of the invention to produce an insecticidal composition for controlling an insect pest (e.g., a lepidopteran insect pest).

In embodiments, the invention provides a method of using a polynucleotide, expression cassette or vector of the invention to produce a transgenic seed, where the transgenic seed grows a transgenic plant with increased resistance to an insect pest.

As another aspect, the invention also contemplates the use of a transgenic plant of the invention to produce a transgenic seed, which is optionally a hybrid seed.

In embodiments, the invention provides a method of using a chimeric insecticidal protein, polynucleotide, expression cassette, vector, transgenic plant or insecticidal composition of the invention to prevent the development of resistance in a population of a target lepidopteran insect pest to a Vip3A protein and/or Cry1F protein.

These and other features, aspects, and advantages of the invention will become better understood with reference to the following detailed description and claims.

BRIEF DESCRIPTION OF THE DRAWINGS

FIGS. 1A and 1B show an alignment of the amino acid sequences of full-length BT-0029 (SEQ ID NO: 2), BT-0022 (SEQ ID NO: 1), Cry1Fa (SEQ ID NO: 8) and Cry1Ka (SEQ ID NO: 12). The Domain III core and Conserved Block 3 (CB3) are indicated. Identical amino acids in the aligned sequences are shaded.

FIGS. 2A and 2B show an alignment of the amino acid sequences of full-length BT-0029 (SEQ ID NO: 2) with exemplary BT-0029 chimeras: Bt29-Bt22 (SEQ ID NO: 3), Bt29-1Fa (SEQ ID NO: 9), and Bt29-1Ka (SEQ ID NO: 13). The Domain III core and Conserved Block 3 (CB3) are indicated. The Domain III core indicated in the figure is derived from the second Cry protein. Identical amino acids in the aligned sequences are shaded.

FIGS. 3A, 3B, 3C and 3D show a full-length Bt29-Bt22 chimera (SEQ ID NO:3) aligned with a series of Bt29-Bt22 chimeras, Bt29-Bt22Tr1 (SEQ ID NO:20), Bt29-Bt22Tr2 (SEQ ID NO:21), Bt29-Bt22Tr3 (SEQ ID NO:22), Bt29-Bt22Tr4 (SEQ ID NO:23), Bt29-Bt22Tr5 (SEQ ID NO:24) and Bt29-Bt22Tr6 (SEQ ID NO:25), with C-terminal truncations within the BT-0029 protoxin tail.

BRIEF DESCRIPTION OF THE SEQUENCES IN THE SEQUENCE LISTING

SEQ ID NO: 1 is the amino acid sequence of a BT-0022 protein.

SEQ ID NO: 2 is the amino acid sequence of a BT-0029 protein.

SEQ ID NO: 3 is the amino acid sequence of a Bt29-Bt22 chimera. The BT-0022 sequence is amino acid 459-597.

SEQ ID NO: 4 is a nucleotide sequence encoding the Bt29-Bt22 chimera of SEQ ID NO: 3.

SEQ ID NO: 5 is an exemplary maize-optimized sequence encoding the Bt29-Bt22 chimera of SEQ ID NO: 3.

SEQ ID NO: 6 is an exemplary maize-optimized sequence encoding the Bt29-Bt22 chimera of SEQ ID NO: 3.

SEQ ID NO: 7 is an exemplary maize-optimized sequence encoding the Bt29-Bt22 chimera of SEQ ID NO: 3.

SEQ ID NO: 8 is the amino acid sequence of a full-length Cry1Fa.

SEQ ID NO: 9 is the amino acid sequence of a Bt29-1Fa chimera. The Cry1Fa sequence is amino acids 459-597.

SEQ ID NO: 10 is a nucleotide sequence encoding the Bt29-1Fa chimera of SEQ ID NO: 9.

SEQ ID NO: 11 is an exemplary maize-optimized sequence encoding the Bt29-1Fa chimera of SEQ ID NO: 9.

SEQ ID NO: 12 is the amino acid sequence of a full-length Cry1Ka.

SEQ ID NO: 13 is the amino acid sequence of a Bt29-1Ka chimera. The Cry1Ka sequence is amino acids 459-597.

SEQ ID NO: 14 is a nucleotide sequence encoding the Bt29-1Ka chimera of SEQ ID NO: 13.

SEQ ID NO: 15 is the amino acid sequence of a Bt29-1Kav2 chimera.

SEQ ID NO: 16 is the nucleotide sequence encoding the Bt29-1Ka chimera of SEQ ID NO: 15.

SEQ ID NO: 17 is the amino acid sequence of a full-length Cry1Ca.

SEQ ID NO: 18 is the amino acid sequence of a Bt29-1Ca chimera. The Cry1Ca sequence is amino acids 459-597.

SEQ ID NO: 19 is a nucleotide sequence encoding the Bt29-1Ca chimera of SEQ ID NO: 18.

SEQ ID NO: 20 is the amino acid sequence of Bt29-Bt22Tr1 protein.

SEQ ID NO: 21 is the amino acid sequence of Bt29-Bt22Tr2 protein.

SEQ ID NO: 22 is the amino acid sequence of Bt29-Bt22Tr3 protein.

SEQ ID NO: 23 is the amino acid sequence of Bt29-Bt22Tr4 protein.

SEQ ID NO: 24 is the amino acid sequence of Bt29-Bt22Tr5 protein.

SEQ ID NO: 25 is the amino acid sequence of Bt29-Bt22Tr6 protein.

SEQ ID NO: 26 is the amino acid sequence of BT29BT22-TL22v1 protein.

SEQ ID NO: 27 is the amino acid sequence of BT29BT22-TL22v2 protein.

SEQ ID NO: 28 is the amino acid sequence of BT29BT22-TL22v3 protein.

SEQ ID NO: 29 is the amino acid sequence of BT29BT22-TL22v4 protein.

SEQ ID NO: 30 is the amino acid sequence of BT29BT22-TL22v5 protein.

SEQ ID NO: 31 is the amino acid sequence of BT29BT22-TL22v6 protein.

SEQ ID NO: 32 is the amino acid sequence of BT291FaTr1 protein.

SEQ ID NO: 33 is the amino acid sequence of BT291FaTr2 protein.

SEQ ID NO: 34 is the amino acid sequence of BT291FaTr3 protein.

SEQ ID NO: 35 is the amino acid sequence of BT291FaTr4 protein.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount. As used herein, phrases such as "between about X and Y" mean "between about X and about Y" and phrases such as "from about X to Y" mean "from about X to about Y."

As used herein, phrases such as "from X to Y" should be interpreted to include X and Y, unless the context indicates otherwise.

By "activity" of an insecticidal protein of the invention is meant that the insecticidal protein functions as an orally active insect control agent, has a toxic effect, for example, by inhibiting the ability of the insect pest to survive, grow, and/or reproduce (e.g., causing morbidity and/or mortality) and/or is able to disrupt and/or deter insect feeding, which may or may not cause death of the insect. Thus, when an insecticidal protein of the invention is delivered to the insect, the result is typically morbidity and/or mortality of the insect and/or the insect reduces or stops feeding upon the source that makes the insecticidal protein available to the insect.

In the context of the present invention, a "chimeric" protein is a protein created by fusing all or a portion of at least two different proteins. In embodiments of the present invention, the chimeric protein is a chimeric Cry protein comprising all or a portion of two different Cry proteins fused together into a single polypeptide. A "chimeric insecticidal protein" is a chimeric protein that has insecticidal activity (as described herein).

A "coding sequence" is a nucleic acid sequence that is transcribed into RNA such as mRNA, rRNA, tRNA, snRNA, sense RNA or antisense RNA. In embodiments, the RNA is then translated to produce a protein.

As used herein, a "codon optimized" nucleotide sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the codon optimized nucleotide sequence. In certain embodiments, a nucleotide sequence is codon optimized for the cell (e.g., an animal, plant, fungal or bacterial cell) in which the construct is to be expressed. For example, a construct to be expressed in a plant cell can have all or parts of its sequence codon optimized for expression in a plant. See, for example, U.S. Pat. No. 6,121,014. In embodiments, the polynucleotides of the invention are codon-optimized for expression in a plant cell (e.g., a dicot cell or a monocot cell) or bacterial cell.

To "control" an insect pest means to inhibit, through a toxic effect, the ability of the insect pest to survive, grow, feed and/or reproduce and/or to limit insect-related damage or loss in a crop plant caused by the insect pest and/or to protect the yield potential of a crop caused by the pest when grown in the presence of an insect pest. To "control" an insect pest may or may not mean killing the insect, although in embodiments of the invention, "control" of the insect means killing the insect.

The term "comprise", "comprises" or "comprising," when used in this specification, indicates the presence of the stated features, integers, steps, operations, elements, or components, but does not preclude the presence or addition of one or more other features, integers, steps, operations, elements, components, and/or groups thereof.

As used herein, the transitional phrase "consisting essentially of" (and grammatical variants) means that the scope of a claim is to be interpreted to encompass the specified materials or steps recited in the claim "and those that do not materially alter the basic and novel characteristic(s)" of the claimed invention. Thus, the term "consisting essentially of" when used in a claim of this invention is not intended to be interpreted to be equivalent to "comprising."

In the context of the invention, "corresponding to" or "corresponds to" means that when the amino acid sequences of modified or homolog proteins are aligned with each other, the amino acids that "correspond to" certain enumerated positions in the modified or homolog protein are those that align with these positions in a reference protein, but are not necessarily in the same exact numerical positions relative to the particular reference amino acid sequence of the invention. For example, if SEQ ID NO: 2 (BT-0029) is the reference sequence and is aligned with SEQ ID NO: 1 (BT-0022) as in FIG. 1, the sequence TLEAVT immediately following Domain III in SEQ ID NO: 1 (BT-0022) "corresponds" to the sequence TFEAEY immediately following Domain III of SEQ ID NO: 2 (BT-0029).

As used herein, the term "Cry protein" means an insecticidal protein of a *Bacillus thuringiensis* crystal delta-endotoxin type. The term "Cry protein" can refer to the protoxin form or any insecticidally active fragment or toxin thereof including partially processed and the mature toxin form (e.g., without the N-terminal peptidyl fragment and/or the C-terminal protoxin tail).

As used herein, to "deliver" or "delivering" (and grammatical variations) a composition or insecticidal protein means that the composition or insecticidal protein comes in contact with an insect, which facilitates the oral ingestion of the composition or insecticidal protein, resulting in a toxic effect and control of the insect. The composition or insecticidal protein can be delivered in many recognized ways, including but not limited to, by transgenic plant expression, a formulated protein composition(s), a sprayable protein composition(s), a bait matrix, or any other art-recognized protein delivery system.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide group.

"Effective insect-controlling amount" means that concentration of an insecticidal protein that inhibits, through a toxic effect, the ability of an insect to survive, grow, feed and/or reproduce and/or that limits insect-related damage or loss in a crop plant. An "effective insect-controlling amount" may or may not mean killing the insect, although in embodiments it indicates killing the insect.

"Expression cassette" as used herein means a nucleic acid molecule capable of directing expression of at least one polynucleotide of interest, such as a polynucleotide that encodes an insecticidal protein of the invention, in an appropriate host cell, comprising a promoter operably linked to the polynucleotide of interest which is operably linked to a termination signal. An "expression cassette" also typically comprises additional polynucleotides to facilitate proper translation of the polynucleotide of interest. The expression cassette may also comprise other polynucleotides not related to the expression of a polynucleotide of interest but which are present due to convenient restriction sites for removal of the cassette from an expression vector. In embodiments, at least one of the components in the expression cassette may be heterologous (i.e., foreign) with respect to at least one of the other components (e.g., a heterologous promoter operatively associated with a polynucleotide of interest). The expression cassette may also be one that is naturally occurring but has been obtained in a recombinant form useful for heterologous expression. Typically, however, the expression cassette is heterologous with respect to the host, i.e., the expression cassette (or even the polynucleotide of interest) does not occur naturally in the host cell and has been introduced into the host cell or an ancestor cell thereof by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development (as described in more detail herein). An expression cassette, or fragment thereof, can also be referred to as "inserted polynucleotide" or "insertion polynucleotide" when transformed into a plant.

A "gene" is defined herein as a hereditary unit comprising one or more polynucleotides that occupies a specific location on a chromosome or plasmid and that contains the genetic instruction for a particular characteristic or trait in an organism.

As used herein, a "gut protease" refers to a protease naturally found in the digestive tract of an insect. This protease is usually involved in the digestion of ingested proteins. Examples of gut proteases include trypsin, which typically cleaves peptides on the C-terminal side of lysine (K) or arginine (R) residues, and chymotrypsin, which typically cleaves peptides on the C-terminal side of phenylalanine (F), tryptophan (W) or tyrosine (Y).

As used herein, the term "heterologous" means foreign, exogenous, non-native and/or non-naturally occurring. In embodiments, a "heterologous" polynucleotide or polypeptide is a polynucleotide or polypeptide that is not naturally associated with a host cell into which it is introduced, including non-naturally occurring multiple copies of a naturally occurring nucleotide sequence or polypeptide. In embodiments, a nucleotide sequence is heterologous to another sequence with which it is operatively associated, e.g., a promoter may be heterologous (i.e., foreign) to an operatively associated coding sequence.

As used here, "homologous" means native. For example, a homologous nucleotide sequence or amino acid sequence is a nucleotide sequence or amino acid sequence naturally associated with a host cell into which it is introduced, a homologous promoter sequence is the promoter sequence that is naturally associated with a coding sequence, and the like.

The terms "increase," "increasing," "increased," "enhance," "enhanced," "enhancing," and "enhancement" (and grammatical variations thereof) and similar terms, as used herein, describe an elevation in the control of a plant pest, e.g., by contacting a plant with a polypeptide of the invention (such as, for example, by transgenic expression or by topical application methods). This increase in control can be in reference to the level of control of the plant pest in the absence of the polypeptide of the invention (e.g., a plant that is not transgenically expressing the polypeptide or is not topically treated with the polypeptide). Thus, in embodiments, the terms "increase," "increasing," "increased," "enhance," "enhanced," "enhancing," and "enhancement" (and grammatical variations thereof), and similar terms can indicate an elevation of at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500% or more as compared to a suitable control (e.g., a plant, plant part, plant cell that is not contacted with a polypeptide of the invention).

"Insecticidal" as used herein is defined as a toxic biological activity capable of controlling an insect pest, optionally but preferably by killing them.

A nucleic acid sequence is "isocoding" with a reference nucleic acid sequence when the nucleic acid sequence encodes a polypeptide having the same amino acid sequence as the polypeptide encoded by the reference nucleic acid sequence.

In representative embodiments, the nucleic acids molecules, polynucleotides or proteins of the invention are "isolated." An "isolated" nucleic acid molecule, polynucleotide or protein, and the like, is a nucleic acid molecule, polynucleotide or protein, and the like that no longer exists in its natural environment. An isolated nucleic acid molecule, polynucleotide or protein of the invention may exist in a purified form or may exist in a recombinant host such as in a transgenic bacteria or a transgenic plant. In embodiments, an isolated nucleic acid molecule, nucleotide sequence or polypeptide exists in a purified form that is at least partially separated from at least some of the other components of the naturally occurring organism or virus, for example, the cell or viral structural components or other polypeptides or nucleic acids commonly found associated with the polynucleotide. In other embodiments, an "isolated" nucleic acid molecule, nucleotide sequence or polypeptide may exist in a non-native environment such as, for example, a recombinant host cell. Thus, for example, with respect to nucleotide sequences, the term "isolated" can mean that the nucleotide sequence is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism.

The terms "nucleic acid," "nucleic acid molecule," "nucleotide sequence," "oligonucleotide" and "polynucleotide" are used interchangeably herein, unless the context indicates otherwise, and refer to a heteropolymer of nucleotides. These terms include without limitation DNA and RNA molecules, including cDNA, genomic DNA, synthetic (e.g., chemically synthesized) DNA and RNA, plasmid DNA, mRNA, anti-sense RNA, and RNA/DNA hybrids, any of which can be linear or branched, single stranded or double stranded, or a combination thereof. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. In embodiments, the "nucleic acid," "nucleic acid molecule,", "nucleotide sequence,", "oligonucleotide" or "polynucleotide" refer to DNA.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to or "operatively associated" with the nucleotide sequence.

A "plant" as used herein, refers to any plant at any stage of development.

Any plant (or groupings of plants, for example, into a genus or higher order classification) can be employed in practicing the present invention including angiosperms or gymnosperms, monocots or dicots.

Exemplary plants include, but are not limited to corn (*Zea mays*), canola (*Brassica napus, Brassica rapa* ssp.), alfalfa (*Medicago saliva*), rice (*Oryza sativa*, including without limitation Indica and/or *Japonica* varieties), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tobacum*), potato (*Solanum tuberosum*), peanut (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*). duckweed (*Lemna* spp.), oats (*Avena sativa*), barley (*Hordium vulgare*), vegetables, ornamentals, conifers, and turfgrasses (e.g., for ornamental, recreational or forage purposes), and biomass grasses (e.g., switchgrass and *miscanthus*).

Vegetables include without limitation Solanaceous species (e.g., tomatoes; *Lycopersicon esculentum*), lettuce (e.g., *Lactuca sativa*), carrots (*Caucus carota*), cauliflower (*Brassica oleracea*), celery (*Apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as hubbard squash (*C. hubbard*), butternut squash (*C. moschata*), zucchini (*C. pepo*), crookneck squash (*C. crookneck*), *C. argyrosperma, C. argyrosperma* ssp *sororia, C. digitata, C. ecuadorensis, C. foetidissima, C. lundelliana*, and *C. martinezii*, and members of the genus *Cucumis* such as cucumber (*Cucumis sativus*), cantaloupe (*C. cantalupensis*), and musk melon (*C. melo*).

Ornamentals include without limitation azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and *chrysanthemum*.

Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudot-*

*suga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrass include but are not limited to zoysiagrasses, bentgrasses, fescue grasses, bluegrasses, St. Augustinegrasses, bermudagrasses, bufallograsses, ryegrasses, and orchardgrasses.

Also included are plants that serve primarily as laboratory models, e.g., *Arabidopsis*.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

A "plant cell culture" means a culture of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

As used herein, the term "plant part" includes but is not limited to embryos, pollen, ovules, seeds, leaves, flowers, branches, fruit, stalks, roots, root tips, anthers, and/or plant cells including plant cells that are intact in plants and/or parts of plants, plant protoplasts, plant tissues, plant cell tissue cultures, plant calli, plant clumps, and the like.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural or functional units. The use of this term in conjunction with, or in the absence of, any specific type of plant tissue as listed above or otherwise embraced by this definition is not intended to be exclusive of any other type of plant tissue.

A "polynucleotide of interest" refers to any polynucleotide which, when transferred to an organism, e.g., a plant, confers upon the organism a desired characteristic such as insect resistance, disease resistance, herbicide tolerance, antibiotic resistance, improved nutritional value, improved performance in an industrial process, production of a commercially valuable enzyme or metabolite, an altered reproductive capability, and the like.

A "portion" or "fragment" of a polypeptide of the invention will be understood to mean an amino acid sequence of reduced length relative to a reference amino acid sequence of a polypeptide of the invention. Such a portion or fragment according to the invention may be, where appropriate, included in a larger polypeptide of which it is a constituent (e.g., a tagged or fusion protein). In embodiments, the "portion" or "fragment" substantially retains insecticidal activity (e.g., at least 40%, 50%, 60%, 70%, 80%, 85%, 90%, 95% or even 100% of the activity of the full-length protein, or has even greater insecticidal activity than the full-length protein).

The terms "protein," "peptide" and "polypeptide" are used interchangeably herein.

The term "promoter" as used herein refers to a polynucleotide, typically upstream (5') of a coding polynucleotide, which controls the expression of the coding polynucleotide by providing the recognition for RNA polymerase and other transcriptional machinery.

A "protoplast" as used herein, refers to an isolated plant cell without a cell wall or with only parts of the cell wall.

As used herein, the term "recombinant" refers to a form of nucleic acid (e.g., DNA or RNA) or protein or an organism that would not normally be found in nature and as such was created by human intervention. As used herein, a "recombinant nucleic acid molecule" (and similar terms) is a nucleic acid molecule comprising a combination of polynucleotides that would not naturally occur together and is the result of human intervention, e.g., a nucleic acid molecule that is comprised of a combination of at least two polynucleotides heterologous to each other, or a nucleic acid molecule that is artificially synthesized and comprises a polynucleotide that deviates from the polynucleotide that would normally exist in nature, or a nucleic acid molecule that comprises a transgene artificially incorporated into a host cell's genomic DNA and the associated flanking DNA of the host cell's genome. An example of a recombinant nucleic acid molecule is a DNA molecule resulting from the insertion of a transgene into a plant's genomic DNA, which may ultimately result in the expression of a recombinant RNA or protein molecule in that organism. In embodiments, a "recombinant" protein is a protein that does not normally exist in nature or is present in a non-naturally occurring context, and is expressed from a recombinant nucleic acid molecule. As used herein, a "recombinant plant" is a plant that would not normally exist in nature, is the result of human intervention, and contains a recombinant polynucleotide (e.g., a transgene or heterologous nucleic acid molecule incorporated into its genome). As a result of such genomic alteration, the recombinant plant is distinctly different from the related wild-type plant.

The terms "reduce," "reduced," "reducing," "reduction," "diminish," and "suppress" (and grammatical variations thereof) and similar terms, as used herein, refer to a decrease in the survival, growth and/or reproduction of a plant pest, e.g., by contacting a plant with a polypeptide of the invention (such as, for example, by transgenic expression or by topical application methods). This decrease in survival, growth and/or reproduction can be in reference to the level observed in the absence of the polypeptide of the invention (e.g., a plant that is not transgenically expressing the polypeptide or is not topically treated with the polypeptide). Thus, in embodiments, the terms "reduce," "reduced," "reducing," "reduction," "diminish," and "suppress" (and grammatical variations thereof) and similar terms mean a decrease of at least about 5%, 10%, 15%, 20%, 25%, 30%, 35%, 40%, 45%, 50%, 55%, 60%, 65%, 70%, 75%, 80%, 85%, 90%, 95% or more as compared with a plant that is not contacted with a polypeptide of the invention (e.g., a plant that is not transgenically expressing the polypeptide or is not topically treated with the polypeptide). In representative embodiments, the reduction results in no or essentially no (i.e., an insignificant amount, e.g., less than about 10%, less than about 5% or even less than about 1%) detectable survival, growth and/or reproduction of the plant pest.

A "regulatory element" refers to a nucleotide sequence involved in controlling the expression of a polynucleotide. Examples of regulatory elements include promoters, termination signals, and nucleotide sequences that facilitate proper translation of a polynucleotide.

As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait).

As used herein, "specific activity" refers to the amount of protein required to have an insecticidal effect. Therefore, when a first protein has a higher specific activity than a second protein means that it takes a lesser amount of the first protein compared the second protein to have an insecticidal effect on the same percentage of insects.

The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more nucleotide or amino acid residue identity. In certain embodiments, substantial identity exists over a region of the sequences that is at least about 50 residues, 100 residues, 150 residues, 200 residues, 250 residues, 300 residues, 350 residues, 400 residues or more in length. In further embodiments, the sequences are substantially identical when they are identical over the entire length of the coding regions.

"Identity" or "percent identity" refers to the degree of identity between two nucleic acid or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Natl. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215:403 410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, *Proc. Natl. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a nucleic acid will selectively hybridize to a target sequence to a detectably greater degree than other sequences (e.g., at least 2-fold over a non-target sequence), and optionally may substantially exclude binding to non-target sequences. Stringent conditions are sequence-dependent and will vary under different circumstances. By controlling the stringency of the hybridization and/or washing conditions, target sequences can be identified that can be up to 100% complementary to the reference nucleotide sequence. Alternatively, conditions of moderate or even low stringency can be used to allow some mismatching in sequences so that lower degrees of sequence similarity are detected. For example, those skilled in the art will appreciate that to function as a primer or probe, a nucleic acid sequence only needs to be sufficiently complementary to the target sequence to substantially bind thereto so as to form a stable double-stranded structure under the conditions employed. Thus, primers or probes can be used under conditions of high, moderate or even low stringency. Likewise, conditions of low or moderate stringency can be advantageous to detect homolog, ortholog and/or paralog sequences having lower degrees of sequence identity than would be identified under highly stringent conditions.

The terms "complementary" or "complementarity" (and similar terms), as used herein, refer to the natural binding of polynucleotides under permissive salt and temperature conditions by base-pairing. For example, the sequence "A-G-T" binds to the complementary sequence "T-C-A." Complementarity between two single-stranded molecules may be partial, in which only some of the nucleotides bind, or it may be complete when total complementarity exists between the single stranded molecules. The degree of complementarity between nucleic acid strands has significant effects on the efficiency and strength of hybridization between the molecules. As used herein, the term "substantially complementary" (and similar terms) means that two nucleic acid sequences are at least about 50%, 60%, 70%, 75%, 80%, 85%, 90%, 95%, 96%, 97%, 98%, 99% or more complementary. Alternatively, the term "substantially complementary" (and similar terms) can mean that two nucleic acid sequences can hybridize together under high stringency conditions (as described herein).

As used herein, "specifically" or "selectively" hybridizing (and similar terms) refers to the binding, duplexing, or hybridizing of a molecule to a particular nucleic acid target sequence under stringent conditions when that sequence is present in a complex mixture (e.g., total cellular DNA or RNA) to the substantial exclusion of non-target nucleic acids, or even with no detectable binding, duplexing or hybridizing to non-target sequences. Specifically or selectively hybridizing sequences typically are at least about 40% complementary and are optionally substantially complementary or even completely complementary (i.e., 100% identical).

For DNA-DNA hybrids, the $T_m$ can be approximated from the equation of Meinkoth and Wahl, Anal. Biochem., 138: 267-84 (1984): $T_m$=81.5° C.+16.6 (log M)+0.41 (% GC)−0.61 (% formamide)−500/L; where M is the molarity of monovalent cations, % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired degree of identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, highly stringent conditions can utilize a hybridization and/or wash at the thermal melting point ($T_m$) or 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). If the desired degree of mismatching results in a $T_m$ of less than 45° C. (aqueous solution) or 32° C. (formamide solution), optionally the SSC concentration can be increased so that a higher temperature can be used. An extensive guide to the hybridization of nucleic acids is found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier, New York (1993); Current Protocols in Molecular Biology, chapter 2, Ausubel, et al., eds, Greene Publishing and Wiley-Interscience, New York (1995); and Green & Sambrook, In: Molecular Cloning, A Laboratory Manual, 4th Edition, Cold Spring Harbor Press, Cold Spring Harbor, N.Y. (2012).

Typically, stringent conditions are those in which the salt concentration is less than about 1.5 M Na ion, typically about 0.01 to 1.0 M Na ion concentration (or other salts) at about pH 7.0 to pH 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide or Denhardt's (5 g Ficoll, 5 g polyvinylpyrrolidone, 5 g bovine serum albumin in 500 ml of water). Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1 M NaCl, 1% SDS at 3° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. A further non-limiting example of high stringency conditions include hybridization in 4×SSC, 5×Denhardt's, 0.1 mg/ml boiled salmon sperm DNA, and 25 mM Na phosphate at 65° C. and a wash in 0.1×SSC, 0.1% SDS at 65° C. Another illustration of high stringency hybridization conditions includes hybridization in 7% SDS, 0.5 M NaPO$_4$, 1 mM EDTA at 50° C. with washing in 2×SSC, 0.1% SDS at 50° C., alternatively with washing in 1×SSC, 0.1% SDS at 50° C., alternatively with washing in 0.5×SSC, 0.1% SDS at 50° C., or alternatively with washing in 0.1×SSC, 0.1% SDS at 50° C., or even with washing in 0.1×SSC, 0.1% SDS at 65° C. Those skilled in the art will appreciate that specificity is typically a function of post-hybridization washes, the relevant factors being the ionic strength and temperature of the final wash solution.

Nucleic acids that do not hybridize to each other under stringent conditions are still substantially identical if the proteins that they encode are substantially identical (e.g., due to the degeneracy of the genetic code).

A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

As used herein, if a modified polypeptide or fragment (and the like) "substantially retains" insecticidal activity, it is meant that the modified polypeptide or fragment retains at least about 40%, 50%, 60%, 70%, 80%, 85%, 90%, 95% or even 100% of the insecticidal activity of the reference protein, or has even greater insecticidal activity.

"Synthetic" refers to a nucleotide sequence comprising bases or a structural feature(s) that is not present in the natural sequence. For example, an artificial sequence encoding a protein of the invention that resembles more closely the G+C content and the normal codon distribution of dicot or monocot plant genes is said to be synthetic.

As used herein, a protein that is "toxic" to an insect pest is an orally-active insect control agent that kills the insect pest, causes a reduction in growth and/or reproduction of the insect pest and/or is able to disrupt or deter insect feeding, the latter two of which may or may not cause death of the insect. When a protein of the invention is delivered to an insect or an insect comes into contact with the protein, the result is typically death of the insect, the insect's growth and/or reproduction is slowed and/or the insect reduces or stops feeding upon the source that makes the toxic protein available to the insect.

The terms "toxin fragment" and "toxin portion" are used interchangeably herein to refer to a fragment or portion of a longer (e.g., full-length) chimeric insecticidal protein of the invention, where the "toxin fragment" or "toxin portion" retains insecticidal activity. For example, it is known in the art that native Cry proteins are expressed as protoxins that are processed at the N-terminal and C-terminal ends to produce a mature toxin. In embodiments, the "toxin fragment" or "toxin portion" of a chimeric insecticidal protein of the invention is truncated at the N-terminus and/or C-terminus. In embodiments, the "toxin fragment" or "toxin portion" is truncated at the N-terminus to remove part or all of the N-terminal peptidyl fragment, and optionally comprises at least about 400, 425, 450, 475, 500, 510, 520, 530, 540, 550, 560, 570, 580 or 590 contiguous amino acids of chimeric insecticidal protein specifically described herein or an amino acid sequence that is substantially identical thereto. Thus, in embodiments, a "toxin fragment" or "toxin portion" of a chimeric insecticidal protein is truncated at the N-terminus (e.g., to omit part or all of the peptidyl fragment), for example, an N-terminal truncation of one amino acid or more than one amino acid, e.g., up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more amino acids. In embodiments, a "toxin fragment" or "toxin portion" of a chimeric insecticidal protein is truncated at the C-terminus (e.g., to omit part or all of the protoxin tail), for example, a C-terminal truncation of one amino acid or more than one amino acid, e.g., up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 125, 150, 175, 200, 225, 250, 275, 300, 325, 350, 375, 400, 425, 450, 475, 500, 525, 550, 560 or more amino acids. In embodiments, the "toxin fragment" or "toxin portion" comprises domains 1 and 2, and the core domain III (e.g., as shown in FIG. 2). In embodiments, the "toxin fragment" or "toxin portion" is the mature (i.e., processed) toxin (e.g., Cry toxin).

"Transformation" is a process for introducing a heterologous nucleic acid into a host cell or organism. In particular embodiments, "transformation" means the stable integration of a DNA molecule into the genome of an organism of interest (e.g., a plant cell).

The terms "transformed" and "transgenic" as used herein refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. "Transformed" or "transgenic" cells, tissues, or plants are understood to encompass not only the end product of a transformation process, but also progeny thereof comprising the heterologous nucleic acid molecule. A "non-transformed" or "non-transgenic" host refers to a wild-type organism, e.g., a bacterium or plant, which does not contain the heterologous nucleic acid molecule.

The term "vector" refers to a composition for transferring, delivering or introducing a nucleic acid (or nucleic acids) into a cell. A vector comprises a nucleic acid molecule comprising the nucleotide sequence(s) to be transferred, delivered or introduced.

Chimeric Insecticidal Proteins.

The present invention provides novel chimeric insecticidal proteins comprising at least one region from a first Cry protein (e.g., a BT-0029 protein [SEQ ID NO: 2] and substantially identical variants thereof). In embodiments, the invention provides a chimeric insecticidal protein comprising a region from two or more different Cry proteins. In embodiments, the resulting chimeric insecticidal protein has increased activity against one or more insect pests (e.g., an enhanced activity or activity against a new target pest) and/or a different mode of action against one or more insect pests as compared with one or more (or even all) of the parent proteins. In representative embodiments, the chimeric insecticidal protein is a chimera comprising regions from two different Cry (e.g., Cry1) proteins, and the chimera has increased insecticidal activity against one or more insect pests as compared with both parent proteins.

In embodiments, the chimeric insecticidal proteins of the invention can provide new modes of action against one or more target insect pests. For example, the chimeric insecticidal protein can have insecticidal activity against an insect pest or colony that is generally resistant to the insecticidal activity of another agent (e.g., an insecticidal protein, including without limitation a Bt protein, such as a Cry protein or a Vip protein). In embodiments, the parent proteins themselves are not insecticidally active, or only weakly active, against the resistant insect pest or colony, which may suggest that the chimera has a novel mode of action as compared with the parent proteins. For example, if the parent proteins are active against a target insect pest ("susceptible"), but not against a resistant counterpart, and the chimeric insecticidal protein is active against the resistant insect pest, that is an indication that the chimeric insecticidal protein is toxic to the resistant pest via a novel mode of action.

Accordingly, in embodiments, the invention provides a chimeric insecticidal protein that is toxic to an insect pest (e.g., a lepidopteran insect pest), the chimeric insecticidal protein comprising a region from a BT-0029 protein (SEQ ID NO: 2) or a polypeptide that is substantially identical to the region from a BT-0029 protein. In embodiments, the chimeric insecticidal protein comprises an N-terminal region of a first Cry1 protein, which is optionally a BT-0029 protein (SEQ ID NO: 2) or a polypeptide comprising an amino acid sequence that is substantially identical to the N-terminal region of the BT-0029 protein. In embodiments, the N-terminal region of the first Cry protein is fused to a C-terminal region from a different Cry protein (e.g., a different Cry1 protein) to form a chimeric insecticidal protein (e.g., a chimeric insecticidal Cry protein).

In representative embodiments, the C-terminal region from a different Cry protein can be a C-terminal region from a different Cry1 protein or a polypeptide comprising an amino acid sequence that is substantially identical to the C-terminal region from the different Cry1 protein.

Thus, in a representative embodiment, a chimeric insecticidal protein of the invention comprises, consists essentially of, or consists of, in an N-terminal to a C-terminal direction: (a) an N-terminal region of a first Cry protein (e.g., a Cry1 protein), which is optionally an N-terminal region of a BT-0029 protein or an amino acid sequence that is substantially identical to the N-terminal region of the BT-0029 protein, fused to (b) a C-terminal region of a different Cry protein (e.g., a different Cry1 protein).

In representative embodiments, the different Cry protein (e.g., Cry1 protein) is selected based on an alignment of the C-terminal region from the different Cry protein and the corresponding region from the first Cry protein (e.g., a Cry1 protein), for example, see the exemplary alignments in FIGS. 1A and 1B. In embodiments, the different Cry protein is selected such that the amino acid sequence of the C-terminal region of the different Cry protein is substantially identical to the corresponding region of the first Cry protein. In exemplary embodiments, the amino acid sequence of the C-terminal region of the different Cry protein (e.g., Cry1 protein) is at least about 85%, 86%, 87%, 88%, 89%, 90%, 91%, 92%, 93%, 94%, 95%, 96%, 97%, 98%, 99% or more identical with an amino acid sequence of the corresponding C-terminal region from the first Cry protein. Methods of aligning and determining amino acid sequence identity across an aligned region are well known by those skilled in the art.

In embodiments, the different Cry1 protein includes without limitation a Cry1F protein (e.g., a Cry1Fa or a Cry1Fb protein), a Cry1G protein (e.g., a Cry1Ga, a Cry1Gb, or a Cry1Gc protein), a Cry1I protein (e.g., a Cry1Ia protein, a Cry1Ib protein, a Cry1Ic protein, a Cry1Id protein, a Cry1Ie protein, a Cry1If protein, or a Cry1Ig protein), a Cry1K (e.g., a Cry1Ka protein), or a Cry1C (e.g. a Cry1Ca protein). In embodiments, the different Cry1 protein is a Cry1If protein, optionally a BT-0022 protein (SEQ ID NO: 1). In embodiments, a different Cry1 protein is a Cry1Fa protein (SEQ ID NO: 8). In embodiments, a different Cry1 protein is a Cry1K protein (SEQ ID NO: 12). In embodiments, a different Cry1 protein is a Cry1Ca protein (SEQ ID NO: 17).

The terms "N-terminal region" and a "C-terminal region" do not necessarily indicate that the most N-terminal or C-terminal amino acids (e.g., the N-terminus or C-terminus), respectively, of the full-length protein are included within the region. For example, it is well-known by those skilled in the art that Cry protoxins are processed at both the N-terminus and C-terminus to produce a mature (i.e., processed) toxin. Thus, in embodiments, the "N-terminal region" and/or the "C-terminal region" omit some or all of the processed out portions of the protoxin such that the chimeric insecticidal protein comprises the mature toxin protein (e.g., Cry protein Domains I, II and III), without some or all of the N-terminal peptidyl fragment and/or the C-terminal protoxin tail, or a polypeptide that is substantially identical to the mature toxin protein. In embodiments, the chimeric insecticidal protein comprises the peptidyl fragment and/or protoxin tail. In embodiments, the chimeric insecticidal protein does not comprise the peptidyl fragment or protoxin tail, i.e., corresponds to the mature processed toxin.

In embodiments, the N-terminal region of the first Cry1 protein comprises, consists essentially of, or consists of a polypeptide corresponding to an amino acid sequence from about position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 to about position 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 or 500 of SEQ ID NO: 2 (full-length BT-0029), and any combination of lower and upper positions as if each such combination were specifically set forth herein.

In embodiments, the N-terminal region of the first Cry1 protein comprises, consists essentially of, or consists of a polypeptide corresponding to an amino acid sequence from about position 1 to about position 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490 or 491 of SEQ ID NO: 2.

In a representative embodiment, the N-terminal region of the first Cry1 protein comprises, consists essentially of, or consists of an amino acid sequence corresponding to an amino acid sequence from about position 1 to about amino acid position 458 of SEQ ID NO: 2.

In representative embodiments, the C-terminal region of the second Cry1 protein comprises, consists essentially of, or consists of a polypeptide corresponding to an amino acid sequence from about position 435, 436, 437, 438, 439, 440, 441, 442, 443, 444, 445, 446, 447, 448, 449, 450, 451, 452, 453, 454, 455, 456, 457, 458, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 or 500 to about position 580, 581, 582, 583, 584, 585, 586, 587, 588, 589, 590, 591, 592, 593, 594, 595, 596, 587, 598, 599, 600, 601, 602, 603, 604, 605, 606, 607, 608, 609, 610, 611, 612, 613, 614, 615, 616, 617, 618, 619 or 620 of SEQ ID NO: 8 (full-length Cry1Fa), and any combination of lower and upper positions as if each such combination were specifically set forth herein.

In embodiments, the C-terminal region of the second Cry1 protein comprises, consists essentially of, or consists of a polypeptide corresponding to an amino acid sequence from about position 464 to about position 580, 581, 582, 583, 584, 585, 586, 587, 588, 589, 590, 591, 592, 593, 594, 595, 596, 587, 598, 599, 600, 601, 602, 603, 604, 605, 606, 607, 608, 609, 610, 611, 612, 613, 614, 615, 616, 617, 618, 619 or 620 of SEQ ID NO: 8.

In embodiments, the C-terminal region of the second Cry1 protein comprises, consists essentially of, or consists of a polypeptide corresponding to an amino acid sequence from about position 435, 436, 437, 438, 439, 440, 441, 442, 443, 444, 445, 446, 447, 448, 449, 450, 451, 452, 453, 454, 455, 456, 457, 458, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 or 500 to about position 602 of SEQ ID NO: 8.

In embodiments, the C-terminal region of the second Cry1 protein comprises, consists essentially of, or consists of a polypeptide corresponding to an amino acid sequence from about position 464 to about position 602 of SEQ ID NO: 8.

In representative embodiments, the C-terminal region of the second Cry1 protein comprises, consists essentially of, or consists of a polypeptide corresponding to an amino acid sequence from about position 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, or 535 to about position 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654 or 655 of SEQ ID NO: 1 (full-length BT-0022), and any combination of lower and upper positions as if each such combination were specifically set forth herein.

In embodiments, the C-terminal region of the second Cry1 protein comprises, consists essentially of, or consists of a polypeptide corresponding to an amino acid sequence from about position 498 to about position 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654 or 655 of SEQ ID NO: 1.

In embodiments, the C-terminal region of the second Cry1 protein comprises, consists essentially of, or consists of a polypeptide corresponding to an amino acid sequence from about position 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, or 535 to about position 636 of SEQ ID NO: 1.

In embodiments, the C-terminal region of the second Cry1 protein comprises, consists essentially of, or consists of a polypeptide corresponding to an amino acid sequence from about position 498 to about position 636 of SEQ ID NO: 1.

In representative embodiments, the C-terminal region of the second Cry1 protein comprises, consists essentially of, or consists of a polypeptide corresponding to an amino acid sequence from about position 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536 or 537 to about position 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656 or 657 of SEQ ID NO: 12 (full-length Cry1Ka), and any combination of lower and upper positions as if each such combination were specifically set forth herein.

In embodiments, the C-terminal region of the second Cry1 protein comprises, consists essentially of, or consists of a polypeptide corresponding to an amino acid sequence from about position 500 to about position 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656 or 657 of SEQ ID NO: 12.

In embodiments, the C-terminal region of the second Cry1 protein comprises, consists essentially of, or consists of a polypeptide corresponding to an amino acid sequence from about position 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537 to about position 597 of SEQ ID NO: 12.

In embodiments, the C-terminal region of the second Cry1 protein comprises, consists essentially of, or consists of a polypeptide corresponding to an amino acid sequence from about position 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537 to about position 610 of SEQ ID NO: 12.

In embodiments, the C-terminal region of the second Cry1 protein comprises, consists essentially of, or consists of a polypeptide corresponding to an amino acid sequence from about position 500 to about position 597 of SEQ ID NO: 12.

In embodiments, the C-terminal region of the second Cry1 protein comprises, consists essentially of, or consists of a polypeptide corresponding to an amino acid sequence from about position 500 to about position 610 of SEQ ID NO: 12.

In representative embodiments, the C-terminal region of the second Cry1 protein comprises, consists essentially of, or consists of a polypeptide corresponding to an amino acid sequence from about position 435, 436, 437, 438, 439, 440, 441, 442, 443, 444, 445, 446, 447, 448, 449, 450, 451, 452, 453, 454, 455, 456, 457, 458, 449, 450, 451, 452, 453, 454, 455, 456, 457, 458, 459, 460, 461, 462, 463, 464, 465, 466 or 467 to about position 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616 or 617 of SEQ ID NO: 17 (full-length Cry1Ca), and any combination of lower and upper positions as if each such combination were specifically set forth herein.

In embodiments, the C-terminal region of the second Cry1 protein comprises, consists essentially of, or consists of a polypeptide corresponding to an amino acid sequence from about position 467 to about position 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616 or 617 of SEQ ID NO: 17.

In embodiments, the C-terminal region of the second Cry1 protein comprises, consists essentially of, or consists of a polypeptide corresponding to an amino acid sequence from about position 435, 436, 437, 438, 439, 440, 441, 442, 443, 444, 445, 446, 447, 448, 449, 450, 451, 452, 453, 454, 455, 456, 457, 458, 449, 450, 451, 452, 453, 454, 455, 456, 457, 458, 459, 460, 461, 462, 463, 464, 465, 466 or 467 to about position 617 of SEQ ID NO: 17.

In embodiments, the C-terminal region of the second Cry1 protein comprises, consists essentially of, or consists of a polypeptide corresponding to an amino acid sequence from about position 467 to about position 617 of SEQ ID NO: 17.

As is well known in the art, Cry proteins from Bt have 5 conserved sequence domains (Conserved Block [CB] 1 to 5]) separated by more variable regions (Hofte & Whitely, 1989, Microbiol. Rev. 53:242-255), and three conserved structural domains (Domains I, II and III) (de Maagd et al., 2001, Trends Genetics 17:193-199). FIGS. 1A and 1B show an alignment of the Cry proteins BT-0029, BT-0022, Cry1Fa and Cry1Ka, with CB3 and Domain III indicated. Those skilled in the art can use the well-known sequence and structural information available for Cry proteins to create a chimeric insecticidal Cry protein according to the invention, for example, to select a suitable crossover region(s) between two Cry proteins. In embodiments, a crossover region is located within a conserved block, for example, within CB3. The term "within a conserved block" includes the positions at each end of the conserved block. To illustrate, the term "within CB3" includes the position immediately before (e.g., between the methionine and phenylalanine residues within the sequence VPMFSW in the BT-0029 sequence of FIG. 2A) and immediately after (e.g., between the threonine and asparagine residues within the sequence RRTNVG in the BT-0029 sequence of FIG. 2A) conserved block 3. FIGS. 2A and 2B show exemplary chimeric insecticidal proteins according to the invention with a crossover region within CB3.

With reference to FIG. 2A, in embodiments, a crossover is located in a position corresponding to a position immediately before amino acid residue 1 or immediately following amino acid residue 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or 51, or any combination thereof, in CB3. In embodiments, a crossover is located within a region (including the residues at each end of the region) corresponding to amino acid residue 2 to amino acid residue 7, 8, 9 or 10 of CB3, within a region corresponding to amino acid residue 11 to amino acid residue 14, 15, 16, 17 or 18 of CB3, within a region corresponding to amino acid residue 19 to amino acid residue 27, 28, 29, 30, 31, 32, 33, 34, 35 or 36 of CB3 and/or within a region corresponding to amino acid residue 37, 38 or 39 to amino acid residue 51, and any combination of such regions. In representative embodiments, a crossover is located in a position within a region corresponding to amino acid residue 19 to amino acid residue 51, amino acid residue 19 to amino acid residue 33, amino acid residue 19 to amino acid residue 28, amino acid residue 19 to amino acid residue 27, or amino acid residue 19 to amino acid residue 26 in CB3. In embodiments, a crossover position is located at the specific site in between amino acid residue 18 and amino acid residue 19 in CB3 (e.g., specifically in between the valine and isoleucine in the sequence DPDVITQ in BT-0029, SEQ ID NO: 2).

The chimeric insecticidal proteins can also be defined with respect to the structural domains derived from each of the parent molecules. For example, in embodiments, the N-terminal region of the first Cry protein comprises domain I of the first Cry protein and all or essentially all of domain II. In embodiments, the C-terminal region of the different Cry protein comprises all or essentially all of domain III of the different Cry protein. Those skilled in the art understand that there is some variability in delineating the precise location of the ends of the Cry protein structural domains and the linker regions between the domains, for example, the location of the end of the linker region between domains II and III and the beginning of domain III, although the core of domain III is readily identifiable to those skilled in the art (e.g., corresponding to the location of the core domain III as shown in FIG. 1A and FIG. 2A). In embodiments, the crossover between the N-terminal region of the first Cry protein and the C-terminal region derived from the different Cry protein is located in CB3.

In representative embodiments, the C-terminal region of the different Cry protein (e.g., Cry1 protein) is selected based on an alignment of domain III (e.g., a core domain III as shown in FIG. 1A) from the different Cry protein and the corresponding domain III sequence from the first Cry protein (e.g., a Cry1 protein, such as BT-0029), for example, see the exemplary alignments in FIGS. 1A and 1B, with domain III specifically indicated. In embodiments, the different Cry protein is selected such that the amino acid sequence of domain III of the different Cry protein is substantially identical to the corresponding domain III region of the first Cry protein (e.g., BT-0029). In exemplary embodiments, the amino acid sequence of the domain III region of the different Cry protein (e.g., Cry1 protein) is at least about 85%, 86%, 87%, 88%, 89%, 90%, 91%, 92%, 93%, 94%, 95%, 96%, 97%, 98%, 99% or more identical with an amino acid sequence of the corresponding domain III region from the first Cry protein. Methods of aligning and determining amino acid sequence identity across an aligned region are well known by those skilled in the art.

In particular embodiments, a chimeric insecticidal protein of the invention comprises, consists essentially of, or consists of (a) the amino acid sequence of any one of amino acids 1 to 597 of SEQ ID NO: 3, SEQ ID NO: 9, or SEQ ID NO: 13 or amino acids 1 to 610 of SEQ ID NO: 15, or amino acids 1 to 617 SEQ ID NO: 18, or a toxin fragment of any of SEQ ID Nos: 3, 9, 13, 15, or 18; or (b) an amino acid sequence that is substantially identical to the amino acid sequence of (a).

In particular embodiments, a chimeric insecticidal protein of the invention comprises, consists essentially of, or consists of (a) the amino acid sequence of any one of amino acids 1 to 603 of SEQ ID NO: 3, SEQ ID NO: 9 or SEQ ID NO: 13, or amino acids 1 to 615 of SEQ ID NO:15 or SEQ ID NO:18, or a toxin fragment thereof; or (b) an amino acid sequence that is substantially identical to the amino acid sequence of (a).

In particular embodiments, a chimeric insecticidal protein of the invention comprises, consists essentially of, or consists of (a) the amino acid sequence of any one of amino acids 1 to 607 of SEQ ID NO: 3, SEQ ID NO: 9 or SEQ ID NO: 13, or amino acids 1 to 620 of SEQ ID NO: 15 or SEQ ID NO: 18, or a toxin fragment thereof; or (b) an amino acid sequence that is substantially identical to the amino acid sequence of (a).

In particular embodiments, a chimeric insecticidal protein of the invention comprises, consists essentially of, or consists of (a) the amino acid sequence of any one of amino acids 1 to 610 of SEQ ID NO: 3, SEQ ID NO: 9 or SEQ ID NO: 13, or amino acids 1 to 620 of SEQ ID NO: 15 or SEQ ID NO: 18, or a toxin fragment thereof; or (b) an amino acid sequence that is substantially identical to the amino acid sequence of (a).

As is understood by those skilled in the art, native Cry toxins are expressed as protoxins that are processed to produce a mature processed toxin by cleaving an N-terminal peptidyl fragment and a C-terminal protoxin tail. The N-terminal peptidyl fragment and/or the C-terminal protoxin tail may function to enhance the stability and/or the insecticidal activity of the Cry toxin. In embodiments of the invention, the chimeric insecticidal protein comprises all or a portion of an N-terminal peptidyl fragment and/or a protoxin tail. In embodiments, the chimeric insecticidal protein does not comprise a full N-terminal peptidyl fragment and/or a full protoxin tail. In embodiments, the chimeric insecticidal protein does not comprise an N-terminal peptidyl fragment and/or a protoxin tail, i.e., corresponds to the mature processed toxin.

In embodiments, the N-terminal peptidyl fragment is derived from a Cry protein (e.g., from the first Cry protein, which is optionally a Cry1 protein). In other embodiments, the N-terminal peptidyl fragment is heterologous to the first Cry protein, for example, is not derived from a Cry protein and/or is partially or completely synthetic. In embodiments, the peptidyl fragment comprises at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more amino acids, optionally from the first Cry protein, including without limitation a first Cry1 protein (e.g., BT-0029, SEQ ID NO: 2). In embodiments, the peptidyl fragment comprises amino acids from about amino acid 1 to about amino acid 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 of the first Cry protein, e.g., a Cry1 protein such as BT-0029.

In embodiments, the chimeric insecticidal protein of the invention comprises at the C-terminus a protoxin tail region of a Bt Cry protein, including modifications of native Cry protein protoxin tails that are substantially identical to a native Cry protein protoxin tail. In embodiments, the protoxin tail is from a lepidopteran-active Cry protein. In embodiments, the protoxin tail is not derived from a Cry protein and/or is partially or completely synthetic. In embodiments, the Cry protein is heterologous to the first Cry protein and/or the different Cry protein. In embodiments, the protoxin tail is from a Cry1 protein, e.g., a BT-0029, a BT-0022, a Cry1F (e.g., Cry1Fa), a Cry1I (e.g., a Cry1Ia or a Cry1If), a Cry1K (e.g., a Cry1Ka), or a Cry1C (e.g. Cry1Ca), or is a polypeptide that is substantially identical to a protoxin tail (or fragment thereof) from any of the foregoing. The protoxin tail region may comprise an entire protoxin tail of a Cry protein or any portion thereof. In embodiments, the protoxin tail region comprises at least about 5, 6, 7, 8, 9, 10, 11, 12, 13, 14, 15, 20, 25, 30, 35, 38, 40, 45, 50 or more contiguous amino acids of a Cry protein protoxin tail (e.g., a Cry1 protoxin tail, such as a BT-0029), for example, as shown for the various Cry proteins in FIG. 1A. In embodiments, the protoxin tail comprises at least about 5, 6, 7, 8, 9, 10, 11, 12, 13, 14, 15, 20, 25, 30, 35, 38, 40, 45, 50 or more contiguous amino acids starting with amino acid position 598 of SEQ ID NO: 2 (BT-0029) or the corresponding region from another Cry protein, such as a Cry1 protein (e.g., BT-0022, a Cry1I, a Cry1F, a Cry1K or a Cry1C protein). In embodiments, the protoxin tail comprises amino acids 598 to 1169, or 598 to 652, or 598 to 636, or 598 to 622, or 598 to 610, or 598 to 607, or 598 to 603, or 598 to 600 of SEQ ID NO: 2 (BT-0029) or the corresponding region from another Cry protein (see, e.g., the alignment of BT-0029 with BT-0022, Cry1Fa and Cry1Ka in FIGS. 1A and 1B). In some embodiments, the chimeric insecticidal protein comprises any of SEQ ID Nos:20-25 or SEQ ID Nos:32-35. In other embodiments, the protoxin tail comprises amino acids 637 to 715, or 637 to 691, or 637 to 675, or 637 to 661, or 637 to 649, or 637 to 646, or 637 to 642 of SEQ ID NO: 1 (BT-0022). In still other embodiments, a chimeric insecticidal protein of the invention comprises, consists essentially of, or consists of any of SEQ ID Nos: 26-31.

Accordingly, in embodiments, a chimeric insecticidal protein of the invention comprises, consists essentially of, or consists of (a) the amino acid sequence of any one of SEQ ID NO: 3, SEQ ID NO: 9, SEQ ID NO: 13, SEQ ID NO: 15, SEQ ID NO: 18, SEQ ID Nos:20-35, or a toxin fragment thereof; or (b) an amino acid sequence that is substantially identical to the amino acid sequence of (a). In optional embodiments, the chimeric insecticidal protein of the invention comprises, consists essentially of, or consists of the amino acid sequence of any one of amino acids SEQ ID NO: 3, SEQ ID NO: 9, SEQ ID NO: 13, SEQ ID NO: 15, SEQ ID NO: 18 or SEQ ID Nos: 20-35.

Those skilled in the art will appreciate that the chimeric insecticidal proteins of the invention can further comprise other functional domains and/or peptide tags, for example a peptide tag on the N-terminus and/or C-terminus. For example, it may be useful to express the chimeric insecticidal protein with a peptide tag that can be recognized by a commercially available antibody (e.g., a FLAG motif) or with a peptide tag that facilitates purification (e.g., by addition of a poly-His tag) and/or detection. Alternatively, an epitope can be introduced into the chimeric protein to facilitate the generation of antibodies that specifically recognize the modified chimeric protein to distinguish the modified chimeric protein from the unmodified chimera and/or a parent protein(s). For example, one or more amino acids can be substituted into an antigenic loop of the native sequence to create a new epitope. In one embodiment, the antigenic loop is located in a non-conserved region outside of domain I of the native Cry protein. In embodiments, the antigenic loop is not a loop involved in insect gut receptor recognition by the Cry protein and/or is not involved in the protease activation of the Cry protein. In other embodiments, the chimeric protein can be modified to enhance its stability, for example, by fusing a maltose binding protein (MBP) or glutathione-S-transferase to the polypeptide. As another alternative, the fusion protein can comprise a reporter molecule.

Chimeric insecticidal proteins that are modified by introduction or elimination of a protease processing site at an appropriate position(s) to provide, or eliminate, proteolytic cleavage by an insect, plant and/or microorganism protease are also within the scope of the invention. In embodiments, the modified chimeric insecticidal protein substantially retains insectidical activity. In embodiments, the stability and/or insecticidal activity of such modified chimeric proteins is increased as compared with the chimeric insecticidal protein that does not contain such modification to introduce/eliminate a protease cleavage site.

Thus, the invention encompasses polypeptides having amino acid sequences that are substantially identical to those specifically disclosed herein, and toxin fragments thereof. It will be understood that the chimeric insecticidal proteins specifically disclosed herein will typically tolerate modifications in the amino acid sequence and substantially retain biological activity (e.g., insecticidal activity). Such modifications include insertions, deletions (including truncations at either terminus), and substitutions of one or more amino acids, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions and/or insertions.

To identify substantially identical polypeptides to the chimeric insecticidal proteins specifically disclosed herein, amino acid substitutions may be based on any characteristic known in the art, including the relative similarity or differences of the amino acid side-chain substituents, for example, their hydrophobicity, hydrophilicity, charge, size, and the like.

For example, in identifying amino acid sequences encoding insecticidal polypeptides other than those specifically disclosed herein, the hydropathic index of amino acids may be considered. The importance of the hydropathic amino acid index in conferring interactive biologic function on a protein is generally understood in the art (see, Kyte and Doolittle, (1982) J. Mol. Biol. 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Id.), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the chimeric polypeptides specifically disclosed herein.

It is also understood in the art that the substitution of amino acids can be made on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (.+−0.3.0); aspartate (+3.0.+−0.1); glutamate (+3.0.+−0.1); serine (+0.3); asparagine (+0.2); glutamine (+0.2); glycine (0); threonine (−0.4); proline (−0.5+I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional insecticidal polypeptides beyond those specifically disclosed herein.

The chimeric insecticidal proteins of the invention, including modifications and toxin fragments of the chimeric polypeptide specifically disclosed herein, can be made by any suitable method known in the art, generally by modifying the coding nucleic acid sequences. Methods of manipulating and modifying nucleic acids to achieve a desired modification are well-known in the art. In addition, gene editing techniques can also be used produce a chimeric insecticidal protein of the invention or to make further modifications thereto.

As another approach, the polypeptide to be modified can be expressed in a host cell that exhibits a high rate of base mis-incorporation during DNA replication, such as XL-1 Red (Stratagene, La Jolla, Calif.). After propagation in such strains, one can isolate the DNA (for example, by preparing plasmid DNA or by PCR amplification and cloning of the resulting PCR fragment into a vector), culture the protein mutations in a non-mutagenic strain, and identify mutated genes with insecticidal activity, for example, by performing an assay to test for insecticidal activity. In exemplary methods, the protein is mixed and used in feeding assays. See, for example, Marrone et al. (1985) J. of Economic Entomology 78:290-293. Such assays can include contacting plants with one or more pests and determining the plant's ability to survive or cause the death of the pests. Examples of mutations that result in increased toxicity are found in Schnepf et al. (1998) Microbiol. Mol. Biol. Rev. 62:775-806.

In embodiments, the chimeric insecticidal protein (including substantially similar polypeptides and toxin fragments) of the invention is isolated. In embodiments, the chimeric insecticidal protein (including substantially similar polypeptides and toxin fragments) of the invention is a recombinant protein.

The chimeric insecticidal proteins of the invention have insecticidal activity against a lepidopteran pest. In embodiments, the chimeric insecticidal protein has activity against one or more of the following non-limiting examples of a lepidopteran pest: *Ostrinia* spp. such as *O. nubilalis* (European corn borer) and/or *O. furnacalis* (Asian corn borer); *Plutella* spp. such as *P. xylostella* (diamondback moth); *Spodoptera* spp. such as *S. frugiperda* (fall armyworm), *S. littoralis* (Egyptian cotton leafworm), *S. ornithogalli* (yellowstriped armyworm), *S. praefica* (western yellowstriped armyworm), *S. eridania* (southern armyworm) and/or *S. exigua* (beet armyworm); *Agrotis* spp. such as *A. ipsilon* (black cutworm), *A. segetum* (common cutworm), *A. gladiaria* (claybacked cutworm), and/or *A. orthogonia* (pale western cutworm); *Striacosta* spp. such as *S. albicosta* (western bean cutworm); *Helicoverpa* spp. such as *H. zea* (corn earworm), *H. punctigera* (native budworm), and/or *H. armigera* (cotton bollworm); *Heliothis* spp. such as *H. virescens* (tobacco budworm); *Diatraea* spp. such as *D. grandiosella* (southwestern corn borer) and/or *D. saccharalis* (sugarcane borer); *Trichoplusia* spp. such as *T. ni* (cabbage looper); *Sesamia* spp. such as *S. nonagroides* (Mediterranean corn borer) and/or *S. calamistis* (pink stem borer); *Pectinophora* spp. such as *P. gossypiella* (pink bollworm); *Cochylis* spp. such as *C. hospes* (banded sunflower moth); *Manduca* spp. such as *M. sexta* (tobacco hornworm) and/or *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. unipuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Chrysodeixis* spp. Such as *C. includes* (soybean looper); *Feltia* spp. such as *F. ducens* (dingy cutworm); *Chilo* spp. such as *C. suppressalis* (striped stem borer), *Cnaphalocrocis* spp. such as *C. medinalis* (rice leaffolder), or any combination of the foregoing.

Optionally, the chimeric insecticidal protein has increased activity against one or more lepidopteran pests as compared with one or more of the parent molecules (e.g., the first Cry protein and the different Cry protein). In embodiments, the chimeric insecticidal protein has increased activity against one or more lepidopteran pests as compared with BT-0029. In embodiments, the chimeric insecticidal protein has increased activity against one or more lepidopteran pests as compared with BT-0022, a Cry1Fa, a Cry1Ia, a Cry1If, a Cry1Ka, or a Cry1C.

In embodiments, the chimeric insecticidal protein has enhanced insecticidal activity against fall armyworm (*Spodoptera frugiperda*) as compared with one or more of the parent molecules (e.g., the first Cry protein and the different Cry protein). In embodiments, the chimeric insecticidal protein has increased activity against fall armyworm as compared with BT-0029. In embodiments, the chimeric insecticidal protein has increased activity against fall armyworm as compared with BT-0022, a Cry1Fa, a Cry1Ia, a Cry1If, a Cry1Ka and/or a Cry1Ca. According to the foregoing embodiments, the chimeric insecticidal protein can optionally have insecticidal activity against a fall armyworm insect pest or colony that has resistance to another insecticidal agent, including another insecticidal protein (such as, e.g., a Bt protein). In embodiments, the chimeric insecticidal protein has insecticidal activity against a fall armyworm colony that is resistant to a Vip3A protein (e.g., a Vip3Aa, including without limitation maize event MIR162) or a Cry1F protein (e.g., Cry1Fa, including without limitation maize event TC1507). In embodiments, the chimeric insecticidal protein has enhanced activity against the resistant fall armyworm colony as compared with one or more of the parent molecules, e.g., BT-0029, BT-0022, a Cry1Fa, a Cry1Ia, a Cry1If, a Cry1Ka and/or a Cry1Ca.

The invention also encompasses antibodies that specifically bind to a chimeric insecticidal protein of the invention. The antibody can optionally be a monoclonal antibody or a polyclonal antisera. In embodiments, the antibody is selective for the chimeric protein and does not bind to one or more of the parent molecules (e.g., BT-0029, BT-0022, Cry1Fa, and the like), and can be used to distinguish the chimeric protein from the parent protein§. Such antibodies may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as described in Harlow and Lane (1988. Antibodies a laboratory manual. pp. 726. Cold Spring Harbor Laboratory) and as in Goding (Monoclonal Antibodies: Principles & practice.1986. Academic Press, Inc., Orlando, Fla.). The present invention also encompasses an insecticidal protein that cross-reacts with an antibody, particularly a monoclonal antibody, raised against one or more of the chimeric insecticidal proteins of the present invention.

The antibodies according to the invention are useful, e.g., in immunoassays for determining the amount or presence of a chimeric insecticidal protein of the invention or an antigenically related polypeptide, e.g., in a biological sample. Such assays are also useful in quality-controlled production of compositions containing one or more of the chimeric insecticidal proteins of the invention or an antigenically related polypeptide. In addition, the antibodies can be used to assess the efficacy of recombinant production of one or more of the chimeric proteins of the invention or an antigenically related polypeptide, as well as for screening expression libraries for the presence of a nucleotide sequence encoding one or more of the chimeric proteins of the invention or an antigenically related polypeptide. Antibodies further find use as affinity ligands for purifying or isolating any one or more of the proteins of the invention or an antigenically related polypeptide.

Nucleic Acids, Expression Cassettes, and Vectors.

As a further aspect, the invention provides nucleic acids encoding the polypeptides of the invention, including modified polypeptides and toxin fragments as described herein.

According to some embodiments, the invention provides a nucleic acid molecule comprising a nucleotide sequence that comprises, consists essentially of, or consists of: (a) a nucleotide sequence encoding the amino acid sequence of SEQ ID NO: 3, SEQ ID NO: 9, SEQ ID NO: 13, SEQ ID NO: 15, SEQ ID NO: 18, SEQ ID Nos: 20-35, or a toxin fragment thereof; (b) a nucleotide sequence encoding an amino acid sequence that is substantially identical to the amino acid sequence of (a); (c) a nucleotide sequence that anneals under stringent hybridization conditions to the nucleotide sequence of (a) or (b); or (d) a nucleotide sequence that differs from the nucleotide sequences of (a), (b) or (c) due to the degeneracy of the genetic code.

In embodiments, the nucleic acid molecule comprises a nucleotide sequence that comprises, consists essentially of, or consists of: (a) a nucleotide sequence of SEQ ID NO: 4, SEQ ID NO: 5, SEQ ID NO: 6, SEQ ID NO: 7, SEQ ID NO: 10, SEQ ID NO: 11, SEQ ID NO:14, or SEQ ID NO: 16, or a toxin-encoding fragment thereof; (b) a nucleotide sequence that is substantially identical to the nucleotide sequence of (a); (c) a nucleotide sequence that anneals under stringent hybridization conditions to the nucleotide sequence of (a) or (b); or (d) a nucleotide sequence that differs from the nucleotide sequences of (a), (b) or (c) due to the degeneracy of the genetic code. Optionally, the nucleotide sequence comprises, consists essentially of, or consists of the nucleotide sequence of SEQ ID NO: 4, SEQ ID NO: 5, SEQ ID NO: 6, SEQ ID NO: 7, SEQ ID NO: 10, SEQ ID NO: 11, SEQ ID NO: 14 or SEQ ID NO: 16.

In embodiments, the nucleotide sequence is a partially or completely synthetic sequence, e.g., that has codons optimized for expression in a host organism, e.g., in a bacterium host or a plant host (for example, a transgenic monocot plant host or a transgenic dicot plant host). Non-limiting examples nucleotide sequences that are codon-optimized for expression in a maize plant include SEQ ID NO: 5, SEQ ID NO: 6, SEQ ID NO: 7 and SEQ ID NO: 11.

In representative embodiments, for expression in transgenic plants, the nucleotide sequences of the invention are modified and/or optimized. For example, although in many cases genes from microbial organisms can be expressed in plants at high levels without modification, low expression in transgenic plants may result from microbial nucleotide sequences having codons that are not preferred in plants. It is known in the art that living organisms have specific preferences for codon usage, and the codons of the nucleotide sequences described in this invention can be changed to conform with plant preferences, while maintaining the amino acids encoded thereby. Furthermore, it is known in the art that high expression in plants, for example corn plants, can be achieved from coding sequences that have at least about 35% GC content, or at least about 45%, or at least about 50%, or at least about 60%. Microbial nucleotide sequences that have low GC contents may express poorly in plants. Although certain nucleotide sequences can be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, in embodiments, the nucleotide sequence is modified to remove illegitimate splice sites that may cause message truncation. Such modifications to the nucleotide sequences can be made using well known techniques of site directed mutagenesis, PCR, and synthetic gene construction using the methods described, for example, in U.S. Pat. Nos. 5,625,136; 5,500,365 and 6,013,523.

In some embodiments, the invention provides synthetic coding sequences or polynucleotide made according to the procedure disclosed in U.S. Pat. No. 5,625,136. In this procedure, maize preferred codons, i.e., the single codon that most frequently encodes that amino acid in maize, are used. The maize preferred codon for a particular amino acid can be derived, for example, from known gene sequences from maize. For example, maize codon usage for 28 genes from maize plants is found in Murray et al., Nucleic Acids Research 17:477-498 (1989). It is recognized that codons optimized for expression in one plant species will also function in other plant species but possibly not at the same level as the plant species for which the codons were optimized. In this manner, the nucleotide sequences can be optimized for expression in any plant. It is recognized that all or any part of a nucleotide sequence may be optimized or synthetic. That is, a polynucleotide may comprise a nucleotide sequence that is part native sequence and part codon optimized sequence.

In representative embodiments, a polynucleotide of the invention is an isolated polynucleotide. In embodiments, a polynucleotide of the invention is a recombinant polynucleotide.

In embodiments, the invention further provides a nucleic acid molecule comprising a polynucleotide of the operably associated with a promoter (e.g., a heterologous promoter). Promoters can include, for example, constitutive, inducible, temporally regulated, developmentally regulated, chemically regulated, tissue-preferred and/or tissue-specific promoters. In particular aspects, a promoter useful with the invention is a promoter capable of initiating transcription of a nucleotide sequence in a plant cell, e.g., in a cell of a monocot (e.g., maize or rice) or dicot (e.g., soybean, cotton) plant.

In embodiments, a heterologous promoter is a plant-expressible promoter (e.g., monocot expressible or dicot expressible). For example, without limitation, the plant-expressible promoter can be selected from the following promoters: ubiquitin, cestrum yellow virus, corn TrpA, OsMADS 6, maize H3 histone, bacteriophage T3 gene 9 5' UTR, corn sucrose synthetase 1, corn alcohol dehydrogenase 1, corn light harvesting complex, corn heat shock protein, maize mtl, pea small subunit RuBP carboxylase, rice actin, rice cyclophilin, Ti plasmid mannopine synthase, Ti plasmid nopaline synthase, petunia chalcone isomerase, bean glycine rich protein 1, potato patatin, lectin, CaMV 35S and S-E9 small subunit RuBP carboxylase promoter.

Although many promoters from dicotyledons have been shown to be operational in monocotyledons and vice versa, in embodiments, dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

The choice of promoter can vary depending on the temporal and spatial requirements for expression, and also depending on the host cell to be transformed. Thus, for example, expression of the nucleotide sequences of the invention can be in any plant and/or plant part, (e.g., in leaves, in stalks or stems, in ears, in inflorescences (e.g., spikes, panicles, cobs, etc.), in roots, seeds and/or seedlings, and the like). For example, where expression in a specific tissue or organ is desired, a tissue-specific or tissue-preferred promoter can be used (e.g., a root specific/preferred promoter). In contrast, where expression in response to a stimulus is desired a promoter inducible by stimuli or chemicals can be used. Where continuous expression at a relatively constant level is desired throughout the cells of a plant a constitutive promoter can be chosen.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

Suitable constitutive promoters include, for example, CaMV 35S promoter (Odell et al., Nature 313:810-812, 1985); *Arabidopsis* At6669 promoter (see PCT Publication No. WO04081173A2); maize Ubi 1 (Christensen et al., Plant Mol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol Biol. 25(5):837-43, 1994); Maize H3 histone (Lepetit et al., Mol. Gen. Genet. 231: 276-285, 1992); Actin 2 (An et al., Plant J. 10(1); 107-121, 1996), constitutive root tip CT2 promoter (SEQ ID NO:1535; see also PCT application No. IL/2005/000627) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Tissue-specific or tissue-preferential promoters useful for the expression of the polypeptides of the invention in plants, optionally maize, include those that direct expression in root, pith, leaf or pollen. Suitable tissue-specific promoters include, but not limited to, leaf-specific promoters (such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993), seed-preferred promoters (e.g., from seed specific genes; Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson et al., Plant Mol.

Biol. 18: 235-245, 1992), legumin (Ellis, et al. Plant Mol. Biol. 10: 203-214, 1988), Glutelin (Takaiwa, et al., Mol. Gen. Genet. 208: 15-22, 1986; Takaiwa, et al., FEBS Letts. 221: 43-47, 1987), Zein (Matzke et al., Plant Mol Biol, 143).323-32 1990), napA (Stalberg, et al., Planta 199: 515-519, 1996), Wheat SPA (Albani et al, Plant Cell, 9: 171-184, 1997), sunflower oleosin (Cummins, et al., Plant Mol. Biol. 19: 873-876, 1992)], endosperm specific promoters (e.g., wheat LMW and HMW, glutenin-1 (Mol Gen Genet 216: 81-90, 1989; NAR 17:461-2), wheat a, b and g gliadins (EMB03:1409-15, 1984), Barley Itr1 promoter, barley B1, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (Plant Mol. Biol 32:1029-35, 1996)], embryo specific promoters (e.g., rice OSH1; Sato et al., Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)] flower-specific promoters, for example, AtPRP4, chalene synthase (chsA) (Van der Meer, et al., Plant Mol. Biol. 15, 95-109, 1990), LAT52 (Twell et al., Mol. Gen Genet. 217:240-245; 1989), apetala-3, and promoters specific for plant reproductive tissues (e.g., OsMADS promoters; U.S. Patent Publication 2007/0006344).

Examples of promoters suitable for preferential expression in green tissue include many that regulate genes involved in photosynthesis and many of these have been cloned from both monocotyledons and dicotyledons. One such promoter is the maize PEPC promoter from the phosphoenol carboxylase gene (Hudspeth & Grula, Plant Molec. Biol. 12:579-589 (1989)). Another promoter for root specific expression is that described by de Framond (FEBS 290:103-106 (1991) or U.S. Pat. No. 5,466,785). Another promoter useful in the invention is the stem specific promoter described in U.S. Pat. No. 5,625,136, which naturally drives expression of a maize trpA gene.

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in a plant through the application of an exogenous chemical regulator. Regulation of the expression of nucleotide sequences of the invention via promoters that are chemically regulated enables the polypeptides of the invention to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression. Examples of such technology for chemical induction of gene expression is detailed in published application EP 0 332 104 and U.S. Pat. No. 5,614,395.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Intl Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108. Other chemically inducible promoters useful for directing the expression of the nucleotide sequences of this invention in plants are disclosed in U.S. Pat. No. 5,614,395. Chemical induction of gene expression is also detailed in EP 0 332 104 (to Ciba-Geigy) and U.S. Pat. No. 5,614,395.

Another category of promoters useful in the invention are wound inducible promoters. Numerous promoters have been described that are expressed at wound sites and also at the sites of phytopathogen infection. Ideally, such a promoter should only be active locally at the sites of insect invasion, and in this way the insecticidal proteins only accumulate in cells that need to synthesize the insecticidal proteins to kill the invading insect pest. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

In embodiments a nucleic acid of the invention can comprise, consist essentially of, or consist of an expression cassette, or can be comprised within an expression cassette.

An expression cassette comprising a polynucleotide of interest may be chimeric, meaning that at least one of its components is heterologous with respect to at least one other of its other components. An expression cassette may also be one that is naturally occurring but has been obtained in a recombinant form useful for heterologous expression. Typically, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively associated with the nucleotide sequences of the invention, an expression cassette of this invention can also include other regulatory elements. Regulatory elements include, but are not limited to, enhancers, introns, translation leader sequences, termination signals, and polyadenylation signal sequences. Examples of suitable transcription terminator signals are available and known in the art (e.g., tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g., from AdhI and bronzeI) and viral leader sequences (e.g., from TMV, MCMV and AMV).

For more efficient initiation of translation, sequences adjacent to the initiating methionine may be modified. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (while leaving the second amino acid unmodified), or alternatively up to and including the GTC subsequent to the ATG (with the possibility of modifying the second amino acid of the transgene).

In embodiments, it may be desired to target expression of the polypeptides of the present invention to a specific cellular location in the plant cell. In some cases, localization in the cytosol may be desirable, whereas in other cases, localization in some subcellular organelle may be preferred. Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments. For example, amino terminal sequences can be responsible for targeting a protein of interest to a cell compartment, such as, a vacuole, mitochondrion, peroxisome, protein bodies, endoplasmic reticulum, chloroplast, starch granule, amyloplast, apoplast or cell wall of a plant cell (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704. Optionally, the signal sequence may be an N-terminal signal sequence from waxy, an N-terminal signal sequence from gamma-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxyl terminal sequences are responsible for vacuolar targeting of gene products and can be used with the present invention (Shinshi et. al. (1990) Plant Molec. Biol. 14: 357-368). In one embodiment, the signal sequence selected includes the known cleavage site, and the fusion constructed takes into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

It will be recognized that the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

An expression cassette of the invention also can include a nucleotide sequence for a selectable marker, which can be used to select a transformed plant, plant part and/or plant cell. Many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) Mol. Gen. Genet. 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) Biotech. 6:915-922); a nucleotide sequence encoding a nitrilase such as bxn from *Klebsiella ozaenae* that confers resistance to bromoxynil (Stalker et al. (1988) Science 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) J. Biol. Chem. 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: Chromosome Structure and Function: Impact of New Concepts, 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) Proc. Natl. Acad. Sci. USA 75:3737-3741); a nucleotide sequence encoding xylE that encodes a catechol dioxygenase (Zukowsky et al. (1983) Proc. Natl. Acad. Sci. USA 80:1101-1105); a nucleotide sequence encoding tyrosinase, an enzyme capable of oxidizing tyrosine to DOPA and dopaquinone, which in turn condenses to form melanin (Katz et al. (1983) J. Gen. Microbiol. 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) Science 234:856-859); a nucleotide sequence encoding aequorin which may be employed in calcium-sensitive bioluminescence detection (Prasher et al. (1985) Biochem. Biophys. Res. Comm. 126:1259-1268); or a nucleotide sequence encoding green fluorescent protein (Niedz et al. (1995) Plant Cell Reports 14:403-406). One of skill in the art can choose a suitable selectable marker for use in an expression cassette of this invention.

In some embodiments, an expression cassette of the invention also can include polynucleotides that encode other desired traits in addition to the chimeric insecticidal proteins of the invention. Examples of such other polynucleotides include that those encode a polypeptide or a dsRNA for the other desired trait(s) of interest. Such expression cassettes comprising the "stacked" traits may be used, e.g., to create plants, plant parts or plant cells having a desired phenotype with the stacked traits (i.e., molecular stacking). Such stacked combinations in plants can also be created by other methods including, but not limited to, cross breeding plants by any conventional methodology (i.e., a breeding stack). If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, or composition of this invention, provided by any combination of expression cassettes. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific recombination system. See, e.g., Intl Patent Application Publication Nos. WO 99/25821; WO 99/25854; WO 99/25840; WO 99/25855 and WO 99/25853.

In representative embodiments, the expression cassette can also include an additional coding sequence for one or more polypeptides or double stranded RNA molecules (dsRNA) of interest for an agronomic trait (e.g., an agronomic trait that is primarily of benefit to a seed company, grower or grain processor). A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. In embodiments, the polypeptide of interest can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810, 648; 4,940,835; 4,975,374; 5,013,659; 5,162,602; 5,276, 268; 5,304,730; 5,495,071; 5,554,798; 5,561,236; 5,569, 823; 5,767,366; 5,879,903, 5,928,937; 6,084,155; 6,329,504 and 6,337,431; as well as US Patent Publication No. 2001/ 0016956. See also, on the World Wide Web at lifesci.sussex.ac.uk/home/Neil_Crickmore/Bt/.

Polynucleotides conferring resistance/tolerance to an herbicide that inhibits the growing point or meristem, such as an imidazalinone or a sulfonylurea can also be suitable in some embodiments of the invention. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase). See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for pesticidal (e.g., insecticidal) polypeptides. These polypeptides may be produced in amounts sufficient to control, for example, insect pests (i.e., insect controlling amounts). In embodiments, the polypeptide is a lepidopteran-active, coleopteran-active, hemipteran-active and/or dipteran-active polypeptide, or any combination thereof. It is recognized that the amount of production of a pesticidal polypeptide in a plant necessary to control insects or other pests may vary depending upon the cultivar, type of pest, environmental factors and the like. Polynucleotides useful for additional insect or pest resistance include, for example, those that encode toxins identified in *Bacillus* organisms. Polynucleotides comprising nucleotide sequences encoding *Bacillus thuringiensis* (Bt) Cry proteins from several subspecies have been cloned and recombinant clones have been found to be toxic to lepidopteran, dipteran and coleopteran insect larvae. Examples of such Bt insecticidal proteins include the Cry proteins such as Cry1Aa, Cry1Ab, Cry1Ac, Cry1B, Cry1C, Cry1D, Cry1Ea, Cry1Fa, Cry3A, Cry9A, Cry9B, Cry9C, and the like, as well as vegetative insecticidal proteins such as Vip1, Vip2, Vip3, and the like, and any combination of the foregoing Bt insecticidal proteins. A full list of Bt-derived proteins can be found on the worldwide web at *Bacillus thuringiensis* Toxin Nomenclature Database maintained by the University of Sussex (see also, Crickmore et al. (1998) Microbiol. Mol. Biol. Rev. 62:807-813).

In embodiments, an additional polypeptide is an insecticidal polypeptide derived from a non-Bt source, including without limitation, an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin.

Polypeptides that are suitable for production in plants further include those that improve or otherwise facilitate the conversion of harvested plants or plant parts into a commercially useful product, including, for example, increased or altered carbohydrate content or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In some embodiments, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) Foundation for Biotechnical and Industrial Fermentation Research 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) Enzyme Microb. Technol. 14:566; Torronen et al. (1992) Bio/Technology 10:1461; and Xu et al. (1998) Appl. Microbiol. Biotechnol.

In other embodiments, a polypeptide useful for the invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as alpha-amylases (EC 3.2.1.1), glucuronidases (E.C. 3.2.1.131); exo-1,4-alpha-D glucanases such as amyloglucosidases and glucoamylase (EC 3.2.1.3), beta-amylases (EC 3.2.1.2), alpha-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-beta-D-glucanase (EC 3.2.1.39), beta-glucosidase (EC 3.2.1.21); c) L-arabinases, such as endo-1,5-alpha-L-arabinase (EC 3.2.1.99), alpha-arabinosidases (EC 3.2.1.55) and the like; d) galactanases such as endo-1,4-beta-D-galactanase (EC 3.2.1.89), endo-1,3-beta-D-galactanase (EC 3.2.1.90), alpha-galactosidase (EC 3.2.1.22), beta-galactosidase (EC 3.2.1.23) and the like; e) mannanases, such as endo-1,4-beta-D-mannanase (EC 3.2.1.78), beta-mannosidase (EC 3.2.1.25), alpha-mannosidase (EC 3.2.1.24) and the like; f) xylanases, such as endo-1,4-beta-xylanase (EC 3.2.1.8), beta-D-xylosidase (EC 3.2.1.37), 1,3-beta-D-xylanase, and the like; and g) other enzymes such as alpha-L-fucosidase (EC 3.2.1.51), alpha-L-rhamnosidase (EC 3.2.1.40), levanase (EC 3.2.1.65), inulanase (EC 3.2.1.7), and the like. In one embodiment, the alpha-amylase is the synthetic alpha-amylase, Amy797E, described is U.S. Pat. No. 8,093,453.

Further enzymes which may be used with the invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes useful with the invention include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g., E.C. 3.1.1.74).

Double stranded RNA (dsRNA) molecules useful with the invention include, but are not limited to those that suppress target pest (e.g., insect) genes. In embodiments, the dsRNA targets a gene in a lepidopteran, coleopteran, hemipteran or dipteran insect pest, or any combination of the foregoing. As used herein the words "gene suppression", when taken together, are intended to refer to any of the well-known methods for reducing the levels of protein produced as a result of gene transcription to mRNA and subsequent translation of the mRNA. Gene suppression is also intended to mean the reduction of protein expression from a gene or a coding sequence including posttranscriptional gene suppression and transcriptional suppression. Posttranscriptional gene suppression is mediated by the homology between all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi). Transcriptional suppression is mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant pests that may ingest or contact plant material containing gene suppression agents, specifically designed to inhibit or suppress the expression of one or more homologous or complementary sequences in the cells of the pest. Such genes targeted for suppression can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis.

In embodiments, the nucleic acids of the invention can further comprise, consist essentially of, or consist of a vector. In embodiments, the polynucleotides and expression cassettes of the invention are comprised within a vector. Vectors for use in transformation of plants and other organisms are well known in the art. Non-limiting examples of general classes of vectors include a plasmid, phage vector, phagemid vector, cosmid vector, fosmid, bacteriophage, artificial chromosome, or a viral vector. In embodiments, the vector is plant vector, e.g., for use in transformation of plants. In embodiments, the vector is a bacterial vector, e.g., for use in transformation of bacteria. Suitable vectors for plants, bacteria and other organisms are known in the art.
Transgenic Plants, Plant Parts, Plant Cells, Seed.

The invention also encompasses a transgenic non-human host cell comprising a polynucleotide, a nucleic acid molecule, an expression cassette, a vector, or a polypeptide of the invention. The transgenic non-human host cell can include, but is not limited to, a plant cell (including a monocot cell and/or a dicot cell), a yeast cell, a bacterial cell or an insect cell. Accordingly, in some embodiments, the invention provides a bacterial cell selected from the genera *Bacillus, Brevibacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthrobacter, Azotobacter, Leuconostoc,* or *Alcaligenes.* Thus, for example, as biological insect control agents, the chimeric insecticidal proteins of the invention can be produced by expression of a polynucleotide encoding the same in a bacterial cell. For example, in some embodiments, a *Bacillus thuringiensis* cell comprising a polynucleotide encoding a chimeric insecticidal protein of the invention is provided.

In embodiments, the transgenic plant cell is a dicot plant cell or a monocot plant cell. In additional embodiments, the dicot plant cell is a soybean cell, sunflower cell, tomato cell, cole crop cell, cotton cell, sugar beet cell or a tobacco cell. In further embodiments, the monocot cell is a barley cell, maize cell, oat cell, rice cell, sorghum cell, sugar cane cell or wheat cell. In embodiments, the invention provides a plurality of dicot cells or monocot cells comprising a polynucleotide expressing a chimeric insecticidal protein of the invention. In embodiments, the plurality of cells are juxtaposed to form an apoplast and are grown in natural sunlight. In embodiments, the transgenic plant cell cannot regenerate a whole plant.

In embodiments of the invention, an insecticidal protein of the invention is expressed in a higher organism, for example, a plant. In this case, transgenic plants expressing effective amounts of the insecticidal protein protect themselves from plant pests such as insect pests. When an insect starts feeding on such a transgenic plant, it ingests the expressed insecticidal protein. This can deter the insect from further biting into the plant tissue or may even harm or kill the insect. In embodiments, a polynucleotide of the invention is inserted into an expression cassette, which is then stably integrated in the genome of the plant. In other embodiments, the polynucleotide is included in a non-pathogenic self-replicating virus.

In some embodiments of the invention, a transgenic plant cell comprising a nucleic acid molecule or polypeptide of the invention is a cell of a plant part, a plant organ or a plant culture (each as described herein) including, but not limited to, a root, a leaf, a seed, a flower, a fruit, a pollen cell, organ or plant culture, and the like, or a callus cell or culture.

A transgenic plant or plant cell in accordance with the invention may be a monocot or dicot plant or plant cell and includes, but is not limited to, corn (maize), soybean, rice, wheat, barley, rye, oat, sorghum, millet, sunflower, safflower, sugar beet, cotton, sugarcane, oilseed rape, alfalfa, tobacco, peanut, vegetable (including, sweet potato, bean, pea, chicory, lettuce, cabbage, cauliflower, broccoli, turnip, carrot, eggplant, cucumber, radish, spinach, potato, tomato, asparagus, onion, garlic, melon, pepper, celery, squash, pumpkin, zucchini, and the like), fruit (including, apple, pear, quince, plum, cherry, peach, nectarine, apricot, strawberry, grape, raspberry, blackberry, pineapple, avocado, papaya, mango, banana, and the like), a specialty plant or plant cell (such as *Arabidopsis*), or a woody plant or plant cell (such as coniferous and/or deciduous trees). In embodiments, a plant or plant cell of the of the invention is a crop plant or plant cell such as maize, sorghum, wheat, sunflower, tomato, a crucifer, pepper, potato, cotton, rice, soybean, sugar beet, sugarcane, tobacco, barley, oilseed rape plant or plant cell, and the like.

The invention further provides a part of a transgenic plant of the invention. Optionally, the plant part comprises a chimeric insecticidal protein of the invention and/or a nucleic acid encoding the same.

The invention further provides a seed of a transgenic plant of the invention or a seed that produces the transgenic plant of the invention. Optionally, the seed comprises a chimeric insecticidal protein of the invention and/or a nucleic acid encoding the same.

Additional embodiments of the invention include harvested products produced from the transgenic plants, plant parts or seed of the invention, as well as a processed product produced from a harvested product. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, cereal, and the like produced from a harvested seed or other plant part of the invention. Optionally, the harvested product or the processed product comprises a chimeric insecticidal protein of the invention and/or a nucleic acid encoding the same.

In other embodiments, the invention provides an extract from a transgenic plant, plant part or of the invention, optionally wherein the extract comprises a chimeric insecticidal protein of the invention and/or a nucleic acid encoding the same. Extracts from plants or plant parts can be made according to procedures well known in the art (See, de la Torre et al., Food, Agric. Environ. 2(1):84-89 (2004); Guidet, Nucleic Acids Res. 22(9): 1772-1773 (1994); Lipton et al., Food Agric. Immun. 12:153-164 (2000)).

The chimeric insecticidal protein in the plant part, plant cell, plant organ, seed, harvested product, processed product or extract, and the like, as an insect control agent. In other words, the chimeric insecticidal protein can continue to perform the insecticidal function it had in the transgenic plant. The nucleic acid can function to express the chimeric insecticidal protein. As an alternative to encoding the insecticidal protein of the invention, the nucleic acid can function to identify a transgenic plant part, plant cell, plant organ, seed, harvested product, processed product or extract of the invention.

In embodiments, a transgenic plant, plant part, plant cell, plant organ, or seed of the invention is hemizygous for a polynucleotide or expression cassette of the invention. In embodiments, a transgenic plant, plant part, plant cell, plant organ, or seed of the invention is homozygous for a polynucleotide or expression cassette of the invention.

In embodiments, a transgenic plant, plant part, plant cell, plant organ, seed, harvested product, processed product or extract has increased resistance to one or more insect pests (e.g., a lepidopteran pest, such as fall armyworm) as compared with a suitable control that does not comprise a nucleic acid encoding an insecticidal protein of the invention.

Plant Transformation.

Procedures for transforming plants are well known and routine in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (Cell. Mol. Biol. Lett. 7:849-858 (2002)).

For *Agrobacterium*-mediated transformation, binary vectors or vectors carrying at least one T-DNA border sequence are generally suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., Biotechnology 4:1093-1096 (1986)). For both direct gene transfer and *Agrobacterium*-mediated transfer, transformation is usually (but not necessarily) undertaken with a selectable marker that may be a positive selection (e.g., Phosphomannose Isomerase), provide resistance to an antibiotic (e.g., kanamycin, hygromycin or methotrexate) or a herbicide (e.g., glyphosate or glufosinate). However, the choice of selectable marker is not critical to the invention.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) Plant Cell 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) Nucleic Acids Res. 16:9877).

Dicots as well as monocots may be transformed using *Agrobacterium*. Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an Agrobacterial solution and then culturing them in suitable media. The transformation of plants by means of *Agrobacterium tumefaciens* is described, for example, by Hagen and Willmitzer in Nucl.

Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In other embodiments, a polynucleotide of the invention can be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545, 818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin or streptomycin can be utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). The presence of cloning sites between these markers allows creation of a plastid targeting vector for introduction of foreign genes (Staub, J. M., and Maliga, P. (1993) EMBO J. 12, 601-606). Substantial increases in transformation frequency can be obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells or plant tissue culture are routine in the art and can be employed in the methods of the invention provided herein. For example, a recombinant vector of the invention also can include an expression cassette comprising a nucleotide sequence for a selectable marker, which can be used to select a transformed plant, plant part or plant cell.

Further, as is well known in the art, intact transgenic plants can be regenerated from transformed plant cells, plant tissue culture or cultured protoplasts using any of a variety of known techniques. Plant regeneration from plant cells, plant tissue culture or cultured protoplasts is described, for example, in Evans et al. (Handbook of Plant Cell Cultures, Vol. 1, MacMilan Publishing Co. New York (1983)); and Vasil I. R. (ed.) (Cell Culture and Somatic Cell Genetics of Plants, Acad. Press, Orlando, Vol. I (1984), and Vol. II (1986)).

Additionally, the genetic properties engineered into the transgenic seeds and plants, plant parts, or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into the plant, plant part or plant cell in any number of ways that are well known in the art, as described above. Therefore, no particular method for introducing one or more polynucleotides into a plant is relied upon, rather any method that allows the one or more polynucleotides to be stably integrated into the genome of the plant can be used. Where more than one polynucleotides is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Once a desired polynucleotide has been transformed into a particular plant species, it may be propagated in that species or moved into other varieties of the same species, particularly including commercial varieties, using traditional breeding techniques.

Insecticidal Compositions.

In some embodiments, the invention provides an insecticidal composition comprising a chimeric insecticidal protein of the invention in an agriculturally acceptable carrier. As used herein an "agriculturally-acceptable carrier" can include natural or synthetic, organic or inorganic material which is combined with the active protein to facilitate its application to or in the plant, or part thereof. Examples of agriculturally acceptable carriers include, without limitation, powders, dusts, pellets, granules, sprays, emulsions, colloids, and solutions. Agriculturally-acceptable carriers further include, but are not limited to, inert components, dispersants, surfactants, adjuvants, tackifiers, stickers, binders, or combinations thereof, that can be used in agricultural formulations. Such compositions can be applied in any manner that brings the pesticidal proteins or other pest control agents in contact with the pests. Accordingly, the compositions can be applied to the surfaces of plants or plant parts, including seeds, leaves, flowers, stems, tubers, roots, and the like. In other embodiments, a plant producing an insecticidal protein of the invention in planta is an agriculturally-acceptable carrier of the expressed insecticidal protein. In embodiments, the compositions and agriculturally-acceptable carriers of the invention exclude transgenic plants.

In further embodiments, the insecticidal composition comprises a bacterial cell or a transgenic bacterial cell of the invention, wherein the bacterial cell or transgenic bacterial cell produces an insecticidal protein of the invention. Such an insecticidal composition can be prepared by desiccation, lyophilization, homogenization, extraction, filtration, centrifugation, sedimentation, or concentration of a culture of *Bacillus thuringiensis* (Bt), including a transgenic Bt culture. In embodiments, a composition of the invention may comprise at least about 1%, at least about 5%, at least about 10%, at least about 20%, at least about 25%, at least about 30%, at least about 35%, at least about 40%, at least about 50%, at least about 60%, at least about 70%, at least about 80%, at least about 90%, at least about 95%, at least about 97%, or at least 99% by weight a polypeptide of the invention. In additional embodiments, the composition comprises from about 1% to about 99% by weight of the insecticidal protein of the invention.

The insecticidal proteins of the invention can be used in combination with other pest control agents to increase pest target spectrum and/or for the prevention or management of insect resistance. Furthermore, the use of the insecticidal proteins of the invention in combination with an insecticidal agent which has a different mode of action or target a different receptor in the insect gut has particular utility for the prevention and/or management of insect resistance.

Therefore, in some embodiments, the invention provides a composition that controls one or more plant pests (e.g., an insect pest such as a lepidopteran insect pest, a coleopteran insect pest, a hemipteran insect pest and/or a dipteran insect pest), wherein the composition comprises a first pest control agent, which is a chimeric insecticidal protein of the invention and at least a second pest control agent that is different from the first pest control agent. In other embodiments, the composition is a formulation for topical application to a plant. In still other embodiments, the composition is a transgenic plant. In further embodiments, the composition is a combination of a formulation topically applied to a transgenic plant. In some embodiments, the formulation comprises the first pest control agent, which is a chimeric insecticidal protein of the invention when the transgenic plant comprises the second pest control agent. In other embodiments, the formulation comprises the second pest control agent when the transgenic plant comprises the first pest control agent, which is a chimeric insecticidal protein of the invention.

In some embodiments, the second pest control agent can be one or more of a chemical pesticide, such as an insecticide, a *Bacillus thuringiensis* (Bt) insecticidal protein, and/or a non-Bt pesticidal agent including without limitation a *Xenorhabdus* insecticidal protein, a *Photorhabdus* insecticidal protein, a *Brevibacillus laterosporus* insecticidal protein, a *Bacillus sphaericus* insecticidal protein, a protease inhibitor (both serine and cysteine types), a lectin, an alpha-amylase, a peroxidase, a cholesterol oxidase, or a double stranded RNA (dsRNA) molecule.

In other embodiments, the second pest control agent is one or more chemical pesticides, which is optionally a seed coating. Non-limiting examples of chemical pesticides include pyrethroids, carbamates, neonicotinoids, neuronal sodium channel blockers, insecticidal macrocyclic lactones, gamma-aminobutyric acid (GABA) antagonists, insecticidal ureas and juvenile hormone mimics. In other embodiments, the chemical pesticide is one or more of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. In still other embodiments, the chemical pesticide is selected from one or more of cypermethrin, cyhalothrin, cyfluthrin and beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, endosulfan, ethiprole, fipronil, flufenoxuron, triflumuron, diofenolan, pyriproxyfen, pymetrozine and amitraz.

In additional embodiments, the second pest control agent can be one or more of any number of *Bacillus thuringiensis* insecticidal proteins including but not limited to a Cry protein, a vegetative insecticidal protein (VIP) and insecticidal chimeras of any of the preceding insecticidal proteins. In other embodiments, the second pest control agent is a Cry protein selected from: Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1Cb, Cry1Da, Cry1Db, Cry1Dc, Cry1Dd, Cry1Ea, Cry1Eb, Cry1Fa, Cry1Fb, Cry1Ga, Cry1Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1Jb, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2Al, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5 Da, Cry5Ea, Cry6Aa, Cry6Ba, Cry7Aa, Cry7Ab, Cry7Ac, Cry7Ba, Cry7Bb, Cry7Ca, Cry7Cb, Cry7 Da, Cry7Ea, Cry7Fa, Cry7Fb, Cry7Ga, Cry7Gb, Cry7Gc, Cry7Gd, Cry7Ha, Cry7Ia, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8 Da, Cry8db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8 Pa, Cry8Qa, Cry8Ra, Cry8Sa, Cry8Ta, Cry9Aa, Cry9Ba, Cry9Bb, Cry9Ca, Cry9 Da, Cry9db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21Ba, Cry21Ca, Cry21Da, Cry21Ea, Cry21Fa, Cry21Ga, Cry21Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30 Da, Cry30db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32 Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32 Mb, Cry32Na, Cry32Oa, Cry32 Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40 Da, Cry41Aa, Cry41Ab, Cry41Ba, Cry42Aa, Cry43Aa, Cry43Ba, Cry43Ca, Cry43Cb, Cry43Cc, Cry44Aa, Cry45Aa, Cry46Aa Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa, Cry73Aa, or any combination of the foregoing. In embodiments, the Cry protein is a Cry1Fa, for example, as represented by maize event TC1507.

In further embodiments, the second pest control agent is one or more Vip3 vegetative insecticidal proteins selected from Vip3Aa1, Vip3Aa2, Vip3Aa3, Vip3Aa4, Vip3Aa5, Vip3Aa6, Vip3Aa7, Vip3Aa8, Vip3Aa9, Vip3Aa10, Vip3Aa11, Vip3Aa12, Vip3Aa13, Vip3Aa14, Vip3Aa15, Vip3Aa16, Vip3Aa17, Vip3Aa18, Vip3Aa19, Vip3Aa20, Vip3Aa21, Vip3Aa22, Vip3Aa2, Vip3Aa24, Vip3Aa25, Vip3Aa26, Vip3Aa27, Vip3Aa28, Vip3Aa29, Vip3Aa30, Vip3Aa31, Vip3Aa32, Vip3Aa33, Vip3Aa34, Vip3Aa35, Vip3Aa36, Vip3Aa37, Vip3Aa38, Vip3Aa39, Vip3Aa40, Vip3Aa41, Vip3Aa42, Vip3Aa43, Vip3Aa44, Vip3Ab1, Vip3Ab2, Vip3Ac1, Vip3Ad1, Vip3Ad2, Vip3Ae1, Vip3Af1, Vip3Af2, Vip3Af3, Vip3Ag1, Vip3Ag2, Vip3Ag3 HM117633, Vip3Ag4, Vip3Ag5, Vip3Ah1, Vip3Ba1, Vip3Ba2, Vip3Bb1, Vip3Bb2, Vip3Bb3, or any combination of the foregoing. In embodiments, the Vip3 protein is Vip3Aa (U.S. Pat. No. 6,137,033), for example, as represented by corn event MIR162 (U.S. Pat. Nos. 8,232,456; 8,455,720; and 8,618,272).

In embodiments, the second pest control agent may be derived from sources other than *B. thuringiensis*. For example, the second pest control agent can be an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin. In other embodiments, the second agent may be at least one insecticidal protein derived from an insecticidal toxin complex (Tc) from *Photorhabdus, Xenorhabus, Serratia*, or *Yersinia*. In other embodiments. The insecticidal protein may be an ADP-ribosyltransferase derived from an insecticidal bacteria, such as *Photorhabdus* ssp. In other embodiments, the insecticidal protein may be a VIP protein, such as VIP1 and/or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In some embodiments, the second pesticidal agent can be non-proteinaceous, for example, an interfering RNA molecule such as a dsRNA, which can be expressed transgenically or applied as part of a composition (e.g., using topical methods). An interfering RNA typically comprises at least a RNA fragment against a target gene, a spacer sequence, and a second RNA fragment which is complementary to the first, so that a double-stranded RNA structure can be formed. RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Interfering RNAs are known in the art to be useful for insect control (see, for example, publication WO2013/192256, incorporated by reference herein). An interfering RNA designed for use in insect control produces a non-naturally occurring double-stranded RNA, which takes advantage of the native RNAi pathways in the insect to trigger down-regulation of target genes that may lead to the cessation of feeding and/or growth and may result in the death of the insect pest. The interfering RNA molecule may confer insect resistance against the same target pest as the protein of the invention, or may target a different pest. The targeted insect plant pest may feed by chewing, sucking, or piercing. Interfering RNAs are known in the art to be useful for insect control. In embodiments, the dsRNA useful for insect control is described in US Patent Application Publication Nos. 20190185526, 20190177736, or 20180200281, filed on Aug. 5, 2016. In embodiments, the dsRNA useful for insect control is described in U.S. Pat. No. 9,238,8223, 9,340,797, or 8,946,510. In embodiments, the dsRNA useful for insect control is described in US Patent Application Publication Nos. 20110054007, 20140275208, 20160230185, or 2016230186. In other embodiments, the interfering RNA may confer resistance against a non-insect plant pest, such as a nematode pest or a virus pest.

In still further embodiments, the first insect control agent, which is a chimeric insecticidal protein of the invention and the second pest control agent are co-expressed in a transgenic plant. This co-expression of more than one pesticidal principle in the same transgenic plant can be achieved by genetically engineering a plant to contain and express the nucleic acid sequences encoding the insect control agents. For example, the co-expression of more than one pesticidal agent in the same transgenic plant can be achieved by making a single recombinant vector comprising coding sequences of more than one pesticidal agent in a "molecular stack" and genetically engineering a plant to contain and express all the pesticidal agents in the transgenic plant. Such molecular stacks may be also be made by using minichromosomes as described, for example in U.S. Pat. No. 7,235,716. Alternatively, a plant, Parent 1, can be genetically engineered for the expression of the chimeric insecticidal protein of the invention. A second plant, Parent 2, can be genetically engineered for the expression of a second pest control agent. By crossing Parent 1 with Parent 2, progeny plants are obtained which express both insect control agents from Parents 1 and 2.

In other embodiments, the invention provides a stacked transgenic plant resistant to plant pest infestation comprising a nucleic acid (e.g., DNA) sequence encoding a dsRNA for suppression of an essential gene in a target pest and a nucleic acid e.g., (DNA) sequence encoding a chimeric insecticidal protein of the invention exhibiting insecticidal activity against the target pest. It has been reported that dsRNAs are ineffective against certain lepidopteran pests (Rajagopol et al. 2002. J. Biol. Chem. 277:468-494), likely due to the high pH of the midgut which destabilizes the dsRNA. Therefore, in some embodiments where the target pest is a lepidopteran pest, a chimeric insecticidal protein of the invention acts to transiently reduce the midgut pH which serves to stabilize the co-ingested dsRNA rendering the dsRNA effective in silencing the target genes.

Transgenic plants or seed comprising and/or expressing an insecticidal protein of the invention can also be treated with an insecticide or insecticidal seed coating as described in U.S. Pat. Nos. 5,849,320 and 5,876,739. In embodiments, where both the insecticide or insecticidal seed coating and the transgenic plant or seed of the invention are active against the same target insect, for example a lepidopteran pest (e.g., fall armyworm), the combination is useful (i) in a method for further enhancing activity of the composition of the invention against the target insect, and/or (ii) in a method for preventing development of resistance to the composition of the invention by providing yet another mechanism of action against the target insect. Thus, in embodiments, the invention provides a method of enhancing control of a lepidopteran insect population comprising providing a transgenic plant or seed of the invention and applying to the plant or the seed an insecticide or insecticidal seed coating to a transgenic plant or seed of the invention.

Even where the insecticide or insecticidal seed coating is active against a different insect, the insecticide or insecticidal seed coating is useful to expand the range of insect control, for example by adding an insecticide or insecticidal seed coating that has activity against coleopteran insects to a transgenic seed of the invention, which, in some embodiments, has activity against lepidopteran insects, the coated transgenic seed produced controls both lepidopteran and coleopteran insect pests.

Methods of Making and Using the Chimeric Insecticidal Proteins, Nucleic Acids, and Transgenic Plants.

The invention also encompasses methods of producing an insect-resistant (e.g., a lepidopteran insect-resistant) transgenic plant. In representative embodiments, the method comprises: introducing into a plant a polynucleotide, expression cassette or vector of the invention comprising a nucleotide sequence that encodes a chimeric insecticidal protein of the invention (including toxin fragments and modified forms that are substantially identical to the polypeptides specifically disclosed herein), wherein the nucleotide sequence is expressed in the plant to produce the chimeric insecticidal protein of the invention, thereby conferring to the plant resistance to the insect pest, and producing an insect-resistant transgenic plant (e.g., as compared with a suitable control plant, such as a plant that does not comprise the polynucleotide, expression cassette or vector of the invention and/or does not express a polypeptide of the invention).

In embodiments, the method of introducing the polynucleotide, expression cassette or vector of the invention into the plant comprises first transforming a plant cell with the polynucleotide, expression cassette or vector and regenerating a transgenic plant therefrom, where the transgenic plant comprises the polynucleotide, expression cassette or vector and expresses the chimeric insecticidal protein of the invention.

Alternatively, or additionally, the introducing step can comprise crossing a first plant comprising the polynucleotide, expression cassette or vector with a second plant (e.g., a different plant from the first plant, for example, a plant that does not comprise the polynucleotide, expression cassette or vector) and, optionally, producing a progeny plant that comprises the polynucleotide, expression cassette or vector and expresses a chimeric insecticidal protein of the invention, thereby resulting in increased resistance to at least one insect pest. Thus, a transgenic plant of the invention encompasses a plant that is the direct result of a transformation event and the progeny thereof (of any generation) that comprise the polynucleotide, expression cassette or vector and optionally expresses the chimeric insecticidal protein resulting in increased resistance to at least one insect pest.

The invention further provides a method of identifying a transgenic plant of the invention, the method comprising detecting the presence of a polynucleotide, expression cassette, vector or chimeric insecticidal protein of the invention in a plant (or a plant cell, plant part, and the like derived therefrom), and thereby identifying the plant as a transgenic plant of the invention based on the presence of the polynucleotide, expression cassette, vector or chimeric insecticidal protein of the invention.

The invention further provides a method of producing a transgenic plant with increased resistance to at least one insect pest (e.g., a least one lepidopteran pest), the method comprising: planting a seed comprising a polynucleotide, expression cassette or vector of the invention, and growing a transgenic plant from the seed, where the transgenic plant comprises the polynucleotide, expression cassette or vector and produces the chimeric insecticidal protein.

In embodiments, transgenic plants produced by the methods of the invention comprise a polynucleotide, expression cassette or vector of the invention. In embodiments, a transgenic plant produced by the methods of the invention comprise a chimeric insecticidal protein of the invention and, optionally have increased resistance to at least one insect pest.

The methods of producing a transgenic plant described herein optionally comprise a further step of harvesting a seed from the transgenic plant, where the seed comprises the polynucleotide, expression cassette or vector and produces the chimeric insecticidal protein. Optionally, the seed produces a further transgenic plant that comprises the polynucleotide, expression cassette or vector and produces the chimeric insecticidal protein, and thereby has increased resistance to at least one insect pest.

The invention further provides plant parts, plant cells, plant organs, plant cultures, seed, plant extracts, harvested products and processed products of the transgenic plants produced by the methods of the invention.

As a further aspect, the invention also provides a method of producing seed, the method comprising: providing a transgenic plant that comprises a polynucleotide, expression cassette or vector of the invention, and harvesting a seed from the transgenic plant, wherein the seed comprises the polynucleotide, expression cassette, vector and produces the chimeric insecticidal protein. Optionally, the seed produces a further transgenic plant that comprises the polynucleotide, expression cassette or vector and produces the chimeric insecticidal protein, and thereby has increased resistance to at least one insect pest. In representative embodiments, the step of providing the transgenic plant comprises planting a seed that produces the transgenic plant.

The invention further provides a method of producing a hybrid plant seed, the method comprising: crossing a first inbred plant, which is a transgenic plant comprising a polynucleotide, expression cassette or vector of the invention, and optionally expressing a chimeric insecticidal protein of the invention with a different inbred plant (e.g., an inbred plant that does not comprise a polynucleotide, expression cassette or vector of the invention) and allowing hybrid seed to form. Optionally, the method further comprises harvesting a hybrid seed. In embodiments, the hybrid seed comprises the polynucleotide, expression cassette or vector of the invention, and in embodiments may further comprise a chimeric insecticidal protein of the invention and have increased resistance to an insect pest. In embodiments, the hybrid seed produces a transgenic plant that comprises the polynucleotide, expression cassette or vector of the invention, expresses the chimeric insecticidal protein of the invention, and has increased resistance to at least one insect pest.

In some embodiments, a transgenic plant of the invention is resistant to at least one lepidopteran insect pest (as described herein). In embodiments, the transgenic plant controls a fall armyworm insect pest or colony that is resistant to a Vip3A (e.g., a Vip3Aa protein, for example, as expressed in maize event MIR162) and/or Cry1F protein (e.g., a Cry1Fa protein, for example, as expressed in maize event TC1507).

In further embodiments, a method of controlling at least one insect pest (e.g., at least one lepidopteran insect pest, such as fall armyworm) comprises providing a chimeric insecticidal protein of the invention. In embodiments, the method comprises delivering (e.g., orally delivering) to the insect pest or an environment thereof an effective amount of a chimeric insecticidal protein of the invention. Generally, to be effective, the polypeptide is orally ingested by the insect. However, the chimeric insecticidal protein can be delivered to the insect in many recognized ways. The ways to deliver a protein orally to an insect include, but are not limited to, providing the protein (1) in a transgenic plant, wherein the insect eats (ingests) one or more parts of the transgenic plant, thereby ingesting the polypeptide that is expressed in the transgenic plant; (2) in a formulated protein composition(s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; or (5) any other art-recognized protein delivery system. Thus, any method of oral delivery to an insect can be used to deliver the toxic proteins of the invention. In some particular embodiments, the chimeric insecticidal protein of the invention is delivered orally to an insect, for example, where the insect ingests one or more parts of a transgenic plant of the invention.

In other embodiments, the insecticidal protein of the invention is delivered orally to an insect, wherein the insect ingests one or more parts of a plant sprayed with a composition comprising the insecticidal protein of the invention. Delivering the composition of the invention to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with a compound(s), composition(s) or formulation(s) are well-known to those of skill in the art.

In further embodiments, the invention provides a method of controlling a lepidopteran insect pest that is resistant to a Vip3A protein (e.g., a Vip3Aa protein, for example, as expressed by maize event MIR162) and/or a Cry1F protein (e.g. a Cry1Fa protein, for example, as expressed by maize event TC1507) comprising delivering to the lepidopteran insect or an environment thereof an effective amount of a chimeric insecticidal protein or composition of the invention. In representative embodiments, the resistant insect pest is a resistant fall armyworm insect pest or colony.

In other embodiments, the invention provides a method of preventing the development of resistance in a population of a target lepidopteran insect pest to a Vip3A (e.g., a Vip3Aa protein, for example, as expressed by maize event MIR162) and/or Cry1F (e.g. a Cry1Fa protein, for example, as expressed by maize event TC1507) protein expressed in a transgenic plant, the method comprising delivering to the target population a transgenic plant comprising a polynucleotide comprising a nucleotide sequence encoding a Vip3A protein and/or a nucleotide sequence encoding a Cry1F protein; and a polynucleotide expression cassette or vector of the invention expressing a chimeric insecticidal protein of the invention. In some embodiments, the target lepidopteran insect pest is fall army worm. According to foregoing embodiments, the transgenic plant can comprise a breeding stack of two or more of the insecticidal traits, a molecular stack of two or more of the insecticidal traits, or a combination of both.

In some embodiments, the invention encompasses a method of providing a farmer with a means of controlling an insect pest (e.g., a lepidopteran pest, such as fall armyworm), the method comprising supplying or selling to the farmer plant material such as a seed, the plant material comprising a polynucleotide, expression cassette, vector capable of expressing a chimeric insecticidal protein of the invention. In embodiments, the plant material comprises the chimeric insecticidal protein of the invention and, optionally, has increased resistance to at least one insect pest. In embodiments, the plant material is a seed, and a plant grown from the seed comprises the polynucleotide, expression cassette or vector of the invention, expresses a chimeric insecticidal protein of the invention, and has increased resistance to the at least one insect pest.

In addition to providing compositions, the invention provides methods of producing a chimeric insecticidal protein toxic to a lepidopteran pest. Such a method comprises, culturing a transgenic non-human host cell that comprises a polynucleotide, expression cassette or vector of the invention that expresses a chimeric insecticidal protein of the invention under conditions in which the host cell produces the chimeric insecticidal protein that is toxic to the lepidopteran pest. In some embodiments, the transgenic non-human host cell is a plant cell. In some other embodiments, the plant cell is a maize cell. In other embodiments, the conditions under which the plant cell or maize cell are grown include natural sunlight. In other embodiments, the transgenic non-human host cell is a bacterial cell. In still other embodiments, the transgenic non-human host cell is a yeast cell.

In some embodiments, the methods of the invention provide control of at least one lepidopteran insect pest, including without limitation, one or more of the following: *Ostrinia* spp. such as *O. nubilalis* (European corn borer) and/or *O. furnacalis* (Asian corn borer); *Plutella* spp. such as *P. xylostella* (diamondback moth); *Spodoptera* spp. such as *S. frugiperda* (fall armyworm), *S. littoralis* (Egyptian cotton leafworm), *S. ornithogalli* (yellowstriped armyworm), *S. praefica* (western yellowstriped armyworm), *S. eridania* (southern armyworm) and/or *S. exigua* (beet armyworm); *Agrotis* spp. such as *A. ipsilon* (black cutworm), *A. segetum* (common cutworm), *A. gladiaria* (claybacked cutworm), and/or *A. orthogonia* (pale western cutworm); *Striacosta* spp. such as *S. albicosta* (western bean cutworm); *Helicoverpa* spp. such as *H. zea* (corn earworm), *H. punctigera* (native budworm), and/or *H. armigera* (cotton bollworm); *Heliothis* spp. such as *H. virescens* (tobacco budworm); *Diatraea* spp. such as *D. grandiosella* (southwestern corn borer) and/or *D. saccharalis* (sugarcane borer); *Trichoplusia* spp. such as *T. ni* (cabbage looper); *Sesamia* spp. such as *S. nonagroides* (Mediterranean corn borer) and/or *S. calamistis* (pink stem borer); *Pectinophora* spp. such as *P. gossypiella* (pink bollworm); *Cochylis* spp. such as *C. hospes* (banded sunflower moth); Manduca spp. such as *M. sexta* (tobacco hornworm) and/or *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia* spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. unipuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Chrysodeixis* spp. Such as *C. includes* (soybean looper); *Feltia* spp. such as *F. ducens* (dingy cutworm); *Chilo* spp. such as *C. suppressalis* (striped stem borer), *Cnaphalocrocis* spp. such as *C. medinalis* (rice leaffolder), or any combination of the foregoing. In embodiments, the methods of the invention provide control of a fall armyworm insect pest or colony that is resistant to a Vip3A (e.g., a Vip3Aa protein, for example, as expressed in maize event MIR162) and/or Cry1F protein (e.g., a Cry1Fa protein, for example, as expressed in maize event TC1507).

The invention also provides for uses of the chimeric insecticidal proteins, nucleic acids, transgenic plants, plant parts, seed and insecticidal compositions of the invention, for example, to control an insect pest, such as a lepidopteran pest (as described herein).

In embodiments, the invention provides a method of using a polynucleotide, expression cassette, vector or host cell of the invention to produce an insecticidal composition for controlling an insect pest (e.g., a lepidopteran insect pest).

In embodiments, the invention provides a method of using a polynucleotide, expression cassette or vector of the invention to produce a transgenic seed, where the transgenic seed grows a transgenic plant with increased resistance to an insect pest.

As another aspect, the invention also contemplates the use of a transgenic plant of the invention to produce a transgenic seed, which is optionally a hybrid seed.

In embodiments, the invention provides a method of using a chimeric insecticidal protein, polynucleotide, expression cassette, vector, transgenic plant or insecticidal composition of the invention to prevent the development of resistance in a population of a target lepidopteran insect pest to a Vip3A protein and/or Cry1F protein (each as described herein).

Statements of the invention include without limitation:

1. A chimeric insecticidal protein that is toxic to a lepidopteran insect pest comprising in an N-terminal to C-terminal direction: (a) an N-terminal region of a first Cry1 protein, which is an N-terminal region of a BT-0029 protein of SEQ ID NO:2 or an amino acid sequence that is at least 90% identical thereto, fused to (b) a C-terminal region of a different Cry1 protein; wherein a crossover position between the first Cry1 protein and the different Cry1 protein is located in conserved block 3.

2. The chimeric insecticidal protein according to statement 1, wherein the different Cry1 protein is a Cry1F, a Cry1G, a Cry1I or a Cry1K protein.

3. The chimeric insecticidal protein according to statement 1, wherein the different Cry1 protein is a Cry1Fa protein.

4. The chimeric insecticidal protein according to statement 1, wherein the different Cry1 protein is a Cry1Ia or a Cry1If protein.

5. The chimeric insecticidal protein according to statement 1, wherein the different Cry1 protein is a BT-0022 protein of SEQ ID NO: 1.

6. The chimeric insecticidal protein according to statement 1, wherein the C-terminal region of the different Cry1 protein comprises an amino acid sequence corresponding to an amino acid sequence from position 464 to 602 of SEQ ID NO: 8 or an amino acid sequence that is at least 80% identical thereto.

7. The chimeric insecticidal protein according to statement 1, wherein the C-terminal region of the different Cry1 protein comprises an amino acid sequence corresponding to an amino acid sequence from position 498 to 636 of SEQ ID NO: 1 or an amino acid sequence that is at least 80% identical thereto.

8. The chimeric insecticidal protein according to any one of statements 1 to 7, wherein the N-terminal region of the first Cry1 protein comprises an amino acid sequence corresponding to an amino acid sequence from position 1 to 458 of SEQ ID NO: 2 or an amino acid sequence that is at least 90% identical thereto.

9. The chimeric insecticidal protein according to any one of statements 1 to 8, wherein the chimeric insecticidal protein further comprises at the N-terminus a peptidyl fragment that is cleaved from the protoxin after ingestion by the lepidopteran insect pest.

10. The chimeric insecticidal protein according to any one of statements 1 to 9, wherein the chimeric insecticidal protein further comprises at the C-terminus a pro-toxin tail from a Cry protein that is cleaved from the protoxin after ingestion by the lepidopteran insect pest.

11. The chimeric insecticidal protein according to any one of statements 1 to 10, wherein the chimeric insecticidal protein comprises: (a) the amino acid sequence from position 1 to 597 of SEQ ID NO: 3 or a toxin fragment thereof, or (b) an amino acid sequence that is at least 80% identical to the amino acid sequence of (a).

12. The chimeric insecticidal protein according to any one of statements 1 to 11, wherein the chimeric insecticidal protein comprises: (a) the amino acid sequence of SEQ ID NO: 3 or a toxin fragment thereof; or (b) an amino acid sequence that is at least 80% identical to the amino acid sequence of (a).

13. The chimeric insecticidal protein according to any one of statements 1 to 10, wherein the chimeric insecticidal protein comprises: (a) the amino acid sequence from positions 1 to 597 of SEQ ID NO: 9 or a toxin fragment thereof; or (b) an amino acid sequence that is at least 80% identical to the amino acid sequence of (a).

14. The chimeric insecticidal protein according to any one of statements 1 to 10 or 13, wherein the chimeric insecticidal protein comprises: (a) the amino acid sequence of SEQ ID NO: 9 or a toxin fragment thereof; or (b) an amino acid sequence that is at least 80% identical to the amino acid sequence of (a).

15. The chimeric insecticidal protein according to any one of statements 1 to 14, wherein the chimeric insecticidal protein comprises the amino acid sequence of SEQ ID NO: 3 or SEQ ID NO: 9.

16. The chimeric insecticidal protein according to any one of statements 1 to 15, wherein the chimeric insecticidal protein has insecticidal activity against one or more of *Spodoptera frugiperda* (fall armyworm), *Chrysodeixis* includes (soybean looper), *Diatraea* saccharalis (sugarcane borer), *Diatraea grandiosella* (southwest corn borer), and *Agrotis ipsilon* (black cutworm).

17. The chimeric insecticidal protein according to any one of statements 1 to 16, wherein the chimeric insecticidal protein has insecticidal activity against a *Spodoptera frugiperda* insect pest or colony with resistance to a Vip3A protein and/or a Cry1F protein.

18. A polynucleotide comprising a nucleotide sequence encoding the chimeric insecticidal protein according to any one of statements 1 to 17.

19. The polynucleotide according to statement 18, wherein the polynucleotide is codon optimized for expression in a plant.

20. The polynucleotide according to statement 18 or statement 19, wherein the polynucleotide comprises a nucleotide sequence that comprises: (a)

a nucleotide sequence of SEQ ID NO: 4, SEQ ID NO: 5, SEQ ID NO: 6, SEQ ID NO: 7, SEQ ID NO: 10, SEQ ID NO: 11 or SEQ ID NO: 14 or a toxin-encoding fragment thereof; (b) a nucleotide sequence that is substantially identical to the nucleotide sequence of (a); or (c) a nucleotide sequence that anneals under stringent hybridization conditions to the nucleotide sequence of (a) or (b); or (d) a nucleotide sequence that differs from the nucleotide sequence of (a), (b) or (c) due to the degeneracy of the genetic code.

21. The polynucleotide according to statement 18 or statement 19, wherein the nucleotide sequence comprises the nucleotide sequence of SEQ ID NO: 4, SEQ ID NO: 5, SEQ ID NO: 6, SEQ ID NO: 7, SEQ ID NO: 10, SEQ ID NO: 11 or SEQ ID NO: 14.

22. A nucleic acid molecule comprising the polynucleotide according to any one of statements 18 to 21 operably associated with a heterologous promoter.

23. The nucleic acid molecule according to statement 22, wherein the heterologous promoter is a plant expressible promoter.

24. A vector comprising the polynucleotide according to any one of statements 18 to 21 or the nucleic acid molecule according to statement 22 or statement 23.

25. A transgenic cell comprising the polynucleotide according to any one of statements 18 to 21, the nucleic acid molecule according to statement 22 or statement 23, or the vector according to statement 24.

26. The transgenic cell according to statement 25, wherein the cell is a transgenic bacterial cell.

27. The transgenic cell according to statement 25, wherein the cell is a transgenic plant cell.

28. The transgenic plant cell according to statement 27, wherein the plant cell is: (i) a monocot cell, optionally a barley cell, a maize cell, an oat cell, a rice cell, a sorghum cell, a sugarcane cell or a wheat cell; or (ii) a dicot cell, optionally a soybean cell, a sunflower cell, a tomato cell, a cole crop cell, a cotton cell, a sugar beet cell or a tobacco cell.

29. A transgenic plant comprising the transgenic plant cell according to statement 27 or statement 28.

30. The transgenic plant according to statement 29, wherein the plant is: (i) a monocot plant, optionally a barley plant, a maize plant, an oat plant, a rice plant, a sorghum plant, a sugarcane plant or a wheat plant; or (ii) a dicot plant, optionally a soybean plant, a sunflower plant, a tomato plant, a cole crop plant, a cotton plant, a sugar beet plant or a tobacco plant.

31. The transgenic plant according to statement 28 or statement 29, wherein the transgenic plant comprises a further nucleotide sequence encoding a second insect control agent.

32. A transgenic plant part of the transgenic plant according to any one of statements 29 to 31, wherein the transgenic plant part comprises the chimeric insecticidal protein.

33. A transgenic seed of the transgenic plant according to any one of statements 29 to 31.

34. A harvested product derived from the transgenic plant according to any one of statements 29 to 31, the transgenic plant part according to statement 32, or the transgenic seed according to statement 33, wherein the harvested product comprises the chimeric insecticidal protein.

35. A processed product derived from the harvested product according to statement 34, wherein the processed product is a flour, a meal, an oil, a starch, or a product derived from any of the foregoing.

36. An insecticidal composition comprising the chimeric insecticidal protein according to any one of statements 1 to 17 and an agriculturally acceptable carrier.

37. The insecticidal composition according to statement 36, wherein the agriculturally acceptable carrier is a powder, a dust, a pellet, a granule, a spray, an emulsion, a colloid or a solution.

38. The insecticidal composition according to statement 36 or statement 37, wherein the composition is a desiccated, lyophilized, homogenized, extracted, filtrated, centrifuged and/or sedimented composition and/or is a bacterial culture concentrate.

39. The insecticidal composition according to any one of statements 36 to 38, wherein the composition comprises a transgenic bacterial cell that produces the chimeric insecticidal protein.

40. The insecticidal composition according to any one of statements 36 to 39, wherein the composition comprises from about 1% to about 99% by weight of the chimeric insectidical protein.

41. The insecticidal composition according to any one of statements 36 to 40, wherein the composition comprises a second insect control agent.

42. A method of producing a transgenic plant with increased resistance to a lepidopteran insect pest, the method comprising introducing into a plant the polynucleotide of any one of statements 18 to 21, the nucleic acid molecule of statement 22 or statement 23, or the vector of statement 24, wherein the chimeric insecticidal protein is expressed in the plant, thereby producing a transgenic plant with increased resistance to an insect pest.

43. The method according to statement 42, wherein the introducing step comprises: (i) transforming a plant cell with the polynucleotide, nucleic acid molecule or vector and regenerating a transgenic plant; or (ii) crossing a first plant comprising the polynucleotide, nucleic acid molecule or vector with a second plant.

44. The method according to statement 42 or statement 43, wherein the method further comprises obtaining a progeny plant from the transgenic plant, wherein the progeny plant comprises the polynucleotide, the nucleic acid molecule or the vector and has increased resistance to an insect pest.

45. A method of producing a transgenic plant with increased resistance to a lepidopteran insect pest, the method comprising: (a) planting a seed comprising the polynucleotide according to any one of statements 18 to 21, the nucleic acid molecule according to statement 22 or statement 23, or the vector according to statement 24; and (b) growing a transgenic plant from the seed, wherein the transgenic plant comprises the polynucleotide, nucleic acid molecule or vector and produces the chimeric insecticidal protein.

46. The method according to statement 45, wherein the method further comprises: (c) harvesting a seed from the transgenic plant of (b), wherein the harvested seed comprises the chimeric insecticidal protein.

47. A method of producing a seed, the method comprising: (a) providing a transgenic plant that comprises the polynucleotide according to any one of statements 18 to 21, the nucleic acid molecule according to statement 22 or statement 23, or the vector according to statement 24; and (b) harvesting a seed from the transgenic plant of (a), wherein the harvested seed comprises the chimeric insecticidal protein.

48. A method of producing a hybrid plant seed, the method comprising: (a) crossing a first inbred plant, which is a transgenic plant comprising the polynucleotide according to any one of statements 18 to 21, the nucleic acid molecule according to statement 22 or statement 23, or the vector according to statement 24, with a different inbred plant; and (b) allowing a hybrid seed to form.

49. A method of controlling a lepidopteran insect pest, the method comprising delivering to the insect pest or an environment thereof a composition comprising an effective amount of the chimeric insecticidal protein of any one of statements 1 to 17 or the insecticidal composition of any one of statements 36 to 41.

50. A method of controlling a lepidopteran insect pest resistant to a Vip3A protein and/or a Cry1F protein, the method comprising delivering to the resistant lepidopteran insect pest or an environment thereof the insecticidal protein of any one of statements 1 to 17 or the insecticidal composition of any one of statements 36 to 41.

51. A method of reducing the development of resistance to a Vip3A protein and/or a Cry1F protein in a population of a target lepidopteran insect pest, the method comprising delivering to the target population or an environment thereof a transgenic plant comprising: (i) the polynucleotide according to any one of statements 18 to 21, the nucleic acid molecule according to statement 22 or statement 23, or the vector according to statement 24; and (ii) a polynucleotide comprising a nucleotide sequence encoding a Vip3A protein and/or a nucleotide sequence encoding a Cry1F protein; wherein the chimeric insecticidal protein and the Vip3A protein and/or the Cry1F protein are produced in the transgenic plant.

52. The method according to any one of statements 42 to 51, wherein the lepidopteran insect pest includes one or more of *Spodoptera frugiperda* (fall armyworm), *Chrysodeixis includes* (soybean looper), *Diatraea saccharalis* (sugarcane borer), *Diatraea grandiosella* (southwest corn borer) and *Agrotis ipsilon* (black cutworm).

53. The method according to any one of statements 42 to 52, wherein the lepidopteran insect pest includes a *Spodoptera frugiperda* (fall armyworm) that is resistant to a Vip3A protein and/or a Cry1F protein.

54. The method according to any one of statements 42 to 53, wherein the plant is: (i) a monocot plant, optionally a barley plant, a maize plant, an oat plant, a rice plant, a sorghum plant, a sugarcane plant or a wheat plant; or (ii) a dicot plant, optionally a soybean plant, a sunflower plant, a tomato plant, a cole crop plant, a cotton plant, a sugar beet plant or a tobacco plant.

55. The method according to any one of statements 42 to 54, wherein the plant is a maize plant.

The invention will now be described with reference to the following examples. It will be appreciated by those skilled in the art that these examples do not limit the scope of the claims to the invention, but are rather intended to be exemplary of certain embodiments. Other embodiments of the invention may be practiced without departing from the spirit and the scope of the invention, the scope of which is defined by the disclosure and the appended claims.

EXAMPLES

Example 1. Discovery of a Chimeric BT-0029 Protein, Bt29-Bt22 with Insecticidal Activity Against Fall Armyworm Two lepidopteran-active proteins from *Bacillus thuringiensis* (Bt), BT-0022 (SEQ ID NO: 1; nearest known Cry family member Cry1If) and BT-0029 (SEQ ID NO:2; nearest known Cry family member Cry1Gb), have been disclosed in PCT/US16/038947.

As shown in Table 1 below, the insect spectrum data for BT-0022 and BT-0029 indicate that BT-0022 has no fall armyworm (FAW *Spodoptera frugiperda*) activity, and BT-0029 has only weak FAW activity. Other lepidopteran insect pests tested were: European corn borer (ECB; *Ostrinia nubilalis*), black cutworm (BCW; *Agrotis ipsilon*), corn earworm (CEW; *Helicoverpa zea*), sugarcane borer (SCB; *Diatraea saccharalis*), southwestern corn borer (SWCB; *Diatraea grandiosella*), western bean cutworm (WBCW; *Striacosta albicosta*), soybean looper (SBL; *Pseudoplusia includens*), velvet bean caterpillar (VBC; *Anticarsia gemmatalis*), and tobacco budworm (TBW; *Heliothis virescens*).

TABLE 1

Insecticidal activity of BT-0022 and BT-0029 against various Lepidopteran insects.

| | % Mortality | | | | | | | | |
|---|---|---|---|---|---|---|---|---|---|
| | ECB | BCW | FAW | CEW | SCB | SWCB | WBCW | SBL | VBC | TBW |
| BT-0022 | 100 | 100 | 0 | 20 (M) | 92 | 100 | 0 | 100 | 0 | 42 (S) |
| BT-0029 | 0 | 25 | 25 | 8 | 33 | 17 | ND | 100 | 100 | ND |

M—Medium-sized larvae
S—Small-sized larvae
ND—Not Determined

A protein engineering approach was used in an effort to try to enhance the FAW activity of BT-0029. Using BT-0029 as a template, six engineered proteins were designed by replacing domain Ill (DIII) of BT-0029 with a domain Ill from a different Cry protein. Table 2 illustrates six chimeric proteins with their domain composition information. Table 3 provides the sequence information for the full-length proteins.

TABLE 2

Engineered BT-0029 proteins by domain swap

| Name | Domain I | Domain II | Domain III | Protoxin Tail |
|---|---|---|---|---|
| Bt29-1Ab | BT-0029 | BT-0029 | Cry1Ab | BT-0029 |
| Bt29-Bt22 | BT-0029 | BT-0029 | BT-0022 | BT-0029 |
| Bt29-Bt67 | BT-0029 | BT-0029 | BT-0067 | BT-0029 |
| Bt29-Bt51 | BT-0029 | BT-0029 | BT-0051 | BT-0029 |
| Bt29-8D | BT-0029 | BT-0029 | Cry8D | BT-0029 |
| Bt29-3A | BT-0029 | BT-0029 | Cry3A | BT-0029 |

TABLE 3

Full-length protein sequence information.

| Name | Closest Cry Family Member | Sequence |
|---|---|---|
| BT-0029 | Cry1Gb | SEQ ID NO: 2 |
| Cry1Ab | Not applicable | Genbank accession No. AAA22330.1 |
| BT-0022 | Cry1If | SEQ ID NO: 1 |
| Bt-0067 | Cry9Eb | WO2016/094165 |
| Bt-0051 | Cry9Ca | WO2016/094159 |
| Cry8D | Not applicable | Genbank accession No. BAF93483.1 |
| Cry3A | Not applicable | Genbank accession No. AAA22336.1 |
| Cry1Ca | Not applicable | Genbank accession No. AF362020.1 | cDNAs encoding the engineered proteins were synthesized by Genewiz (South Plainfield, N.J.) and cloned into a *Bacillus thuringiensis* (Bt) expression vector containing a Cry1Ac promoter and no terminator. The plasmid DNAs were introduced into Bt strain AB227 via an electroporation-mediated transformation procedure. All six engineered proteins were produced as crystal proteins in Bt. The crystal proteins were purified from the cultures and dissolved in a buffer containing 50 mM Na2CO$_3$ pH 11.0, 2 mM DTT. Each soluble protein was then evaluated in an insect bioassay.

Briefly, insecticidal activity of the chimeric proteins was examined by an artificial diet based insect bioassay in which the solubilized crystal proteins were overlaid on the surface of artificial insect diet, with a final concentration of 2-3.2 μg/cm2. The buffer (50 mM Na2CO$_3$ pH 11.0, 2 mM DTT) used for solubilizing the Bt crystal proteins served as the negative control. Full-length Cry1Fa protein (SEQ ID NO: 8) was used as a positive control for FAW activity. Each chimeric protein was tested in duplicate. Insect mortality was assessed on day 7.

The results are shown in Table 4. When the chimeric proteins were tested in the insect bioassay, the Bt29-Bt22 chimera (SEQ ID NO: 3) showed strong insecticidal activity against FAW, whereas two other chimeric proteins (Bt29-Bt67 and Bt29-3A) showed only minor activity to the pest. The Bt29-1Ab chimera did not demonstrate any detectable FAW activity.

For this test, not enough protein of the Bt29-Bt51 and Bt29-8D chimeras were produced to evaluate insecticidal activity.

TABLE 4

Insecticidal Activity against Fall Armyworm

| Treatment | FAW % Mortality | Treatment | FAW % Mortality |
|---|---|---|---|
| Buffer (negative control) | 8 | Bt29-Bt67 | 17 |
| Cry1Fa (full-length; positive control) | 100 | Bt29-3A | 25 |
| Bt29-Bt22 | 100 | Bt29-3A | 33 |
| Bt29-Bt22 | 83 | Bt29-1Ab | 0 |
| Bt29-Bt67 | 8 | Bt29-1Ab | 0 |
| Bt29-Bt67 | 17 | | |

Example 2: Insecticidal Activity of Chimeric BT-0029 Proteins Against Various Lepidopteran Pests Four of the chimeric proteins described in Example 1 (Bt29-3A, Bt29-Bt22, Bt29-1Ab and Bt29-Bt67) were examined for their insecticidal activities against the following lepidopteran pests using art-recognized artificial diet bioassay methods: sugarcane borer (SCB; *Diatraea saccharalis*), southwestern corn borer (SWCB; *Diatraea grandiosella*), soybean looper (SBL; *Pseudoplusia includens*), corn earworm (CEW; *Helicoverpa zea*), tobacco budworm (TBW; *Heliothis virescens*), black cutworm (BCW; *Agrotis ipsilon*) and European corn borer (ECB; *Ostrinia nubilalis*).

As shown in Table 5, all four chimeric proteins tested retained the strong SBL activity of native BT-0029. Bt29-Bt22 and Bt29-Bt67 had weak SCB activity comparable to native BT-0029, whereas Bt29-3A and Bt29-1Ab essentially lost all SCB activity. A slightly increased SWCB activity was observed in Bt29-Bt67 compared to full-length BT-0029. Fairly consistent with the results in Table 1 for native BT-0029, only weak BCW activity was observed for Bt29-3A, Bt29-Bt22 and Bt29-Bt67, and none of the chimeras had CEW, TBW or ECB activity.

TABLE 5

Insecticidal Activity of BT-0029 chimeric proteins against Lepidopteran Pests

| Treatment | % Mortality | | | | | | |
|---|---|---|---|---|---|---|---|
| | SCB | SWCB | SBL | CEW | TBW | BCW | ECB |
| Buffer (negative control) | 0 | 17 | 0 | 0 | 0 | 8 | 0 |
| Cry1Fa (full-length; positive control) | 25 | 42 | 100 | 73 | 100 | 42 | 100 |
| Bt29-3A | 0 | 42 | 100 | 0 | 0 | 8 | 0 |
| Bt29-3A | 8 | 25 | 100 | 0 | 0 | 25 | 0 |
| Bt29-Bt22 | 50 | 17 | 100 | 0 | 0 | 17 | 0 |
| Bt29-Bt22 | 33 | 67 | 100 | 0 | 0 | 25 | 0 |
| Bt29-Bt67 | 25 | 58 | 100 | 0 | 0 | 33 | 0 |
| Bt29-Bt67 | 42 | 73 | 100 | 0 | 0 | 8 | 0 |
| Bt29-1Ab | 8 | 0 | 100 | 0 | 0 | 0 | 0 |
| Bt29-1Ab | 0 | 0 | 100 | 0 | 0 | 0 | 0 |
| Bt29-1Fa | 100 | 100 | 100 | 0 | 0 | 0 | 75 |

Example 3: Bt29-1F Possesses Insecticidal Activity Against Fall Armyworm

To examine additional chimeric proteins, a second set of BT-0029 chimeric proteins was designed and tested (Table 6). Bt29-1Fa is a chimeric protein in which domain III of BT-0029 was replaced with domain III of Cry1Fa. The full-length amino acid sequence of Cry1Fa is provided as SEQ ID NO: 8 (see also Genbank accession number AAB00376.1). The amino acid sequence of the Bt29-1Fa chimera is provided as SEQ ID NO: 9, wherein the Cry1Fa sequence is amino acids 459 to 597.

Bt29-1Ka is a chimeric protein in which domain III of BT-0029 was replaced with domain III of Cry1Ka. The full-length amino acid sequence of Cry1Ka is provided as SEQ ID NO: 12 (see also Genbank accession number AAB00376.1). The amino acid sequence of the Bt29-1Ka chimera is also provided as SEQ ID NO: 13, wherein the Cry1Ka sequence is amino acids 459 to 597. A second version of a Bt29-1Ka chimeric protein (designated herein as Bt29-1Kav2) was made by moving the cross-over junction between the Cry1Ka sequence and the BT-0029 sequence in the C-terminus of domain III from amino acid 598 (the cross-over in the first Bt29-1Ka chimera) to amino acid 610. The amino acid sequence of the Bt29-1Kav2 chimera is provided as SEQ ID NO: 15, wherein the Cry1Ka sequence is amino acids 459 to 609.

Bt29-1Ca is a chimeric protein in which domain III of Bt-0029 was replaced with domain III of Cry1Ca. The full-length amino acid sequence of Cry1Ca is provided as SEQ ID NO: 17 (see also Genbank accession number AF362020.1). The amino acid sequence of the Bt29-1Ca chimera is provided as SEQ ID NO: 18, wherein the the Cry1Ca sequence is amino acids 467 to 617.

TABLE 6

Engineered BT-0029 proteins by domain III swap

| Name | Domain I | Domain II | Domain III | Protoxin Tail |
|---|---|---|---|---|
| Bt29-1Fa | BT-0029 | BT-0029 | Cry1Fa | BT-0029 |
| Bt29-1Ka | BT-0029 | BT-0029 | Cry1Ka | BT-0029 |
| Bt29-1Ca | BT-0029 | BT-0029 | Cry1Ca | BT-0029 |

Insecticidal activity of the Bt29-1Fa (SEQ ID NO: 9), Bt29-1Ka (SEQ ID NO: 13, Bt29-1Kav2 (SEQ ID NO: 16) and Bt29-1Ca (SEQ ID NO: 18) chimeras were examined by an artificial diet based insect bioassay, in which the solubilized proteins were overlaid on the surface of artificial insect diet, with a final concentration of 2 µg/cm². The buffer (50 mM Na2CO3 pH 10.5, 2 mM DTT) used for solubilizing the Bt crystal proteins served as the negative control. Full-length Cry1Fa protein (SEQ ID NO: 8) was used as a positive control for FAW activity. Each chimeric protein was tested in triplicate. Insecticidal activity was assessed as effective mortality on day 7 (larvae that have growth inhibition and are moribund are scored as effectively dead).

As shown in Table 7, the chimeric protein designated Bt29-1Fa demonstrated strong activity against FAW.

In this test, insufficient Bt29-1Ka protein was produced to evaluate in the bioassay. Surprisingly, the Bt29-1Kav2 chimera produced protein and was active against fall armyworm (see Table 7).

TABLE 7

Insecticidal Activity of Bt29-1Fa hybrid against Fall Armyworm

| Treatment | FAW % Mortality |
|---|---|
| Bt29-1Fa | 100 |
| Bt29-1Fa | 100 |
| Bt29-1Fa | 100 |
| Bt29-1Ca | 100 |
| Bt29-1Kav2 | 75 |
| Cry1Fa (full length; positive control) | 100 |
| Buffer (negative control) | 8 |

Example 4: Bt29-Bt22 and Bt29-1Fa Possess Insecticidal Activity Against Cry1F-Resistant Fall Armyworm To determine if the toxicity of the BT-0029 chimeric proteins to FAW is through a mode of action (MOA) distinct from Cry1Fa, the two chimeric proteins, Bt29-Bt22 and Bt29-1Fa were produced as described in Example 1, and the crystal proteins were isolated and purified. Purified crystals were dissolved in Buffer 1 (50 mM Na2CO3/NaHCO3, pH 11, 2 mM DTT), and the purity of the dissolved protein preparation was monitored using a Bio-Rad Experion system (BioRad, Hercules, Calif.)

The purified proteins were tested for efficacy against a strain of FAW that is resistant to the insecticidal toxin Cry1Fa. A diet-overlay assay was performed with various doses of each purified toxin (125, 500 and 2000 ng/cm2), essentially as described in Example 1. Vip3A protein (positive control) was dissolved in PBS and the other proteins in Buffer 1 (50 mM Na2CO₃/NaHCO₃, pH 11, 2 mM DTT). The two negative control treatments were PBS and Buffer 1. A FAW population that is susceptible to either Cry1Fa or Vip3A, i.e. FAW susceptible strain, was also tested. Each protein was tested in duplicates. Insecticidal activity was assessed as effective mortality on day 7 (larvae that have growth inhibition and are moribund are counted as effectively dead).

As shown in Table 8, the susceptible FAW larvae were controlled by Cry1Fa, Vip3A, Bt29-Bt22 and Bt29-1Fa, even at the lowest concentration. In contrast, the Cry1F-resistant FAW strain was not controlled by any dose of Cry1Fa tested, demonstrating the strain is resistant to this toxin (Table 9). Surprisingly, both Bt29-Bt22 and Bt29-1Fa were highly efficacious in controlling the Cry1F-resistant FAW even at a very low dose of 125 ng/cm² as shown in Table 9, suggesting that the mode of action of these two chimeric proteins against resistant FAW is different from the mode of action of a Cry1Fa protein.

TABLE 8

Insecticidal Activity of Bt29-Bt22 and Bt29-1Fa against susceptible Fall Armyworm at various concentrations

| Treatment | Dose (ng/cm2) | % Mortality |
| --- | --- | --- |
| Vip3Aa | 125 | 100 |
| Vip3Aa | 500 | 100 |
| Vip3Aa | 2000 | 100 |
| Cry1Fa | 125 | 100 |
| Cry1Fa | 500 | 100 |
| Cry1Fa | 2000 | 100 |
| Bt29-Bt22 | 125 | 90 |
| Bt29-Bt22 | 500 | 96 |
| Bt29-Bt22 | 2000 | 100 |
| Bt29-1Fa | 125 | 92 |
| Bt29-1Fa | 500 | 100 |
| Bt29-1Fa | 2000 | 100 |
| Buffer 1 | | 0 |
| PBS | | 0 |

TABLE 9

Insecticidal Activity of Bt29-Bt22 and Bt29-1Fa against Cry1Fa-resistant Fall Armyworm

| Treatment | Dose (ng/cm2) | % Mortality |
| --- | --- | --- |
| Vip3Aa | 125 | 100 |
| Vip3Aa | 500 | 100 |
| Vip3Aa | 2000 | 100 |
| Cry1Fa | 125 | 0 |
| Cry1Fa | 500 | 0 |
| Cry1Fa | 2000 | 0 |
| Bt29-Bt22 | 125 | 100 |
| Bt29-Bt22 | 500 | 100 |
| Bt29-Bt22 | 2000 | 100 |
| Bt29-1Fa | 125 | 100 |
| Bt29-1Fa | 500 | 100 |
| Bt29-1Fa | 2000 | 100 |
| Buffer 1 | | 0 |
| PBS | | 0 |

Example 5: Bt29-Bt22 and Bt29-1Fa Possess Insecticidal Activity Against Vip3A-Resistant Fall Armyworm To determine if the toxicity of the BT-0029 chimeric proteins is through a different MOA from Vip3A protein, the Bt29-Bt22 and Bt29-1Fa proteins were produced as described in Example 1, and the crystal proteins were isolated and purified. Purified crystals were dissolved in Buffer 1 (50 mM Na2CO₃/NaHCO₃, pH 11, 2 mM DTT), and the purity of the dissolved protein preparation was monitored using a Bio-Rad Experion system (BioRad, Hercules, Calif.).

The purified proteins were tested for efficacy against a strain of FAW that is resistant to the insecticidal toxin Vip3A. A diet-overlay assay was performed with various doses of each purified toxin (125, 500 and 2000 ng/cm²) essentially as described in Example 1. Vip3A protein was dissolved in PBS and the other proteins in Buffer 1 (50 mM Na2CO₃/NaHCO₃, pH 11, 2 mM DTT). The two negative control treatments were PBS and Buffer 1. Cry1Fa proteins was used as a positive control for the Vip3A-resistant FAW strain. Each protein was tested in duplicate. Insecticidal activity was assessed as effective mortality on day 7 (larvae that have growth inhibition and are moribund are scored as effectively dead).

The Vip3A-resistant FAW strain was not controlled by any dose of Vip3A tested, demonstrating that the strain is resistant to this toxin (Table 10). In contrast, both Bt29-Bt22 and Bt29-1Fa demonstrated a high degree of efficacy against the Vip3A-resistant FAW suggesting that the mode of action of these two chimeric proteins against resistant FAW is different from the mode of action of a Vip3A protein.

TABLE 10

Insecticidal Activity of Bt29-Bt22 and Bt29-1Fa against Vip3A-resistant Fall Armyworm

| Treatment | Dose (ng/cm2) | % Mortality |
| --- | --- | --- |
| Vip3Aa | 125 | 0 |
| Vip3Aa | 500 | 0 |
| Vip3Aa | 2000 | 0 |
| Cry1Fa | 125 | 100 |
| Cry1Fa | 500 | 100 |
| Cry1Fa | 2000 | 100 |
| Bt29-Bt22 | 125 | 100 |
| Bt29-Bt22 | 500 | 100 |
| Bt29-Bt22 | 2000 | 100 |
| Bt29-1Fa | 125 | 100 |
| Bt29-1Fa | 500 | 100 |
| Bt29-1Fa | 2000 | 100 |
| Buffer 1 | | 0 |
| PBS | | 0 |

Example 6. Truncations in Protoxin Tail Region

It is well-known that the protoxin form of Bt Cry proteins is processed at both the N- and C-terminal ends to produce the mature toxin. Six C-terminal truncated forms of the Bt29-Bt22 (SEQ ID NO: 3) chimera, which comprises a BT-0029 protoxin tail region, were made as shown in FIG. 3. In all truncated versions, designated herein as Bt29-Bt22Tr1 (SEQ ID NO: 20), Bt29-Bt22Tr2 (SEQ ID NO: 21), Bt29-Bt22Tr3 (SEQ ID NO: 22), Bt29-Bt22Tr4 (SEQ ID NO: 23), Bt29-Bt22Tr5 (SEQ ID NO: 24), Bt29-Bt22Tr6 (SEQ ID NO: 25), domain III of BT-0022 (ending with PVTA), and at least the first 6 amino acids of the BT-0029 protoxin tail (TFEAEY) were retained. Those skilled in the art will appreciate that the end of domain III and the beginning of the protoxin tail has not been delineated with precision for BT-0029 or the chimeras described herein. The core domain III shown in FIGS. 1A and 1B are based on alignments with other Cry proteins in which the domain III region has been delineated.

The Bt29-Bt22Tr1, -Tr2, -Tr4, and -Tr5 truncated forms all showed FAW activity assessed as growth inhibition (not mortality) in insect bioassays when tested as *E. coli* lysates. The Bt29-Bt22Tr1 and -Tr4 forms were the most promising, demonstrating the highest activity in this assay (67% and 75% growth inhibition, respectively).

A second Bt29-Bt22 full-length chimera was made wherein the protoxin tail region is from BT-0022 (Cry1I) instead of BT-0029 (Cry1G). Six C-terminal truncated forms of this full-length chimera, presented herein as SEQ ID Nos:26-31, were made and tested against fall armyworm and soybean looper. Cry1Fa was used as the positive control. Results are shown in Table 11.

TABLE 11

Insecticidal activity of Bt29-Bt22 with truncated BT-0022 protoxin tail against fall armyworm and soybean looper.

| Chimera | SEQ ID NO: | Effective Mortality (%) | |
|---|---|---|---|
| | | FAW | SBL |
| BT29BT22-TL22v1 | 26 | 75 | 100 |
| BT29BT22-TL22v2 | 27 | 63 | 100 |
| BT29BT22-TL22v3 | 28 | 50 | 100 |
| BT29BT22-TL22v4 | 29 | 58 | 100 |
| BT29BT22-TL22v5 | 30 | 54 | 100 |
| BT29BT22-TL22v6 | 31 | 83 | 100 |
| Buffer | NA | 0 | 0 |
| Cry1Fa | 8 | 100 | 100 |

Four truncated forms of the Bt29-1Fa (SEQ ID NO: 9), which comprises the BT-0029 protoxin tail region, presented herein as Bt29-1FaTr1 (SEQ ID NO:32), Bt29-1FaTr2 (SEQ ID NO: 33), Bt29-1FaTr3 (SEQ ID NO: 34) and Bt29-1FaTr4 (SEQ ID NO:35), were produced in an *E. coli* expression system and lysates were tested against fall armyworm. Results are shown in Table 12.

TABLE 12

Insecticidal activity of truncated Bt29-1Fa chimeric proteins.

| Chimeric Protein | SEQ ID NO: | % FAW Mortality |
|---|---|---|
| Bt29-1FaTr1 | 32 | 17 |
| Bt29-1FaTr2 | 33 | 8 |
| Bt29-1FaTr3 | 34 | 42 |
| Bt29-1FaTr4 | 35 | 58 |
| Cry1Fa | 8 | 100 |
| Buffer | NA | 0 |
| pET29 | NA | 0 |

Example 7. Expression and Activity of Chimeric Bt29-Bt22 and Bt29-Cry1Fa Proteins in Maize Plants Prior to expression in plants, synthetic polynucleotides comprising a nucleotide sequence encoding a Bt29-Bt22 and a Bt29-1Fa chimera were synthesized on an automated gene synthesis platform (Genscript, Inc., Piscataway, N.J.). For this example, a first and second expression cassette was made comprising a maize ubiquitin promoter (Ubi1) operably linked to either the Bt29-Bt22 or Bt29-1Fa chimeric coding sequence which was operably linked to a maize ubiquitin terminator and a third expression cassette was made comprising a Ubi1 promoter operably linked to a phosphomannose isomerase (PMI) coding sequence which was operably linked to a Ubi terminator. Expression of PMI allows for positive selection of transgenic plants on mannose. For plant transformation, the first and third expression cassettes and the second and third expression cassettes were cloned into a suitable vector for *Agrobacterium*-mediated maize transformation.

Transformation of immature maize embryos is performed essentially as described in Negrotto et al., 2000, Plant Cell Reports 19: 798 803. Briefly, *Agrobacterium* strain LBA4404 (pSB1) comprising an expression vector expressing Bt29-Bt22 or Bt29-Cry1Fa is grown on YEP (yeast extract (5 g/L), peptone (10 g/L), NaCl (5 g/L), 15 g/l agar, pH 6.8) solid medium for 2-4 days at 28° C. Approximately $0.8 \times 10^9$ *Agrobacterium* cells are suspended in LS-inf media supplemented with 100 μM As. Bacteria are pre-induced in this medium for approximately 30-60 minutes.

Immature embryos from an inbred maize line are excised from 8-12 day old ears into liquid LS-inf+100 μM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between approximately 20 and 25 embryos per petri plate are transferred to LSDc medium supplemented with cefotaxime (250 mg/l) and silver nitrate (1.6 mg/l) and cultured in the dark at approximately 28° C. for 10 days.

Immature embryos, producing embryogenic callus are transferred to LSD1M0.5S medium. The cultures are selected on this medium for approximately 6 weeks with a subculture step at about 3 weeks. Surviving calli are transferred to Reg1 medium supplemented with mannose. Following culturing in the light (16 hour light/8 hour dark regiment), green tissues are then transferred to Reg2 medium without growth regulators and incubated for about 1-2 weeks. Plantlets are transferred to Magenta GA-7 boxes (Magenta Corp, Chicago Ill.) containing Reg3 medium and grown in the light. After about 2-3 weeks, plants are tested for the presence of the PMI genes and the chimeric Bt cry gene by PCR. Positive plants from the PCR assay are transferred to a greenhouse for further evaluation.

Transgenic plants were evaluated for copy number (determined by Taqman analysis), protein expression level (determined by ELISA), and efficacy against insect species of interest in leaf excision bioassays. Specifically, plant tissue (leaf or silks) was excised from single copy events (V3-V4 stage) and infested with neonate larvae of a target pest, then incubated at room temperature for 5 days. Leaf disks from transgenic plants expressing each chimeric Bt protein were tested against fall armyworm (*Spodoptera frugiperda*, FAW).

Results confirm that the transgenic plants express the chimeric proteins of the invention and are active against insect pests. Protein expression in the transgenic events for the Bt29-Bt22 chimera ranged from about 25-125 ng/mg total soluble protein (TSP) and for the Bt29-1Fa chimera ranged from about 25-290 ng/mg TSP. About 90% and 92% of the transgenic events expressing the Bt29-Bt22 and Bt29-1Fa chimeras, respectively, produced 100% mortality and larval growth inhibition to fall armyworm.

The above examples clearly illustrate the advantages of the invention. Although the present invention has been described with reference to specific details of certain embodiments thereof, it is not intended that such details should be regarded as limitations upon the scope of the claimed invention except as and to the extent that they are included in the accompanying claims.

---

SEQUENCE LISTING

```
Sequence total quantity: 35
SEQ ID NO: 1            moltype = AA  length = 715
FEATURE                 Location/Qualifiers
REGION                  1..715
                        note = BT-0022 sequence assembled from Bacillus genome
                         mining.
source                  1..715
                        mol_type = protein
                        organism = synthetic construct
SEQUENCE: 1
MKSKNQNMHQ SLSNNATVDK NFTGSLENNT NTELQNFNHE GIEPFVSVST IQTGIGIAGK  60
ILGNLGVPFA GQVASLYSFI LGELWPKGKS QWEIFMEHVE ELINQKISTY ARNKALADLK  120
GLGDALAVYH ESLESWIKNR NNTRTRSVVK SQYITLELMF VQSLPSFAVS GEEVPLLPIY  180
AQAANLHLLL LRDASIFGKE WGLSDSEIST FYNRQVERTS DYSDHCTKWF DTGLNRLKGS  240
NAEIWVKYNQ FRRDMTLMVL DLVALFQSYD THMYPIKTTA QLTREVYTNA IGTVHPHPSF  300
TSTTWYNNNA PSFSAIEAAV IRSPHLLDFL EQVTIYSLLS RWSNTQYMNM WGGHKLEFRT  360
IGGTLNTSTQ GSTNTSINPV TLPFTSRDIY RTESLAGLNL FLTQPVNGVP RVDFHWKFVT  420
HPIASDNFYY PGYAGIGTQL QDSENELPPE TTGQPNYESY SHRLSHIGLI SASHVKALVY  480
SWTHRSADRT NTIHSDSITQ IPLVKAHTLQ SGTTVVKGPG FTGGDILRRT SGGPFAFSNV  540
NLDWNLSQRY RARIRYASTT NLRMYVTIAG ERIFAGQFNK TMNTGDPLTF QSFSYATIDT  600
AFTFPTKASS LTVGADTFSS GNEVYVDRFE LIPVTATLEA VTDLERAQKA VHELFTSTNP  660
GGLKTDVAKD HYTNTISKSV QSVFRCRCSE RTRIYRWGYP SKKEYWYIWG YTSKY       715

SEQ ID NO: 2            moltype = AA  length = 1169
FEATURE                 Location/Qualifiers
REGION                  1..1169
                        note = BT-0029 sequence assembled from Bacillus genome
                         mining.
source                  1..1169
                        mol_type = protein
                        organism = synthetic construct
SEQUENCE: 2
MEINNQNQCV PYNCLNNPES EILNVAIFSS EQVAEIHLKI TRLILENFLP GGSFAFGLFD  60
LIWGIFNEDQ WSAFLRQVEE LINQRITEFA RGQAIQRLVG FGRSYDEYIL ALKEWENDPD  120
NPASKERVRT RFRTTDDALL TGVPLMAIPG FELATLSVYA QSANLHLALL RDAVFFGERW  180
GLTQTNINDL YSRLKNSIRD YTNHCVRFYN IGLGNLNVIR PEYYRFQREL TISVLDLVAL  240
FPNYDIRTYP IPTKSQLTRE IYTDPIISPG AQAGYTLQDV LREPHLMDFL NRLIIYTGEY  300
RGIRHWAGHE VESSRTGMMT NIRFPLYGTA ATAEPTRFIT PSTFPGLNLF YRTLSAPIFR  360
DEPGANIIIR YRTSLVEGVG FIQPNNGEQL YRVRGTLDSL DQLPLEGESS LTEYSHRLCH  420
VRFAQSLRNA EPLDYARVPM FSWTHRSATP TNTIDPDVIT QIPLVKAFNL HSGATIVKGP  480
GFTGGDILRR TNVGSFGDMR VNITAPLSQR YRVRIRYAST TDLQFYTNIN GTTINIGNFS  540
STMDSGDDLQ YGRFRVAGFT TPFTFSDAMS TFTIGAFSFS SNNEVYIDRI EFVPAEVTFE  600
AEYDLEKAQK AVNALFTSSN QIGLKTDVTD YHIDKVSNLV ECLSDEFCLD EKRELSEKVK  660
HAKRLCDERN LLQDPNFRGI NRQPDRGWRG STDITIQGGD DVFKENYVTL PGTFDECYPT  720
YLYQKIDESK LKAYTRYELR GYIEDSQDLE IYLIRYNAKH ETVNVPGTGS LWPLSAQSPI  780
GKCGEPNRCA THLEWNPDLD CSCRDGEKCA HHSHHFSLDI DVGCTDLNED LGVWVIFKIK  840
TQDGHARLGN LEFLEEKPLV GEALARVKRA EKKWRDKREK LELETNIVYK EAKKSVDALF  900
VNSQYDRLQA DTNIAIIHAA DKRVHSIREA YLPELSVIPG VNAAIFEELE GRIFTAYSLY  960
DARNVIKNGD FNNGLSCWNV KGHVDVEEQN NHRSVLVVPE WEAEVSQEVR VCPGRGYILR  1020
VTAYKEGYGE GCVTIHEIED NTDELKFSNC VEEEIYPNNT VTCNDYTATQ EEYEGTYTSR  1080
NRGYDGAYES NSSVPADYAS AYEEKAYTDG RRDNTCESNR GYGDYTPLPA GYVTKELEYF  1140
PETDKVWIEI GETEGTFIVD SVELLLMEE                                    1169

SEQ ID NO: 3            moltype = AA  length = 1169
FEATURE                 Location/Qualifiers
REGION                  1..1169
                        note = Bt29-Bt22 chimeric protein.
source                  1..1169
                        mol_type = protein
                        organism = synthetic construct
SEQUENCE: 3
MEINNQNQCV PYNCLNNPES EILNVAIFSS EQVAEIHLKI TRLILENFLP GGSFAFGLFD  60
LIWGIFNEDQ WSAFLRQVEE LINQRITEFA RGQAIQRLVG FGRSYDEYIL ALKEWENDPD  120
NPASKERVRT RFRTTDDALL TGVPLMAIPG FELATLSVYA QSANLHLALL RDAVFFGERW  180
GLTQTNINDL YSRLKNSIRD YTNHCVRFYN IGLGNLNVIR PEYYRFQREL TISVLDLVAL  240
FPNYDIRTYP IPTKSQLTRE IYTDPIISPG AQAGYTLQDV LREPHLMDFL NRLIIYTGEY  300
RGIRHWAGHE VESSRTGMMT NIRFPLYGTA ATAEPTRFIT PSTFPGLNLF YRTLSAPIFR  360
DEPGANIIIR YRTSLVEGVG FIQPNNGEQL YRVRGTLDSL DQLPLEGESS LTEYSHRLCH  420
VRFAQSLRNA EPLDYARVPM FSWTHRSATP TNTIDPDVIT QIPLVKAHTL QSGTTVVKGP  480
GFTGGDILRR TSGGPFAFSN VNLDWNLSQR YRARIRYAST TNLRMYVTIA GERIFAGQFN  540
KTMNTGDPLT FQSFSYATID TAFTFPTKAS SLTVGADTFS SGNEVYVDRF ELIPVTATFE  600
AEYDLEKAQK AVNALFTSSN QIGLKTDVTD YHIDKVSNLV ECLSDEFCLD EKRELSEKVK  660
HAKRLCDERN LLQDPNFRGI NRQPDRGWRG STDITIQGGD DVFKENYVTL PGTFDECYPT  720
YLYQKIDESK LKAYTRYELR GYIEDSQDLE IYLIRYNAKH ETVNVPGTGS LWPLSAQSPI  780
GKCGEPNRCA THLEWNPDLD CSCRDGEKCA HHSHHFSLDI DVGCTDLNED LGVWVIFKIK  840
```

```
TQDGHARLGN LEFLEEKPLV GEALARVKRA EKKWRDKREK LELETNIVYK EAKKSVDALF   900
VNSQYDRLQA DTNIAIIHAA DKRVHSIREA YLPELSVIPG VNAAIFEELE GRIFTAYSLY   960
DARNVIKNGD FNNGLSCWNV KGHVDVEEQN NHRSVLVVPE WEAEVSQEVR VCPGRGYILR  1020
VTAYKEGYGE GCVTIHEIED NTDELKFSNC VEEEIYPNNT VTCNDYTATQ EEYEGTYTSR  1080
NRGYDGAYES NSSVPADYAS AYEEKAYTDG RRDNTCESNR GYGDYTPLPA GYVTKELEYF  1140
PETDKVWIEI GETEGTFIVD SVELLLMEE                                   1169

SEQ ID NO: 4               moltype = DNA   length = 3510
FEATURE                    Location/Qualifiers
misc_feature               1..3510
                           note = Coding sequencec for Bt29-Bt22 chimeric protein.
source                     1..3510
                           mol_type = other DNA
                           organism = synthetic construct
SEQUENCE: 4
atggagatta ataatcagaa ccaatgt -continued

```
misc_feature          1..3510
                      note = Maize optimized coding sequence for Bt29-Bt22
                       chimeric protein.
source                1..3510
                      mol_type = other DNA
                      organism = synthetic construct
SEQUENCE: 5
atggaaatca acaaccagaa ccagtgcgtg ccgtacaact gcctcaacaa ccccgagtcc  60
gagatcctga acgtggccat cttctccagc gagcaggtcg cggagatcca cctcaagatc  120
acgcgcctga tcctcgagaa cttcctgccg ggcggctcct tcgctttcgg cctgttcgac  180
ctcatctggg gcatcttcaa cgaggaccag tggagcgcgt tcctcaggca ggtggaggag  240
ctgatcaacc agcgcatcac ggagttcgcc aggggccagg ctatccagcg gctggtgggc  300
ttcggcaggt cctacgacga atacatcctg gccctcaagg agtgggagaa cgaccccgac  360
aacccggcca gcaaggagcg cgtgaggacc cgcttcagga ccaccgacga cgctctcctg  420
acgggcgtcc ccctcatggc tatcccgggc ttcgagctgg ccaccctctc ggtgtacgct  480
cagtcggcca acctgcacct cgccctcctg cgggacgctg tgttcttcgg cgagaggtgg  540
ggcctgaccc aaaccaacat caacgacctc tactccaggc tgaagaacag catccgcgac  600
tacacgaacc actgcgtgcg cttctacaac atcggcctgg gcaacctcaa cgtcatcagg  660
ccggaatact accgcttcca gagggagctg accatcagcg tgctggacct cgtcgccctg  720
ttccccaact acgacatccg cacgtacccg atccccacca agtcccagct cacgagggag  780
atctacaccg acccgatcat ctcgccgggc gcccaggccg gctacaccct gcaggacgtc  840
ctgagggagc cccacctgat ggacttcctg aacaggctca tcatctacac cggcgagtac  900
aggggcatca ggcactgggc gggccacgag gtggagtcca gcaggacggg catgatgacc  960
aacatccgct tcccgctcta cggcaccgcg gccacggccg agccaacccg cttcatcacg  1020
ccgtccacct tccccggcct gaacctcttc tacaggaccc tgtcggctcc catcttccgc  1080
gacgagccgg gcgcgaacat catcatccgc tacaggacct ccctcgtgga gggcgtcggc  1140
ttcatccagc cgaacaacgg cgagcagctg taccgcgtga ggggcacgct ggacagcctg  1200
gaccagctcc cactggaggg cgagtccagc ctcaccgagt actcgcacag gctgtgccac  1260
gtcaggttcg cccagagcct caggaacgcg gagcccctgg actacgccag ggtgcccatg  1320
ttcagctgga cccacaggtc ggctaccccc accaacacca tcgacccaga cgtgatcacg  1380
cagatcccgc tcgtcaaggc ccacaccctg cagtcgggca ccaccgtggt caagggcccc  1440
ggcttcacgg gcggcgacat cctgaggagg acctccggcg gcccattcgc cttcagcaac  1500
gtcaacctcg actggaacct gtcccagcgc tacagggcgc gcatcaggta cgccagcacc  1560
acgaacctgc gcatgtatgt gaccatcgcg ggcgagagga tcttcgccgg ccagttcaac  1620
aagacgatga acaccggcga cccgctcacc ttccagtcct tcagctacgc gacgatcgac  1680
accgccttca cgttccccac gaaggcctcc agcctgaccg tgggcgccga caccttctcc  1740
agcggcaacg aggtctacgt ggaccgcttc gagctgatcc cggtgacggc gaccttcgag  1800
gccgagtacg acctggagaa ggcccagaag gcggtcaacg ccctcttcac ctccagcaac  1860
cagatcggcc tgaagacgga cgtgaccgac taccacatcg acaaggtgtc caacctcgtc  1920
gagtgcctga gcgacgagtt ctgcctcgac gagaagaggg agctgtccga gaaggtcaag  1980
cacgccaagc gcctctgcga cgagaggaac ctcctgcagg acccgaactt caggggcatc  2040
aaccgccagc cggacagggg ctggaggggc agcaccgaca tcaccatcca gggcggcgac  2100
gacgtgttca aggagaacta cgtcacgctc ccgggcacct tcgacgagtg ctaccccacg  2160
tacctgtacc agaagatcga cgagtccaag ctcaaggcct acacccgcta cgagctgagg  2220
ggctacatcg aggacagcca ggacctcgag atctacctga tccgctacaa cgcgaagcac  2280
gagacggtga acgtccccgg cacgggctcc ctgtggcccc tctcggctca gtcgccgatc  2340
ggcaagtgcg gcgagcccaa caggtgcgcc acccacctcg agtggaaccc ggacctggac  2400
tgctcctgcc gggacggcga gaagtgcgct caccactccc accacttcag cctggacatc  2460
gacgtgggct gcacggacct caacgaggac ctgggcgtgt gggtcatctt caagatcaag  2520
acgcaggacg gccacgctag gctgggcaac ctcgagttcc tggaggagaa gccgctggtg  2580
ggcgaggctc tggccagggt caagagggcg gagaagaagt ggcgcgacaa gagggagaag  2640
ctggagctgg agacgaacat cgtctacaag gaggccaaga agtccgtgga cgcgctcttc  2700
gtcaacagcc agtacgacag gctgcaggcg gacaccaaca tcgccatcat ccacgccgcg  2760
gacaagcgcg tgcactccat cagggaggcc tacctccccg agctgagcgt gatcccgggc  2820
gtcaacgctg ccatcttcga ggagctggag ggccgcatct tcaccgccta ctccctgtac  2880
gacgcgagga acgtcatcaa gaacggcgac ttcaacaacg gcctcagctg ctggaacgtg  2940
aagggccacg tggacgtcga ggagcagaac aaccaccgct cggtgctggt ggtccccgag  3000
tgggaggctg aggtcagcca ggaggtgcgc gtctgcccgg gcaggggcta catcctccgc  3060
gtgaccgcgt acaaggaggg ctacggcgag ggctgcgtca cgatccacga gatcgaggac  3120
aacaccgacg agctgaagtt ctccaactgc gtggaggagg agatctaccc gaacaacacg  3180
gtcacctgca acgactacac ggccacccag gaggagtacg agggcacgta cacgtcgagg  3240
aacaggggct acgacggcgc ttacgagtcc aacagctcgg tgccggccga ctacgctagc  3300
gcgtacgagg agaaggccta cacggacggc cgcagggaca acacctgcga gtcgaacagg  3360
ggctacggcg actacacgcc gctcccggcc ggctacgtga ccaaggagct ggagtacttc  3420
ccggagacgg acaaggtctg gatcgagatc ggcgagacgg agggcacctt catcgtggac  3480
agcgtcgagc tgctgctcat ggaggagtag                                   3510

SEQ ID NO: 6          moltype = DNA  length = 3510
FEATURE               Location/Qualifiers
misc_feature          1..3510
                      note = Maize optimized coding sequence for BT29-BT22
                       cimeric protein.
source                1..3510
                      mol_type = other DNA
                      organism = synthetic construct
SEQUENCE: 6
atggaaatca acaaccagaa ccagtgcgtg ccgtacaact gccttaacaa ccccgagtcc  60
gagatcctga acgtggccat cttctccagc gagcaggtcg cggagatcca cctcaagatc  120
acgcgcctga tcctcgagaa cttcctgccg ggcggctcct tcgctttcgg cctgttcgac  180

```
ctcatctggg gcatcttcaa cgaggaccag tggagcgcgt tcctcaggca ggtggaggag  240
ctgatcaacc agcgcatcac ggagttcgcc aggggccagg ctatccagcg gctggtgggc  300
ttcggcaggt cctacgacga atacatcctg gccctcaagg agtgggagaa cgaccccgac  360
aacccggcca gcaaggagcg cgtgaggacc cgcttcagga ccaccgacga cgctctcctg  420
acgggcgtcc ccctcatggc tatcccgggc ttcgagctgg ccaccctctc ggtgtacgct  480
cagtcggcca acctgcacct cgccctcctg cgggacgctg tgttcttcgg cgagaggtgg  540
ggcctgaccc aaaccaacat caacgacctc tactccaggc tgaagaacag catccgcgac  600
tacacgaacc actgcgtgcg cttctacaac atcggcctgg gcaacctcaa cgtcatcagg  660
ccggaatact accgcttcca gagggagctg accatcagcg tgctggacct cgtcgccctg  720
ttccccaact acgacatccg cacgtacccg atccccacca agtcccagct cacgagggag  780
atctacaccg acccgatcat ctcgccgggc gcccaggccg gctacaccct gcaggacgtc  840
ctgagggagc cccacctgat ggacttcctg aacaggctca tcatctacac cggcgagtac  900
aggggcatca ggcactgggc gggccacgag gtggagtcca gcaggacggg catgatgacc  960
aacatccgct tcccgctcta cggcaccgcg gccacggccg agccaacccg cttcatcacg  1020
ccgtccacct tccccggcct gaacctcttc tacaggaccc tgtcggctcc catcttccgc  1080
gacgagccgg gcgcgaacat catcatccgc tacaggacct ccctcgtgga gggcgtcggc  1140
ttcatccagc cgaacaacgg cgagcagctg taccgcgtga ggggcacgct ggacagcctg  1200
gaccagctcc cactggaggg cgagtccagc ctcaccgagt actcgcacag gctgtgccac  1260
gtcaggttcg cccagagcct caggaacgcg gagcccctgg actacgccag ggtgcccatg  1320
ttcagctgga cccacaggtc ggctaccccc accaacacca tcgacccaga cgtgatcacg  1380
cagatcccgc tcgtcaaggc ccacaccctg cagtcgggca ccaccgtggt caagggcccc  1440
ggcttcacgg gcggcgacat cctgaggagg acctccggcg gcccattcgc cttcagcaac  1500
gtcaacctcg actggaacct gtcccagcgc tacagggcgc gcatcaggta cgccagcacc  1560
acgaacctgc gcatgtatgt gaccatcgcg ggcgagagga tcttcgccgg ccagttcaac  1620
aagacgatga acaccggcga cccgctcacc ttccagtcct tcagctacgc gacgatcgac  1680
accgccttca cgttccccac gaaggcctcc agcctgaccg tgggcgccga caccttctcc  1740
agcggcaacg aggtctacgt ggaccgcttc gagctgatcc cggtgacggc gaccttcgag  1800
gccgagtacg acctggagaa ggcccagaag gcggtcaacg ccctcttcac ctccagcaac  1860
cagatcggcc tgaagacgga cgtgaccgac taccacatcg acaaggtgtc caacctcgtc  1920
gagtgcctga gcgacgagtt ctgcctcgac gagaagaggg agctgtccga gaaggtcaag  1980
cacgccaagc gcctctgcga cgagaggaac ctcctgcagg acccgaactt caggggcatc  2040
aaccgccagc cggacagggg ctggaggggc agcaccgaca tcaccatcca gggcggcgac  2100
gacgtgttca aggagaacta cgtcacgctc ccgggcacct tcgacgagtg ctaccccacg  2160
tacctgtacc agaagatcga cgagtccaag ctcaaggcct acacccgcta cgagctgagg  2220
ggctacatcg aggacagcca ggacctcgag atctacctga tccgctacaa cgcgaagcac  2280
gagacggtga acgtccccgg cacgggctcc ctgtggcccc tctcggctca gtcgccgatc  2340
ggcaagtgcg gcgagcccaa caggtgcgcc acccacctcg agtggaaccc ggacctggac  2400
tgctcctgcc gggacggcga gaagtgcgct caccactccc accacttcag cctggacatc  2460
gacgtgggct gcacggacct caacgaggac ctgggcgtgt gggtcatctt caagatcaag  2520
acgcaggacg gccacgctag gctgggcaac ctcgagttcc tggaggagaa gccgctggtg  2580
ggcgaggctc tggccagggt caagagggcg gagaagaagt ggcgcgacaa gagggagaag  2640
ctggagctgg agacgaacat cgtctacaag gaggccaaga agtccgtgga cgcgctcttc  2700
gtcaacagcc agtacgacag gctgcaggcg gacaccaaca tcgccatcat ccacgccgcg  2760
gacaagcgcg tgcactccat cagggaggcc tacctccccg agctgagcgt gatcccgggc  2820
gtcaacgctg ccatcttcga ggagctggag ggccgcatct tcaccgccta ctccctgtac  2880
gacgcgagga acgtcatcaa gaacggcgac ttcaacaacg gcctcagctg ctggaacgtg  2940
aagggccacg tggacgtcga ggagcagaac aaccaccgct cggtgctggt ggtccccgag  3000
tgggaggctg aggtcagcca ggaggtgcgc gtctgcccgg gcaggggcta catcctccgc  3060
gtgaccgcgt acaaggaggg ctacggcgag ggctgcgtca cgatccacga gatcgaggac  3120
aacaccgacg agctgaagtt ctccaactgc gtggaggagg agatctaccc gaacaacacg  3180
gtcacctgca acgactacac ggccacccag gaggagtacg agggcacgta cacgtcgagg  3240
aacaggggct acgacggcgc ttacgagtcc aacagctcgg tgccggccga ctacgctagc  3300
gcgtacgagg agaaggccta cacggacggc cgcagggaca acacctgcga gtcgaacagg  3360
ggctacggcg actacacgcc gctcccggcc ggctacgtga ccaaggagct ggagtacttc  3420
ccggagacgg acaaggtctg gatcgagatc ggcgagacgg agggcacctt catcgtggac  3480
tcagtcgagc tgctgctcat ggaggagtag                                  3510
```

```
SEQ ID NO: 7            moltype = DNA  length = 3510
FEATURE                 Location/Qualifiers
misc_feature            1..3510
                        note = Maize optimized coding sequence for Bt29-Bt22
                         chimeric protein.
source                  1..3510
                        mol_type = other DNA
                        organism = synthetic construct
SEQUENCE: 7
atggagatca acaaccagaa ccagtgcgtg ccgtacaact gccttaacaa ccccgagtcc  60
gagatcctga acgtggccat cttctccagc gagcaggtcg cggagatcca cctcaagatc  120
acgcgcctga tcctcgagaa cttcctgccc ggcggctcct tcgctttcgg cctgttcgac  180
ctcatctggg gcatcttcaa cgaggaccag tggagcgcgt tcctcaggca ggtggaggag  240
ctgatcaacc agcgcatcac ggagttcgcc aggggccagg ctatccagcg gctggtgggc  300
ttcggcaggt cctacgacga gtacatcctg gccctcaagg agtgggagaa cgaccccgac  360
aacccggcca gcaaggagcg cgtgaggacc cgcttcagga ccaccgacga cgctctcctg  420
acgggcgtcc ccctcatggc tatcccgggc ttcgagctgg ccaccctctc ggtgtacgct  480
cagtcggcca acctgcacct cgccctcctg cgggacgctg tgttcttcgg cgagaggtgg  540
ggcctgaccc agacgaacat caacgacctc tactccaggc tgaagaacag catccgcgac  600
tacacgaacc actgcgtgcg cttctacaac atcggcctgg gcaacctcaa cgtcatcagg  660
ccggagtact accgcttcca gagggagctg accatcagcg tgctggacct cgtcgccctg  720
ttccccaact acgacatccg cacgtacccg atcccaacca agtcccagct cacgagggag  780
```

```
atctacaccg acccgatcat ctcgccgggc gcccaggccg gctacaccct gcaggacgtc   840
ctgagggagc cccacctgat ggacttcctg aacaggctca tcatctacac cggcgagtac   900
aggggcatca ggcactgggc gggccacgag gtggagtcca gcaggacggg catgatgacc   960
aacatccgct tcccgctcta cggcaccgcg gccacggccg agccaacccg cttcatcacg  1020
ccgtccacct ccccggcct gaacctcttc tacaggaccc tgtcggctcc catcttccgc   1080
gacgagccgg gcgcgaacat catcatccgc tacaggacct ccctcgtgga gggcgtcggc  1140
ttcatccagc cgaacaacgg cgagcagctg taccgcgtga ggggcacgct ggacagcctg  1200
gaccagctcc cactggaggg cgagtccagc ctcaccgagt actcgcacag gctgtgccac  1260
gtcaggttcg cccagagcct caggaacgcg gagcccctgg actacgcgg ggtgcccatc  1320
ttcagctgga cccacaggtc ggctaccccc accaaccaca cgacccagag cgtgatcacg  1380
cagatcccgc tcgtcaaggc ccacaccctg cagtcgggca ccaccgtggt caagggcccc  1440
ggcttcacgg cgcgacat cctgaggagg acctccggcg gccattcgc cttcagcaac  1500
gtcaacctcg actggaacct gtcccagcgc tacagggcgc gcatcaggta cgccagcacc  1560
acgaacctgc gcatgtatgt gaccatcgcg ggcgagagga tcttcgccgg ccagttcaac  1620
aagacgatga acaccggcga cccgctcacc ttccagtcct tcagctacgc gacgatcgac  1680
accgccttca cgttccccac gaaggcctcc agcctgaccg tgggcgccga cacctttctcc  1740
agcggcaacg aggtctacgt ggaccgcttc gagctgatcc cggtgacggc gaccttcgag  1800
gccgagtacg acctggagaa ggcccagaag cgggtcaacg ccctcttcac ctccagcaac  1860
cagatcggcc tgaagacgga cgtgaccgac taccacatcg acaaggtgtc caacctcgtc  1920
gagtgcctga cgacgagtt ctgcctcgac gagaagaggg agctgtccga aaggtcaag  1980
cacgccaagc gcctctgcga cgagaggaac ctcctgcagg acccgaactt caggggaatc  2040
aaccgccagc cggacagggg ctggagggc agcaccatcca gggcggcgac  2100
gacgtgttca aggagaacta cgtcacgctc ccgggcacct cgacgagtg ctaccccacg  2160
tacctgtacc agaagatcga cgagtccaag ctcaaggcct acaccccgcta cgagctgagg  2220
ggatacatcg aggacagcca ggacctcgag atctacctga tccgctacaa cgcgaagcac  2280
gagacggtca acgtccccgg cacgggctcc ctgtggcccc tctcggctca gtcgccagtc  2340
ggcaagtgcg gcgagcccaa caggtgcgcc acccactcc agtggaaccc ggacctggac  2400
tgctcctgcc gggacggcga gaagtgcgct caccactccc accacttcag cctggacatc  2460
gacgtgggct gcacggacct caacgaggac ctggcgtgt gggtcatctt caaaatcaag  2520
acgcaggacg gccacgctag gctgagttcc tggaggagaa gcccgctggtg  2580
ggcgaggctc tggccagggt caagagggcg gagaagaagt ggcgcgacaa gagggagaag  2640
ctggagctgg agacgaacat cgtctacaag gaggccaaga gtccgtggaa cgcgctcttc  2700
gtcaacagcc agtacgacag gctgcaggcg gacaccaaca tcgccatcat ccacgccgcg  2760
gacaagcgcg tgcactccat cagggaggcc tacctccccg agctgagcgt gatccggggc  2820
gtcaacgctg ccatcttcga ggagctggag ggccgcatct tcaccgccta ctccctgtac  2880
gacgcgagga acgtcatcaa gaacggcgac ttcaacaacg gcctcagctg ctggaacgtg  2940
aagggccacg tggacgtcga ggagcagaac aaccaccgct cggtgctggt ggtccccgag  3000
tgggaggctg aggtcagcca ggaggtgcgc gtctgcccgg gcaggggata catcctccgc  3060
gtgaccgcgt acaaggaggg ctacggcgag ggctgcgtca cgatccacga gatcgaggac  3120
aacaccgacg agctgaagtt ctccaactgc gtggaggagg agatctaccc gaacaacacg  3180
gtcacctgca cgactacac ggccacccag gaggagtacg agggcacgta cacgtcgagg  3240
aacagggggt acgacggcgc ttacgagtcc aacagctcgg tgccggccga ctacgctagc  3300
gcgtacgagg agaaggccta cacggacggc gcaggggaca acacctgcga gtcgaacagg  3360
ggctacggcg actacacgcc gctcccggcc ggctacgtga ccaaggagct ggagtacttc  3420
ccggagacgg acaaggtctg gatcgagatc ggcgagacgg agggcacctt catcgtggac  3480
tcagtcgagc tgctgctcat ggaggagtag                                     3510
```

SEQ ID NO: 8          moltype = AA  length = 1174
FEATURE               Location/Qualifiers
source                1..1174
                      mol_type = protein
                      organism = Bacillus thuringiensis
SEQUENCE: 8

```
MENNIQNQCV PYNCLNNPEV EILNEERSTG RLPLDISLSL TRFLLSEFVP GVGVAFGLFD    60
LIWGFITPSD WSLFLLQIEQ LIEQRIETLE RNRAITTLRG LADSYEIYIE ALREWEANPN   120
NAQLREDVRI RFANTDDALI TAINNFTLTS FEIPLLSVYV QAANLHLSLL RDAVSFGQGW   180
GLDIATVNNH YNRLINLIHR YTKHCLDTYN QGLENLRGTN TRQWARFNQF RRDLTLTVLD   240
IVALFPNYDV RTYPIQTSSQ LTREIYTSSV IEDSPVSANI PNGFNRAEFG VRPPHLMDFM   300
NSLFVTAETV RSQTVWGGHL VSSRNTAGNR INFPSYGVFN PGGAIWIADE DPRPFYRTLS   360
DPVFVRGGFG NPHYVLGLRG VAFQQTGTNH TRTFRNSGTI DSLDEIPPQD NSGAPWNDYS   420
HVLNHVTFVR WPGEISGSDS WRAPMFSWTH RSATPTNTID PERITQIPLV KAHTLQSGTT   480
VVRGPGFTGG DILRRTSGGP FAYTIVNING QLPQRYRARI RYASTTNLRI YVTVAGERIF   540
AGQFNKTMDT GDPLTFQSFS YATINTAFTF PMSQSSFTVG ADTFSSGNEV YIDRFELIPV   600
TATFEAEYDL ERAQKAVNAL FTSINQIGIK TDVTDYHIDQ VSNLVDCLSD EFCLDEKREL   660
SEKVKHAKRL SDERNLLQDP NFKGINRQLD RGWRGSDIT IQRGDDVFKE NYVTLPGTFD    720
ECYPTYLYQK IDESKLKPYT RYQLRGYIED SQDLEIYLIR YNAKHETVNV LGTGSLWPLS   780
VQSPIRKCGE PNRCAPHLEW NPDLDCSCRD GEKCAHHSHH FSLDIDVGCT DLNEDLDVVV   840
IFKIKTQDGH ARLGNLEFLE EKPLVGEALA RVKRAEKKWR DKREKLELET NIVYKEAKES   900
VDALFVNSQY DQLQADTNIA MIHAADKRVH RIREAYLPEL SVIPGVNVDI FEELKGRIFT   960
AFFLYDARNV IKNGDFNNGL SCWNVKGHVD VEEQNNHRSV LVVPEWEAEV SQEVRVCPGR  1020
GYILRVTAYK EGYGEGCVTI HEIENNTDEL KFSNCVEEEV YPNNTVTCND YTANQEEYGG  1080
AYTSRNRGYD ETYGSNSSVP ADYASVYEEK SYTDGRRDNP CESNRGYGDY TPLPAGYVTK  1140
ELEYFPETDK VWIEIGETEG TFIVDSVELL LMEE                              1174
```

SEQ ID NO: 9          moltype = AA  length = 1169
FEATURE               Location/Qualifiers
REGION                1..1169
                      note = Engineered BT29-Cry1Fa1 chimeric protein.

| source | 1..1169 |
| --- | --- |
| | mol_type = protein |
| | organism = synthetic construct |

SEQUENCE: 9

```
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVRGP   480
GFTGGDILRR TSGGPPAYTI VNINGQLPQR YRARIRYAST TNLRIYVTVA GERIFAGQFN   540
KTMDTGDPLT FQSFSYATIN TAFTFPMSQS SFTVGADTFS SGNEVYIDRF ELIPVTATFE   600
AEYDLEKAQK AVNALFTSSN QIGLKTDVTD YHIDKVSNLV ECLSDEFCLD EKRELSEKVK   660
HAKRLCDERN LLQDPNFRGI NRQPDRGWRG STDITIQGGD DVFKENYVTL PGTFDECYPT   720
YLYQKIDESK LKAYTRYELR GYIEDSQDLE IYLIRYNAKH ETVNVPGTGS LWPLSAQSPI   780
GKCGEPNRCA THLEWNPDLD CSCRDGEKCA HHSHHFSLDI DVGCTDLNED LGVWVIFKIK   840
TQDGHARLGN LEFLEEKPLV GEALARVKRA EKKWRDKREK LELETNIVYK EAKKSVDALF   900
VNSQYDRLQA DTNIAIIHAA DKRVHSIREA YLPELSVIPG VNAAIFEELE GRIFTAYSLY   960
DARNVIKNGD FNNGLSCWNV KGHVDVEEQN NHRSVLVVPE WEAEVSQEVR VCPGRGYILR  1020
VTAYKEGYGE GCVTIHEIED NTDELKFSNC VEEEIYPNNT VTCNDYTATQ EEYEGTYTSR  1080
NRGYDGAYES NSSVPADYAS AYEEKAYTDG RRDNTCESNR GYGDYTPLPA GYVTKELEYF  1140
PETDKVWIEI GETEGTFIVD SVELLLMEE                                   1169
```

| SEQ ID NO: 10 | moltype = DNA   length = 3510 |
| --- | --- |
| FEATURE | Location/Qualifiers |
| misc_feature | 1..3510 |
| | note = BT29-Cry1Fa1 coding sequence. |
| source | 1..3510 |
| | mol_type = other DNA |
| | organism = synthetic construct |

SEQUENCE: 10

```
atggagatta ataatcagaa ccaatgtgtc ccttataatt gtttgaataa tcctgaaagc     60
gagatattaa acgttgcaat ttttagtagc gaacaggtag cagaaattca cttaaagatc    120
acgcgcttaa ttttagagaa ttttttacca ggtgggagtt ttgcattcgg cttatttgat    180
ttaatatggg ggattttcaa tgaagatcaa tggagcgcat tcttcggca ggtagaagaa    240
ttaattaatc aaaggataac ggaattcgca agagggcaag caattcagag actagtaggg    300
tttggagtga gttatgatga atatatttta gcactaaaag aatgggaaaa cgatcctgat    360
aacccagctt caaaggaaag agtgcgcact cgatttcgga caactgatga tgccttgcta    420
accggtgttc ctcttatggc aattccaggt tttgaattag ctactttatc tgtttatgct    480
caatcagcca atctacattt agcccctata agagatgctg tatttttttgg ggagagatgg    540
ggattgacac aaacaaatat aaatgattta tatagtagat taaaaaactc cattcgtagt   600
tatacaaatc attgtgttcg ttttttataat ataggtttag ggaatttaaa tgttataaga    660
ccagagtatt accgtttcca aagagaatta acaatatctg tcttagatct tgtagctctt    720
ttttccaaatt acgatatccg aacatatcca ataccaacta aaagtcaatt aacaagagaa    780
atttatacag atccgattat ttcacctggt gcacaggcag gttatactct tcaagatgtt    840
ttgagagaac cacaccttat ggacttttta aaccgactta ttatttatac tggtgagtat    900
cgcggaattc gtcactgggc aggacatgaa gtagaatcta gtagaacagg tatgatgact    960
aatataagat ttccttgta tggaacagcc gcaacagcag aaccaacacg tttataact   1020
cctagtactt ttcctggtct taatttattt tatagaacat tatcagctcc tatttttag   1080
gatgaaccgg gagctaatat tattattaga tatagaacga gtttggtgga aggagtagga   1140
tttattcaac aaataacgg tgaacagctt tacagagtga gaggaacatt agattctctt   1200
gatcaattac cacttgaggg tgagagtagt ctaactgaat atagtcatcg attatgccat   1260
gttagatttg cgcaatcatt gaggaatgca gaaccttag attatgcaag ggttccgatg   1320
ttttcttgga cacatcgtag tgcaacccct acaaatacaa ttgatccaga tgtcatcacc   1380
caaatacccgt tagtaaaagc acatacactt cagtcaggta ctactgttgt aagagggccc   1440
gggtttacgg gaggagatat tcttcgacga caagtggagg gaccatttgc ttatactatt   1500
gttaatataa atgggcaatt accccaaagg tatcgtgca gaatacgcta tgcctctact   1560
acaaatctaa gaatttacgt aacggttgca ggtgaacgga ttttttgctgg tcaatttaac   1620
aaaacaatgg ataccggtga cccattaaca ttccaatctt ttagttacgc aactattaat   1680
acagctttta cattcccaat gagccagagt agtttcacag taggtgctga tacttttagt   1740
tcagggaatg aagtttatat agacagattt gaattgattc cagttactgc aacatttgag   1800
gcagaaatatg atttagaaa agctcagaaa gcggtgaatg cgctgtttac ttcttccaat   1860
caaatcgggt taaaaacaga tgtgacggac tatcatattg ataaagtatc caatctagtt   1920
gagtgtttat cagatgaatt ttgtctagat gaaaagcgag aattgtccga aaagtcaaa   1980
catgcgaagc gactctgtga tgagcggaat ttacttcaag atccaaactt cagaggcatc   2040
aatagacaac cagaccgtgg ttggagagga agtacgatca ttaccatcca aggaggagat   2100
gacgtattca agagaattac gttacgcta ccgggtacct ttgatgagtg ctatccacg   2160
tatttatatc aaaaaatag atgagtcgaaa ttaaaagcct ataccgcta tgaattaaga   2220
gggtatatcg aggatagtca agacttgaa atctattta ttcgctacaa tgcaaaacat   2280
gaaacagtaa atgtgccagg tacgggtccc ttatggccgc tttcagccca agtccaatc   2340
ggaaagtgtg gagaaccgaa tcgatgtgcg acacaccttg aatggaatcc tgacttagat   2400
tgttgtcgta gggatggaga aaagtgtgca catcattgcg catcatttct cttagacatt   2460
gatgtaggat gtacagacct aaatgaggac ctaggtgtat gggtgatctt taagattaag   2520
acgcaagatg tcatgcgag actaggaaat ctagaatttc gaagagaa accattagta   2580
ggagaagcgc tagctcgtgt gaagagagcg gagaaaaaat ggagagacaa acgcgaaaaa   2640
ttggaattgg aaacaaatat tgtttataaa gaggcaaaaa aatctgtaga tgcttttttt   2700
gtgaactctc aatatgatag attacaagcg gatacgaata tcgcgataat tcatgcggca   2760
```

-continued

```
gataaacgcg ttcatagcat tcgagaagca tatcttccag agttgtctgt aattccgggt  2820
gtaaatgcag ctatttttga agaattagag ggacgtattt tcacagccta ctctctatat  2880
gatgcgagaa atgtcattaa aaatggcgat ttcaataatg gcttatcatg ctggaacgtg  2940
aaagggcatg tagatgtaga agaacagaac aaccatcgtt cggtccttgt tgttccagaa  3000
tgggaagcag aagtgtcaca agaggttcgt gtctgtccag gtcgtggcta tatccttcgt  3060
gttacagcgt acaaagaggg atatggagag ggctgtgtaa cgattcatga gatcgaagac  3120
aatacagacg aactgaaatt cagcaactgt gtagaagagg aaatatatcc aaacaacacg  3180
gtaacgtgta atgattatac tgcgactcaa gaagaatatg agggtacgta cacttctcgt  3240
aatcgaggat atgacggagc ctatgaaagc aattcttctg taccagctga ttatgcatca  3300
gcctatgaag aaaaagcgta tacagatgga agaagagaca atacttgtga atctaacaga  3360
ggatatgggg attacacacc actaccagct ggctatgtga caaaagaatt agagtacttc  3420
ccagaaaccg ataaggtatg gattgagatt ggagaaacgg aaggaacatt tatcgtggac  3480
agcgtggaat tactccttat ggaggaatag                                    3510

SEQ ID NO: 11          moltype = DNA  length = 3510
FEATURE                Location/Qualifiers
misc_feature           1..3510
                       note = Maize optimized BT29-Cry1Fa1 coding sequence.
source                 1..3510
                       mol_type = other DNA
                       organism = synthetic construct
SEQUENCE: 11
atggaaatca acaaccagaa ccagtgcgtg ccgtacaact gcctcaacaa ccccgagtcc  60
gagatcctga acgtggccat cttctccagc gagcaggtcg cggagatcca cctcaagatc  120
acgcgcctga tcctcgagaa cttcctgccg ggcggctcct tcgctttcgg cctgttcgac  180
ctcatctggg gcatcttcaa cgaggaccag tggagcgcgt tcctcaggca ggtggaggag  240
ctgatcaacc agcgcatcac ggagttcgcc aggggccagg ctatccagcg gctggtgggc  300
ttcggcaggt cctacgacga atacatcctg gccctcaagg agtgggagaa cgaccccgac  360
aacccggcca gcaaggagcg cgtgaggacc cgcttcagga ccaccgacga cgctctcctg  420
acgggcgtcc ccctcatggc tatcccgggc ttcgagctgg ccaccctctc ggtgtacgct  480
cagtcggcca acctgcacct cgccctcctg cgggacgctg tgttcttcgg cgagaggtgg  540
ggcctgaccc aaaccaacat caacgacctc tactccaggc tgaagaacag catccgcgac  600
tacacgaacc actgcgtgcg cttctacaac atcggcctgg gcaacctcaa cgtcatcagg  660
ccggaatact accgcttcca gagggagctg accatcagcg tgctggacct cgtcgccctg  720
ttccccaact acgacatccg cacgtacccg atccccacca agtcccagct cacgagggag  780
atctacaccg acccgatcat ctcgccgggc gcccaggccg gctacaccct gcaggacgtc  840
ctgagggagc cccacctgat ggacttcctg aacaggctca tcatctacac cggcgagtac  900
aggggcatca ggcactgggc gggccacgag gtggagtcca gcaggacggg catgatgacc  960
aacatccgct tcccgctcta cggcaccgcg gccacggccg agccaacccg cttcatcacg  1020
ccgtccacct tccccggcct gaacctcttc tacaggaccc tgtcggctcc catcttccgc  1080
gacgagccgg gcgcgaacat catcatccgc tacaggacct ccctcgtgga gggcgtcggc  1140
ttcatccagc cgaacaacgg cgagcagctg taccgcgtga ggggcacgct ggacagcctg  1200
gaccagctcc cactggaggg cgagtccagc ctcaccgagt actcgcacag gctgtgccac  1260
gtcaggttcg cccagagcct caggaacgcg gagcccctgg actacgccag ggtgcccatg  1320
ttcagctgga cccacaggtc ggctaccccc accaacacca tcgacccaga cgtgatcacg  1380
cagatcccgc tcgtcaaggc ccacaccctg cagtcgggca ccaccgtggt ccgcggccca  1440
ggcttcaccg gcggcgacat cctgaggagg acgagcggcg gccccttcgc ttacaccatc  1500
gtcaacatca acggccagct gccacagagg tacagggcgc gcatcaggta cgcctccacc  1560
acgaacctgc gcatctacgt gaccgtggcg ggcgagagga tcttcgccgg ccagttcaac  1620
aagacgatgg acaccggcga cccgctgacc ttccagtcct tcagctacgc gacgatcaac  1680
accgccttca cgttccccat gagccagtcc agcttcaccg tgggcgccga cacgttctcc  1740
agcggcaacg aggtgtacat cgaccgcttc gagctgatcc cggtgacggc gaccttcgag  1800
gccgagtacg acctggagaa ggcccagaag gcggtcaacg ccctcttcac ctccagcaac  1860
cagatcggcc tgaagacgga cgtgaccgac taccacatcg acaaggtgtc caacctcgtc  1920
gagtgcctga gcgacgagtt ctgcctcgac gagaagaggg agctgtccga gaaggtcaag  1980
cacgccaagc gcctctgcga cgagaggaac ctcctgcagg acccgaactt caggggcatc  2040
aaccgccagc cggacagggg ctggaggggc agcaccgaca tcaccatcca gggcggcgac  2100
gacgtgttca aggagaacta cgtcacgctc ccgggcacct tcgacgagtg ctaccccacg  2160
tacctgtacc agaagatcga cgagtccaag ctcaaggcct acacccgcta cgagctgagg  2220
ggctacatcg aggacagcca ggacctcgag atctacctga tccgctacaa cgcgaagcac  2280
gagacggtga acgtccccgg cacgggctcc ctgtggcccc tctcggctca gtcgccgatc  2340
ggcaagtgcg gcgagcccaa caggtgcgcc acccacctcg agtggaaccc ggacctggac  2400
tgctcctgcc gggacggcga gaagtgcgct caccactccc accacttcag cctggacatc  2460
gacgtgggct gcacggacct caacgaggac ctgggcgtgt gggtcatctt caagatcaag  2520
acgcaggacg gccacgctag gctgggcaac ctcgagttcc tggaggagaa gccgctggtg  2580
ggcgaggctc tggccagggt caagagggcg gagaagaagt ggcgcgacaa gagggagaag  2640
ctggagctgg agacgaacat cgtctacaag gaggccaaga agtccgtgga cgcgctcttc  2700
gtcaacagcc agtacgacag gctgcaggcg gacaccaaca tcgccatcat ccacgccgcg  2760
gacaagcgcg tgcactccat cagggaggcc tacctccccg agctgagcgt gatcccgggc  2820
gtcaacgctg ccatcttcga ggagctggag ggccgcatct tcaccgccta ctccctgtac  2880
gacgcgagga acgtcatcaa gaacggcgac ttcaacaacg gcctcagctg ctggaacgtg  2940
aagggccacg tggacgtcga ggagcagaac aaccaccgct cggtgctggt ggtccccgag  3000
tgggaggctg aggtcagcca ggaggtgcgc gtctgcccgg gcaggggcta catcctccgc  3060
gtgaccgcgt acaaggaggg ctacggcgag ggctgcgtca cgatccacga gatcgaggac  3120
aacaccgacg agctgaagtt ctccaactgc gtggaggagg agatctaccc gaacaacacg  3180
gtcacctgca acgactacac ggccacccag gaggagtacg agggcacgta cacgtcgagg  3240
aacaggggct acgacggcgc ttacgagtcc aacagctcgg tgccggccga ctacgctagc  3300
gcgtacgagg agaaggccta cacggacggc cgcagggaca acacctgcga gtcgaacagg  3360
ggctacggcg actacacgcc gctcccggcc ggctacgtga ccaaggagct ggagtacttc  3420
```

-continued ccggagacgg acaaggtctg gatcgagatc ggcgagacgg agggcacctt catcgtggac 3480
agcgtcgagc tgctgctcat ggaggagtag 3510

SEQ ID NO: 12 moltype = AA length = 1215
FEATURE Location/Qualifiers
source 1..1215
mol_type = protein
organism = Bacillus thuringiensis
SEQUENCE: 12
MNSNRKNENE IINALSIPAV SNHSAQMDLS PDARIEDSLC VAEGNNIDPF VSASTVQTGI 60
SIAGRILGVL GVPFAGQLAS FYSFLVGELW PSGRDPWEIF MEHVEQIVRQ QQITDSVRDT 120
AIARLEGLGR GYRSYQQALE TWLDNRNDAR SRSIIRERYI ALELDITTAI PLFSIRNEEV 180
PLLMVYAQAA NLHLLLLRDA SLFGSEWGMS SADVNQYYQE QIRYTEEYSN HCVQWYNTGL 240
NRLRGTTAET WVRYNQFRRD LTLGVLDLVA LFPSYDTRTY PIPTTAQLTR EVYTDPNGVV 300
AGPNNSWFRN GASFSAIENA IIRQPHLYDF LTNLTIYTRR SQVGTTIMNL WAGHRITFNR 360
IQGGSTSEMV YGAITNPVSV SDIPFVNRDV YRTVSLAGGL GSLSGIRYGL TRVDFDMIFR 420
NHPDIVTGLF YHPGHAGIAT QVKDSDTELP PETTEQPNYR AFSHLLSHIS MGPTTQDVPP 480
VYSWTHQSAD RTNTINSDRI TQIPLVKAHT LQSGTTVVKG PGFTGGDILR RTSGGPFAFS 540
NVNLDFNLSQ RYRARIRYAS TTNLRIYVTV AGERIFAGQF DKTMDAGAPL TFQSFSYATI 600
NTAFTFPERS SSLTIGADTF SSGNEVYVDR FELIQVTATF EAESDLERAR KAVNALFTST 660
NPRGLKTDVT DYHIDQVSNL VECLSDEFCL DKKRELLEEV KYAKRLSDER NLLQDPTFTS 720
ISGQTDRGWI GSTGISIQGG DDIFKENYVR LPGTVDECYP TYLYQKIDES QLKSYTRYQL 780
RGYIEDSQDL EIYLIRYNAK HETLSVPGTE SPWPSSGVYP SGRCGEPNRC APRIEWNPDL 840
DCSCRYGEKC VHHSHHFSLD IDVGCTDLNE DLGVWVIFKI KTQDGHAKLG NLEFIEEKPL 900
LGKALSRVKR AEKKWRDKYE KLQLETKRVY TEAKESVDAL FVDSQYDKLQ ANTNIGIIHG 960
ADKQVHRIRE PYLSELPVIP SINAAIFEEL EGHIFKAYSL YDARNVIKNG DFNNGLSCWN 1020
VKGHVDVQQN HHRSVLVLSE WEAEVSQKVR VCPDRGYILR VTAYKEGYGE GCVTIHEFED 1080
NTDVLKFRNF VEEEVYPNNT VTCNDYTTNQ SAEGSTDACN SYNRGYEDGY ENRYEPNPSA 1140
PVNYTPTYEE GMYTDTQGYN HCVSDRGYRN HTPLPAGYVT LELEYFPETE QVWIEIGETE 1200
GTFIVGSVEL LLMEE 1215

SEQ ID NO: 13 moltype = AA length = 1169
FEATURE Location/Qualifiers
REGION 1..1169
note = Engineered BT29-Cry1Ka1 chimeric protein.
source 1..1169
mol_type = protein
organism = synthetic construct
SEQUENCE: 13
MEINNQNQCV PYNCLNNPES EILNVAIFSS EQVAEIHLKI TRLILENFLP GGSFAFGLFD 60
LIWGIFNEDQ WSAFLRQVEE LINQRITEFA RGQAIQRLVG FGRSYDEYIL ALKEWENDPD 120
NPASKERVRT RFRTTDDALL TGVPLMAIPG FELATLSVYA QSANLHLALL RDAVFFGERW 180
GLTQTNINDL YSRLKNSIRD YTNHCVRFYN IGLGNLNVIR PEYYRFQREL TISVLDLVAL 240
FPNYDIRTYP IPTKSQLTRE IYTDPIISPG AQAGYTLQDV LREPHLMDFL NRLIIYTGEY 300
RGIRHWAGHE VESSRTGMMT NIRFPLYGTA ATAEPTRFIT PSTFPGLNLF YRTLSAPIFR 360
DEPGANIIIR YRTSLVEGVG FIQPNNGEQL YRVRGTLDSL DQLPLEGESS LTEYSHRLCH 420
VRFAQSLRNA EPLDYARVPM FSWTHRSATP TNTIDPDVIT QIPLVKAHTL QSGTTVVKGP 480
GFTGGDILRR TSGGPFAFSN VNLDFNLSQR YRARIRYAST TNLRIYVTVA GERIFAGQFD 540
KTMDAGAPLT FQSFSYATIN TAFTFPERSS SLTIGADTFS SGNEVYVDRF ELIQVTATFE 600
AEYDLEKAQK AVNALFTSSN QIGLKTDVTD YHIDKVSNLV ECLSDEFCLD EKRELSEKVK 660
HAKRLCDERN LLQDPNFRGI NRQPDRGWRG STDITIQGGD DVFKENYVTL PGTFDECYPT 720
YLYQKIDESK LKAYTRYELR GYIEDSQDLE IYLIRYNAKH ETVNVPGTGS LWPLSAQSPI 780
GKCGEPNRCA THLEWNPDLD CSCRDGEKCA HHSHHFSLDI DVGCTDLNED LGVWVIFKIK 840
TQDGHARLGN LEFLEEKPLV GEALARVKRA EKKWRDKREK LELETNIVYK EAKKSVDALF 900
VNSQYDRLQA DTNIAIIHAA DKRVHSIREA YLPELSVIPG VNAAIFEELE GRIFTAYSLY 960
DARNVIKNGD FNNGLSCWNV KGHVDVEEQN NHRSVLVVPE WEAEVSQEVR VCPGRGYILR 1020
VTAYKEGYGE GCVTIHEIED NTDELKFSNC VEEEIYPNNT VTCNDYTATQ EEYEGTYTSR 1080
NRGYDGAYES NSSVPADYAS AYEEKAYTDG RRDNTCESNR GYGDYTPLPA GYVTKELEYF 1140
PETDKVWIEI GETEGTFIVD SVELLLMEE 1169

SEQ ID NO: 14 moltype = DNA length = 3510
FEATURE Location/Qualifiers
misc_feature 1..3510
note = BT29-Cry1Ka1 coding sequence.
source 1..3510
mol_type = other DNA
organism = synthetic construct
SEQUENCE: 14
atggagatta ataatcagaa ccaatgtgtc ccttataatt gtttgaataa tcctgaaagc 60
gagatattaa acgttgcaat ttttagtagc gaacaggtag cagaaattca cttaaagatc 120
acgcgcttaa ttttagagaa ttttttacca ggtgggagtt ttgcattcgg cttatttgat 180
ttaatatggg ggatttttaa tgaagatcaa tggagcgcat ttcttcggca ggtagaagaa 240
ttaattaatc aaaggataac ggaattcgca agagggcaag caattcagag actagtaggg 300
tttggaagga gttatgatga atatatttta gcactaaaag aatgggaaaa cgatcctgat 360
aacccagctt caaaggaaag agtgcgcact cgatttcgga caactgatga tgccttgcta 420
accggtgttc ctcttatggc aattccaggt tttgaattag ctactttatc tgtttatgct 480
caatcagcca atctacattt agccctatta agagatgctg tattttttgg ggagagatgg 540
ggattgacac aaacaaatat aaatgattta tatagtagat taaaaaactc cattcgtgat 600
tatacaaatc attgtgttcg tttttataat ataggtttag ggaatttaaa tgttataaga 660

-continued

```
ccagagtatt accgtttcca aagagaatta acaatatctg tcttagatct tgtagctctt  720
tttccaaatt acgatatccg aacatatcca ataccaacta aaagtcaatt aacaagagaa  780
atttatacag atccgattat ttcacctggt gcacaggcag gttatactct tcaagatgtt  840
ttgagagaac cacaccttat ggacttttta aaccgactta ttatttatac tggtgagtat  900
cgcggaattc gtcactgggc aggacatgaa gtagaatcta gtagaacagg tatgatgact  960
aatataagat ttcctttgta tggaacagcc gcaacagcag aaccaacacg atttataact  1020
cctagtactt ttcctggtct taatttattt tatagaacat tatcagctcc tatttttaga  1080
gatgaaccgg gagctaatat tattattaga tatagaacga gtttggtgga aggagtagga  1140
tttattcaac caaataacgg tgaacagctt tacagagtga gaggaacatt agattctctt  1200
gatcaattac cacttgaggg tgagagtagt ctaactgaat atagtcatcg attatgccat  1260
gttagatttg cgcaatcatt gaggaatgca gaacctttag attatgcaag ggttccgatg  1320
ttttcttgga cacatcgtag tgcaacccct acaaatacaa ttgatccaga tgtcatcacc  1380
caaataccgt tagtaaaggc gcataccctc caatcgggta caactgtagt aaaagggcca  1440
gggtttacag gaggggatat cctccgtcga acaagtggag gaccatttgc ttttagtaat  1500
gttaatctag attttaactt gtcacaaagg tatcgtgcta gaattcgtta tgcctctact  1560
actaacctaa gaatttacgt aacggttgca ggtgaacgaa tttttgctgg tcaatttgac  1620
aaaacgatgg atgctggtgc cccattaaca ttccaatctt ttagttacgc aactattaat  1680
acagctttta cattcccaga aagatcgagc agcttgacta taggtgccga tacgtttagt  1740
tcaggtaatg aagtttatgt agatagattt gaattaatcc aagttactgc aacatttgag  1800
gcagaatatg atttagagaa agctcagaaa gcggtgaatg cgctgtttac ttcttccaat  1860
caaatcgggt taaaaacaga tgtgacggac tatcatattg ataaagtatc caatctagtt  1920
gagtgtttat cagatgaatt ttgtctagat gaaaagcgag aattgtccga gaaagtcaaa  1980
catgcgaagc gactctgtga tgagcggaat ttacttcaag atccaaactt cagaggcatc  2040
aatagacaac cagaccgtgg ttggagagga agtacggata ttaccatcca aggaggagat  2100
gacgtattca aagagaatta cgttacgcta ccgggtacct ttgatgagtg ctatccaacg  2160
tatttatatc aaaaaataga tgagtcgaaa ttaaaagcct atacccgcta tgaattaaga  2220
gggtatatcg aggatagtca agacttagaa atctatttaa ttcgctacaa tgcaaaacat  2280
gaaacagtaa atgtgccagg tacgggttcc ttatggccgc tttcagccca aagtccaatc  2340
ggaaagtgtg gagaaccgaa tcgatgtgcg acacaccttg aatggaatcc tgacttagat  2400
tgttcgtgta gggatggaga aaagtgtgcc catcattcgc atcatttctc cttagacatt  2460
gatgtaggat gtacagacct aaatgaggac ctaggtgtat gggtgatctt taagattaag  2520
acgcaagatg gtcatgcgag actaggaaat ctagaatttc tcgaagagaa accattagta  2580
ggagaagcgc tagctcgtgt gaagagagcg gagaaaaaat ggagagacaa acgcgaaaaa  2640
ttggaattgg aaacaaatat tgtttataaa gaggcaaaaa aatctgtaga tgctttattt  2700
gtgaactctc aatatgatag attacaagcg gatacgaata tcgcgataat tcatgcggca  2760
gataaacgcg ttcatagcat tcgagaagca tatcttccag agttgtctgt aattccgggt  2820
gtaaatgcag ctattttttga agaattagag ggacgtattt tcacagccta ctctctatat  2880
gatgcgagaa atgtcattaa aaatggcgat ttcaataatg gcttatcatg ctggaacgtg  2940
aaagggcatg tagatgtaga agaacagaac aaccatcgtt cggtccttgt tgttccagaa  3000
tgggaagcag aagtgtcaca agaggttcgt gtctgtccag gtcgtggcta tatccttcgt  3060
gttacagcgt acaaagaggg atatggagag ggctgtgtaa cgattcatga gatcgaagac  3120
aatacagacg aactgaaatt cagcaactgt gtagaagagg aaatatatcc aaacaacacg  3180
gtaacgtgta atgattatac tgcgactcaa gaagaatatg agggtacgta cacttctcgt  3240
aatcgaggat atgacggagc ctatgaaagc aattcttctg taccagctga ttatgcatca  3300
gcctatgaag aaaaagcgta tacagatgga agaagagaca atacttgtga atctaacaga  3360
ggatatgggg attacacacc actaccagct ggctatgtga caaaagaatt agagtacttc  3420
ccagaaaccg ataaggtatg gattgagatt ggagaaacgg aaggaacatt tatcgtggac  3480
agcgtggaat tactccttat ggaggaatag                                   3510

SEQ ID NO: 15          moltype = AA  length = 1169
FEATURE                Location/Qualifiers
REGION                 1..1169
                       note = Bt29-1Kav2 chimeric protein
source                 1..1169
                       mol_type = protein
                       organism = synthetic construct
SEQUENCE: 15
MEINNQNQCV PYNCLNNPES EILNVAIFSS EQVAEIHLKI TRLILENFLP GGSFAFGLFD  60
LIWGIFNEDQ WSAFLRQVEE LINQRITEFA RGQAIQRLVG FGRSYDEYIL ALKEWENDPD  120
NPASKERVRT RFRTTDDALL TGVPLMAIPG FELATLSVYA QSANLHLALL RDAVFFGERW  180
GLTQTNINDL YSRLKNSIRD YTNHCVRFYN IGLGNLNVIR PEYYRFQREL TISVLDLVAL  240
FPNYDIRTYP IPTKSQLTRE IYTDPIISPG AQAGYTLQDV LREPHLMDFL NRLIIYTGEY  300
RGIRHWAGHE VESSRTGMMT NIRFPLYGTA ATAEPTRFIT PSTFPGLNLF YRTLSAPIFR  360
DEPGANIIIR YRTSLVEGVG FIQPNNGEQL YRVRGTLDSL DQLPLEGESS LTEYSHRLCH  420
VRFAQSLRNA EPLDYARVPM FSWTHRSATP TNTIDPDVIT QIPLVKAHTL QSGTTVVKGP  480
GFTGGDILRR TSGGPFAFSN VNLDFNLSQR YRARIRYAST TNLRIYVTVA GERIFAGQFD  540
KTMDAGAPLT FQSFSYATIN TAFTFPERSS SLTIGADTFS SGNEVYVDRF ELIQVTATFE  600
AESDLERARK AVNALFTSSN QIGLKTDVTD YHIDKVSNLV ECLSDEFCLD EKRELSEKVK  660
HAKRLCDERN LLQDPNFRGI NRQPDRGWRG STDITIQGGD DVFKENYVTL PGTFDECYPT  720
YLYQKIDESK LKAYTRYELR GYIEDSQDLE IYLIRYNAKH ETVNVPGTGS LWPLSAQSPI  780
GKCGEPNRCA THLEWNPDLD CSCRDGEKCA HHSHHFSLDI DVGCTDLNED LGVWVIFKIK  840
TQDGHARLGN LEFLEEKPLV GEALARVKRA EKKWRDKREK LELETNIVYK EAKKSVDALF  900
VNSQYDRLQA DTNIAIIHAA DKRVHSIREA YLPELSVIPG VNAAIFEELE GRIFTAYSLY  960
DARNVIKNGD FNNGLSCWNV KGHVDVEEQN NHRSVLVVPE WEAEVSQEVR VCPGRGYILR  1020
VTAYKEGYGE GCVTIHEIED NTDELKFSNC VEEEIYPNNT VTCNDYTATQ EEYEGTYTSR  1080
NRGYDGAYES NSSVPADYAS AYEEKAYTDG RRDNTCESNR GYGDYTPLPA GYVTKELEYF  1140
PETDKVWIEI GETEGTFIVD SVELLLMEE                                    1169

SEQ ID NO: 16          moltype = DNA  length = 3510
```

```
FEATURE              Location/Qualifiers
misc_feature         1..3510
                     note = Bt29-1Ka chimera
source               1..3510
                     mol_type = other DNA
                     organism = synthetic construct
SEQUENCE: 16
atggagatta ataatcagaa ccaatgtgtc cctataatt gtttgaataa tcctgaaagc    60
gagatattaa acgttgcaat ttttagtagc gaacaggtag cagaaattca cttaaagatc   120
acgcgcttaa ttttagaaga tttttacca ggtgggagtt ttgcattcgg cttatttgat    180
ttaatatggg ggattttaa tgaagatcaa tggagcgcat tcttcggca ggtagaagaa     240
ttaattaatc aaaggataac ggaattcgca agagggcaag caattcagag actagtaggg   300
tttggaagga gttatgatga atatatttta gcactaaaag aatgggaaaa cgatcctgat   360
aacccagctt caaaggaaag agtgcgcact cgatttcgga caactgatga tgccttgcta   420
accggtgttc ctcttatggc aattccaggt tttgaattag ctactttatc tgtttatgct   480
caatcagcca atctacattt agccctatta gagatgctg tattttttgg ggagagatgg    540
ggattgacac aaacaaatat aaatgattta tatagtagat taaaaactc cattcgtgat    600
tatacaaatc attgtgttcg tttttataat ataggtttga ggaatttaaa tgttataaga   660
ccagagtatt accgtttcca aagagaatta acaatatctg tcttagatct tgtagctctt   720
tttcaaaatt acgatatccg aacatatcca ataccaacta aaagtcaatt aacaagagaa   780
atttatacag atccgattat ttcacctggt gcacaggcag gttatactct tcaagatgtt   840
ttgagagaac cacacctat ggacttttta aaccgactta ttatttatac tggtgagtat    900
cgcggaattc gtcactgggc aggacatgaa gtagaatcta gtagaacagg tatgatgact   960
aatataagat ttcctttgta tggaacagcc gcaacagcag aaccaacacg atttataact  1020
cctagtactt ttcctggtct taatttattt tatagaacat tatcagctcc tatttttaga  1080
gatgaaccgg gagctaatat tattattaga taaagacaa gttggtggaa aggagtagaa   1140
tttattcaac caaataacgg tgaacagctt tacagagtga gaggaacatt agattctctt  1200
gatcaattac cacttgaggg tgagagtagt ctaactgaat atagtcatcg attatgccat  1260
gttagatttg cgcaatcatt gaggaatgca gaacctttag attatgcaag ggttccgatg  1320
ttttcttgga cacatcgtag tgcaaccct acaaataca ttgatccaga tgtcatcacc    1380
caaataccgt tagtaaaagc acataccctt cagtcaggta ctactgttgt aaaagggcca  1440
gggtttacag gtgagatat cctccgacga actagtggag gaccattgc ttttagtaat   1500
gttaatttag actttaactt gtcacaaaga tatcgtgcta gaatacgcta tgcttctact  1560
actaatctaa gaatttacgt aacggtagca ggggaacgaa ttttttgctgg tcaatttgat  1620
aaaacaatgg atgcaggtgc accattaaca ttccaatctt ttagttacgc aactattaat  1680
acagcatttta cattcccaga aagaagtagc agcttgacta ttggtgctga tactttttagc  1740
tcaggtaatg aagtttatgt agatagattt gaattgatcc aggttactgc aacatttgag  1800
gcagaatcag atttagagag agcacgaaaa gcggtgaatg cgctgtttac ttcttccaat  1860
caaatcgggt taaaaacaga tgtgacggac tatcatattg ataaagtatc caatctagtt  1920
gagtgtttat cagatgaatt ttgtctagat gaaaagcgag aattgtccga gaaagtcaaa  1980
catgcgaagc gactctgtga tgagcggaat ttacttcaag atccaaactt cagaggcatc  2040
aatagacaac cagaccgtgg ttggagagga agtacggata ttaccatcca aggaggagat  2100
gacgtattca aagagaatta cgttacgcta ccgggtacct ttgatgagtg ctatccaacg  2160
tatttatatc aaaaaataga tgagtcgaaa ttaaaagcct atacccgcta tgaattaaga  2220
gggtatatcg aggatagtca agacttagaa atctattaa ttcgctacaa tgcaaaacat   2280
gaaacagtaa atgtgccagg tacgggttcc ttatggccgc tttcagccca aagtccaatc  2340
ggaaagtgtg gagaaccgaa tcgatgtgcg acacaccttg aatggaatcc tgacttagat  2400
tgttcgtgta gggatggaga aaagtgtgcc catcattcgc atcatttctc cttagacatt  2460
gatgtaggat gtacagacct aaatgaggac ctaggtgtat gggtgatctt taagattaag  2520
acgcaagatg gtcatgcgag actaggaaat ctagaatttc tcgaagagaa accattagta  2580
ggagacgcgc tagctcgtgt gaagagagcg gagaaaaaat ggagagacaa acgcgaaaaa  2640
ttggaattgg aaacaaatat tgttataaa gaggcaaaaa aatctgtaga tgctttattt  2700
gtgaactctc aatatgatag attacaagcg gatacgaata tcgcgataat tcatgcggca  2760
gataaacgcg ttcatagcat tcgagaagca tatcttccag agttgtctgt aattccgggt  2820
gtaaatgcag ctattttttga agaattagag ggacgtattt tcacagccta ctctctatat  2880
gatgcgagaa atgtcattaa aaatggcgat ttcaataatg gcttatcatg ctggaacgtg  2940
aaagggcatg tagatgtaga agaacagaac aaccatcgtt cggtccttgt tgttccagaa  3000
tgggaagcag aagtgtcaca agaggttcgt gtctgtccag tcgtggcta tatccttcgt  3060
gttacagcgt acaaagagg tatgagaga ggctgtgtaa cgattcatga cgtcgaagac  3120
aatacagacg aactgaaatt cagcaactgt gtagaagagg aaatatatcc aaacaacacg  3180
gtaacgtgta atgattatac tgcgactcaa gaagaatatg agggtacgta cacttctcgt  3240
aatcgaggat atgacggagc ctatgaaagc aattcttctg taccagctga ttatgcatca  3300
gcctatgaag aaaaagcgta tacagatgga agaagagaca atacttgtga atctaacaga  3360
ggatatgggg attacacacc actaccagct ggctatgtga caaagaatt agagtacttc  3420
ccagaaaccg ataaggtatg gattgagatt ggagaaacg aaggaacatt tatcgtgaac  3480
agcgtggaat tactccttat ggaggaatag                                    3510

SEQ ID NO: 17          moltype = AA  length = 1189
FEATURE                Location/Qualifiers
source                 1..1189
                       mol_type = protein
                       organism = Bacillus thuringiensis
SEQUENCE: 17
MEENNQNQCI PYNCLSNPEE VLLDGERIST GNSSIDISLS LVQFLVSNFV PGGGFLVGLI    60
DFVWGIVGPS QWDAFLVQIE QLINERIAEF ARNAAIANLE GLGNNFNIYV EAFKEWEEDP   120
NNPATRTRVI DRFRILDGLL ERDIPSFRIS GFEVPLLSVY AQAANLHLAI LRDSVIFGER   180
WGLTTINVNE NYNRLIRHID EYADHCANTY NRGLNNLPKS TYQDWITYNR LRRDLTLTVL   240
DIAAFFPNYD NRRYPIQPVG QLTREVYTDP LINFNPQLQS VAQLPTFNVM ESSAIRNPHL   300
FDILNNLTIF TDWFSVGRNF YWGGHRVISS LIGGGNITSP IYGREANQEP PRSFTFNGPV   360
```

-continued

```
FRTLSNPTLR LLQQPWPAPP FNLRGVEGVE FSTPTNSFTY RGRGTVDSLT ELPPEDNSVP  420
PREGYSHRLC HATFVQRSGT PFLTTGVVFS WTHRSATLTN TIDPERINQI PLVKGFRVWG  480
GTSVITGPGF TGGDILRRNT FGDFVSLQVN INSPITQRYR LRFRYASSRD ARVIVLTGAA  540
STGVGGQVSV NMPLQKTMEI GENLTSRTFR YTDFSNPFSF RANPDIIGIS EQPLFGAGSI  600
SSGELYIDKI EIILADATFE AESDLERAQK AVNALFTSSN QIGLKTDVTD YHIDQVSNLV  660
DCLSDEFCLD EKRELSEKVK HAKRLSDERN LLQDPNFRGI NRQPDRGWRG STDITIQGGD  720
DVFKENYVTL PGTVDECYPT YLYQKIDESK LKAYTRYELR GYIEDSQDLE IYLIRYNAKH  780
EIVNVPGTGS LWPLSAQSPI GKCGEPNRCA PHLEWNPDLD CSCRDGEKCA HHSHHFTLDI  840
DVGCTDLNED LGVWVIFKIK TQDGHARLGN LEFLEEKPLL GEALARVKRA EKKWRDKREK  900
LQLETNIVYK EAKESVDALF VNSQYDRLQV DTNIAMIHAA DKRVHRIREA YLPELSVIPG  960
VNAAIFEELE GRIFTAYSLY DARNVIKNGD FNNGLLCWNV KGHVDVEEQN NHRSVLVIPE  1020
WEAEVSQEVR VCPGRGYILR VTAYKEGYGE GCVTIHEIED NTDELKFSNC VEEEVYPNNT  1080
VTCNNYTGTQ EEYEGTYTSR NQGYDEAYGN NPSVPADYAS VYEEKSYTDG RRENPCESNR  1140
GYGDYTPLPA GYVTKDLEYF PETDKVWIEI GETEGTFIVD SVELLLMEE             1189

SEQ ID NO: 18          moltype = AA  length = 1181
FEATURE                Location/Qualifiers
REGION                 1..1181
                       note = Engineered Bt29-1Ca chimeric protein.
source                 1..1181
                       mol_type = protein
                       organism = synthetic construct
SEQUENCE: 18
MEINNQNQCV PYNCLNNPES EILNVAIFSS EQVAEIHLKI TRLILENFLP GGSFAFGLFD  60
LIWGIFNEDQ WSAFLRQVEE LINQRITEFA RGQAIQRLVG FGRSYDEYIL ALKEWENDPD  120
NPASKERVRT RFRTTDDALL TGVPLMAIPG FELATLSVYA QSANLHLALL RDAVFFGERW  180
GLTQTNINDL YSRLKNSIRD YTNHCVRFYN IGLGNLNVIR PEYYRFQREL TISVLDLVAL  240
FPNYDIRTYP IPTKSQLTRE IYTDPIISPG AQAGYTLQDV LREPHLMDFL NRLIIYTGEY  300
RGIRHWAGHE VESSRTGMMT NIRFPLYGTA ATAEPTRFIT PSTFPGLNLF YRTLSAPIFR  360
DEPGANIIIR YRTSLVEGVG FIQPNNGEQL YRVRGTLDSL DQLPLEGESS LTEYSHRLCH  420
VRFAQSLRNA EPLDYARVPM FSWTHRSATP TNTIDPDVIT QIPLVKGFRV WGGTSVITGP  480
GFTGGDILRR NTFGDFVSLQ VNINSPITQR YRLRFRYASS RDARVIVLTG AASTGVGGQV  540
SVNMPLQKTM EIGENLTSRT FRYTDFSNPF SFRANPDIIG ISEQPLFGAG SISSGELYID  600
KIEIILADAT FEAEYDLEKA QKAVNALFTS SNQIGLKTDV TDYHIDKVSN LVECLSDEFC  660
LDEKRELSEK VKHAKRLCDE RNLLQDPNFR GINRQPDRGW RGSTDITIQG GDDVFKENYV  720
TLPGTFDECY PTYLYQKIDE SKLKAYTRYE LRGYIEDSQD LEIYLIRYNA KHETVNVPGT  780
GSLWPLSAQS PIGKCGEPNR CATHLEWNPD LDCSCRDGEK CAHHSHHFSL DIDVGCTDLN  840
EDLGVWVIFK IKTQDGHARL GNLEFLEEKP LVGEALARVK RAEKKWRDKR EKLELETNIV  900
YKEAKKSVDA LFVNSQYDRL QADTNIAIIH AADKRVHSIR EAYLPELSVI PGVNAAIFEE  960
LEGRIFTAYS LYDARNVIKN GDFNNGLSCW NVKGHVDVEE QNNHRSVLVV PEWEAEVSQE  1020
VRVCPGRGYI LRVTAYKEGY GEGCVTIHEI EDNTDELKFS NCVEEEIYPN NTVTCNDYTA  1080
TQEEYEGTYT SRNRGYDGAY ESNSSVPADY ASAYEEKAYT DGRRDNTCES NRGYGDYTPL  1140
PAGYVTKELE YFPETDKVWI EIGETEGTFI VDSVELLLME E                     1181

SEQ ID NO: 19          moltype = DNA  length = 3546
FEATURE                Location/Qualifiers
misc_feature           1..3546
                       note = Bt29-1Ca chimera
source                 1..3546
                       mol_type = other DNA
                       organism = synthetic construct
SEQUENCE: 19
atggagatta ataatcagaa ccaatgtgtc ccttataatt gtttgaataa tcctgaaagc  60
gagatattaa acgttgcaat ttttagtagc gaacaggtag cagaaattca cttaaagatc  120
acgcgcttaa ttttagagaa ttttttacca ggtgggagtt ttgcattcgg cttatttgat  180
ttaatatggg ggatttttaa tgaagatcaa tggagcgcat ttcttcggca ggtagaagaa  240
ttaattaatc aaaggataac ggaattcgca agagggcaag caattcagag actagtaggg  300
tttggaagga gttatgatga atatatttta gcactaaaag aatgggaaaa cgatcctgat  360
aacccagctt caaaggaaag agtgcgcact cgatttcgga caactgatga tgccttgcta  420
accggtgttc ctcttatggc aattccaggt tttgaattag ctactttatc tgtttatgct  480
caatcagcca atctacattt agccctatta agagatgctg tatttttggg ggagagatgg  540
ggattgacac aaacaaatat aaatgattta tatagtagat taaaaaactc cattcgtgat  600
tatacaaatc attgtgttcg tttttataat ataggtttag ggaatttaaa tgttataaga  660
ccagagtatt accgtttcca aagagaatta acaatatctg tcttagatct tgtagctctt  720
tttccaaatt acgatatccg aacatatcca ataccaacta aaagtcaatt aacaagagaa  780
atttatacag atccgattat ttcacctggt gcacaggcag gttatactct tcaagatgtt  840
ttgagagaac cacaccttat ggacttttta aaccgactta ttatttatac tggtgagtat  900
cgcggaattc gtcactgggc aggacatgaa gtagaatcta gtagaacagg tatgatgact  960
aatataagat ttcctttgta tggaacagcc gcaacagcag aaccaacacg atttataact  1020
cctagtactt ttcctggtct taatttattt tatagaacat tatcagctcc tatttttaga  1080
gatgaaccgg gagctaatat tattattaga tatagaacga gtttggtgga aggagtagga  1140
tttattcaac caaataacgg tgaacagctt tacagagtga gaggaacatt agattctctt  1200
gatcaattac cacttgaggg tgagagtagt ctaactgaat atagtcatcg attatgccat  1260
gttagatttg cgcaatcatt gaggaatgca gaacctttag attatgcaag ggttccgatg  1320
ttttcttgga cacatcgtag tgcaacccct acaaatacaa ttgatccaga tgtcatcacc  1380
caaataccgc tggtgaaagg ctttcgcgtg tggggcggca ccagcgtgat taccggcccg  1440
ggctttaccg gcggcgatat tctgcgccgc aacacctttg gcgattttgt gagcctgcag  1500
gtgaacatta acagcccgat tacccagcgc tatcgcctgc gctttcgcta tgcgagcagc  1560
cgcgatgcgc gcgtgattgt gctgaccggc gcggcgagca ccggcgtggg cggccaggtg  1620
```

```
agcgtgaaca tgccgctgca gaaaaccatg gaaattggcg aaaacctgac cagccgcacc   1680
tttcgctata ccgattttag caacccgttt agctttcgcg cgaacccgga tattattggc   1740
attagcgaac agccgctgtt tggcgcgggc agcattagca gcggcgaact gtatattgat   1800
aaaattgaaa ttattctggc ggatgcgaca tttgaggcag aatatgattt agagaaagct   1860
cagaaagcgg tgaatgcgct gtttacttct ccaatcaatc tcgggttaaa aacagatgtg   1920
acggactatc atattgataa agtatccaat ctagttgagt gtttatcaga tgaattttgt   1980
ctagatgaaa agcgagaatt gtccgagaaa gtcaaacatg cgaagcgact ctgtgatgag   2040
cggaatttac ttcaagatcc aaacttcaga ggcatcaata gacaaccaga ccgtggttgg   2100
agaggaagta cggatattac catccaagga gggagatgta tattcaaaga gaattacgtt   2160
acgctaccgg gtacctttga tgagtgctat ccaacgtatt tatatcaaaa aatagatgag   2220
tcgaaattaa aagcctatac ccgctatgaa ttaagagggt atatcgagga tagtcaagac   2280
ttagaaatct atttaattcg ctacaatgca aaacatgaaa cagtaaatgt gccaggtacg   2340
ggttccttat ggccgctttc agcccaaagt ccaatcggaa agtgtggaga accgaatcga   2400
tgtcgacac accttgaatg gaatcctgac ttagattgtt cgtgtaggga tggagaaaag   2460
tgtgccatc attcgcatca tttctcctta gacattgatg taggatgtac agacctaaat   2520
gaggacctag gtgtatgggt gatctttaag attaagacgc aagatggtca tgcgagacta   2580
ggaaatctag aatttctcga agagaaacca ttagtaggaa agcgctagc tcgtgtgaag   2640
agagcggaga aaaattggag agacaaacgc gaaaaattgg aattggaaac aaatattgtt   2700
tataaagagg caaaaaaatc tgtagatgct ttatttgtga actctcaata tgatagatta   2760
caagcggata cgaatatcgc gataattcat gcggcagata aacgcgttca tagcattcga   2820
gaagcatatc ttccagagtt gtctgtaatt ccgggtgtaa atgcagctat ttttgaagaa   2880
ttagagggac gtattttcac agcctactct ctatatgatg cgagaaatgt cattaaaaat   2940
ggcgatttca ataatggctt atcatgctgt aacgtgaaag gcatgtaga tgtagaagaa   3000
cagaacaacc atcgttcggt ccttgttgtt ccagaatggg aagcagaagt gtcacaagag   3060
gttcgtgtct gtccaggtcg tggctatatc cttcgtgtta cagcgtacaa agagggatat   3120
ggagagggct gtgtaacgat tcatgagatc gaagacaata cagacgaact gaaattcagc   3180
aactgtgtag aagaggaaat atatccaaac aacacggtaa cgtgtaatga ttatactgcg   3240
actcaagaag aatatgaggg tacgtacact tctcgtaatc gaggatatga cggagcctat   3300
gaaagcaatt cttctgtacc agctgattat gcatcagcct atgaagaaaa agcgtataca   3360
gatggaagaa gagacaatac ttgtgaatct aacagaggat atggggatta cacaccacta   3420
ccagctggct atgtgacaaa agaattagag tacttcccag aaaccgataa ggtatggatt   3480
gagattggag aaacggaagg aacatttatc gtggacagcg tggaattact ccttatggag   3540
gaatag                                                              3546

SEQ ID NO: 20          moltype = AA   length = 652
FEATURE                Location/Qualifiers
REGION                 1..652
                       note = Bt29-Bt22Tr1
source                 1..652
                       mol_type = protein
                       organism = synthetic construct
SEQUENCE: 20
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVKGP   480
GFTGGDILRR TSGGPPAFSN VNLDWNLSQR YRARIRYAST TNLRMYVTIA GERIFAGQFN   540
KTMNTGDPLT FQSFSFYATID TAFTFPTKAS SLTVGADTFS SGNEVYVDRF ELIPVTATFE   600
AEYDLEKAQK AVNALFTSSN QIGLKTDVTD YHIDKVSNLV ECLSDEFCLD EK            652

SEQ ID NO: 21          moltype = AA   length = 636
FEATURE                Location/Qualifiers
REGION                 1..636
                       note = Bt29-Bt22Tr2
source                 1..636
                       mol_type = protein
                       organism = synthetic construct
SEQUENCE: 21
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVKGP   480
GFTGGDILRR TSGGPPAFSN VNLDWNLSQR YRARIRYAST TNLRMYVTIA GERIFAGQFN   540
KTMNTGDPLT FQSFSFYATID TAFTFPTKAS SLTVGADTFS SGNEVYVDRF ELIPVTATFE   600
AEYDLEKAQK AVNALFTSSN QIGLKTDVTD YHIDKV                             636

SEQ ID NO: 22          moltype = AA   length = 622
FEATURE                Location/Qualifiers
REGION                 1..622
                       note = Bt29-Bt22Tr3

```
source                      1..622
                            mol_type = protein
                            organism = synthetic construct
SEQUENCE: 22
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVKGP   480
GFTGGDILRR TSGGPFAFSN VNLDWNLSQR YRARIRYAST TNLRMYVTIA GERIFAGQFN   540
KTMNTGDPLT FQSFSYATID TAFTFPTKAS SLTVGADTFS SGNEVYVDRF ELIPVTATFE   600
AEYDLEKAQK AVNALFTSSN QI                                           622

SEQ ID NO: 23               moltype = AA  length = 610
FEATURE                     Location/Qualifiers
REGION                      1..610
                            note = Bt29-Bt22Tr4
source                      1..610
                            mol_type = protein
                            organism = synthetic construct
SEQUENCE: 23
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVKGP   480
GFTGGDILRR TSGGPFAFSN VNLDWNLSQR YRARIRYAST TNLRMYVTIA GERIFAGQFN   540
KTMNTGDPLT FQSFSYATID TAFTFPTKAS SLTVGADTFS SGNEVYVDRF ELIPVTATFE   600
AEYDLEKAQK                                                         610

SEQ ID NO: 24               moltype = AA  length = 607
FEATURE                     Location/Qualifiers
REGION                      1..607
                            note = Bt29-Bt22Tr5
source                      1..607
                            mol_type = protein
                            organism = synthetic construct
SEQUENCE: 24
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVKGP   480
GFTGGDILRR TSGGPFAFSN VNLDWNLSQR YRARIRYAST TNLRMYVTIA GERIFAGQFN   540
KTMNTGDPLT FQSFSYATID TAFTFPTKAS SLTVGADTFS SGNEVYVDRF ELIPVTATFE   600
AEYDLEK                                                            607

SEQ ID NO: 25               moltype = AA  length = 603
FEATURE                     Location/Qualifiers
REGION                      1..603
                            note = Bt29-Bt22Tr6
source                      1..603
                            mol_type = protein
                            organism = synthetic construct
SEQUENCE: 25
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVKGP   480
GFTGGDILRR TSGGPFAFSN VNLDWNLSQR YRARIRYAST TNLRMYVTIA GERIFAGQFN   540
KTMNTGDPLT FQSFSYATID TAFTFPTKAS SLTVGADTFS SGNEVYVDRF ELIPVTATFE   600
AEY                                                                603

SEQ ID NO: 26               moltype = AA  length = 676
FEATURE                     Location/Qualifiers
```

```
REGION                     1..676
                           note = BT29BT22-TL22v1
source                     1..676
                           mol_type = protein
                           organism = synthetic construct
SEQUENCE: 26
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVKGP   480
GFTGGDILRR TSGGPPAFSN VNLDWNLSQR YRARIRYAST TNLRMYVTIA GERIFAGQFN   540
KTMNTGDPLT FQSFSYATID TAFTFPTKAS SLTVGADTFS SGNEVYVDRF ELIPVTATLE   600
AVTDLERAQK AVHELFTSTN PGGLKTDVAK DHYTNTISKS VQSVFRCRCS ERTRIYRWGY   660
PSKKEYWYIW GYTSKY                                                  676

SEQ ID NO: 27              moltype = AA   length = 644
FEATURE                    Location/Qualifiers
REGION                     1..644
                           note = BT29BT22-TL22v2
source                     1..644
                           mol_type = protein
                           organism = synthetic construct
SEQUENCE: 27
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVKGP   480
GFTGGDILRR TSGGPPAFSN VNLDWNLSQR YRARIRYAST TNLRMYVTIA GERIFAGQFN   540
KTMNTGDPLT FQSFSYATID TAFTFPTKAS SLTVGADTFS SGNEVYVDRF ELIPVTATLE   600
AVTDLERAQK AVHELFTSTN PGGLKTDVAK DHYTNTISKS VQSV                   644

SEQ ID NO: 28              moltype = AA   length = 634
FEATURE                    Location/Qualifiers
REGION                     1..634
                           note = BT29BT22-TL22v3
source                     1..634
                           mol_type = protein
                           organism = synthetic construct
SEQUENCE: 28
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVKGP   480
GFTGGDILRR TSGGPPAFSN VNLDWNLSQR YRARIRYAST TNLRMYVTIA GERIFAGQFN   540
KTMNTGDPLT FQSFSYATID TAFTFPTKAS SLTVGADTFS SGNEVYVDRF ELIPVTATLE   600
AVTDLERAQK AVHELFTSTN PGGLKTDVAK DHYT                              634

SEQ ID NO: 29              moltype = AA   length = 622
FEATURE                    Location/Qualifiers
REGION                     1..622
                           note = BT29BT22-TL22v4
source                     1..622
                           mol_type = protein
                           organism = synthetic construct
SEQUENCE: 29
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVKGP   480
GFTGGDILRR TSGGPPAFSN VNLDWNLSQR YRARIRYAST TNLRMYVTIA GERIFAGQFN   540
KTMNTGDPLT FQSFSYATID TAFTFPTKAS SLTVGADTFS SGNEVYVDRF ELIPVTATLE   600
AVTDLERAQK AVHELFTSTN PG                                           622
```

```
SEQ ID NO: 30            moltype = AA  length = 610
FEATURE                  Location/Qualifiers
REGION                   1..610
                         note = BT29BT22-TL22v5
source                   1..610
                         mol_type = protein
                         organism = synthetic construct
SEQUENCE: 30
MEINNQNQCV PYNCLNNPES EILNVAIFSS EQVAEIHLKI TRLILENFLP GGSFAFGLFD   60
LIWGIFNEDQ WSAFLRQVEE LINQRITEFA RGQAIQRLVG FGRSYDEYIL ALKEWENDPD  120
NPASKERVRT RFRTTDDALL TGVPLMAIPG FELATLSVYA QSANLHLALL RDAVFFGERW  180
GLTQTNINDL YSRLKNSIRD YTNHCVRFYN IGLGNLNVIR PEYYRFQREL TISVLDLVAL  240
FPNYDIRTYP IPTKSQLTRE IYTDPIISPG AQAGYTLQDV LREPHLMDFL NRLIIYTGEY  300
RGIRHWAGHE VESSRTGMMT NIRFPLYGTA ATAEPTRFIT PSTFPGLNLF YRTLSAPIFR  360
DEPGANIIIR YRTSLVEGVG FIQPNNGEQL YRVRGTLDSL DQLPLEGESS LTEYSHRLCH  420
VRFAQSLRNA EPLDYARVPM FSWTHRSATP TNTIDPDVIT QIPLVKAHTL QSGTTVVKGP  480
GFTGGDILRR TSGGPPAFSN VNLDWNLSQR YRARIRYAST TNLRMYVTIA GERIFAGQFN  540
KTMNTGDPLT FQSFSYATID TAFTFPTKAS SLTVGADTFS SGNEVYVDRF ELIPVTATLE  600
AVTDLERAQK                                                         610

SEQ ID NO: 31            moltype = AA  length = 600
FEATURE                  Location/Qualifiers
REGION                   1..600
                         note = BT29BT22-TL22v6
source                   1..600
                         mol_type = protein
                         organism = synthetic construct
SEQUENCE: 31
MEINNQNQCV PYNCLNNPES EILNVAIFSS EQVAEIHLKI TRLILENFLP GGSFAFGLFD   60
LIWGIFNEDQ WSAFLRQVEE LINQRITEFA RGQAIQRLVG FGRSYDEYIL ALKEWENDPD  120
NPASKERVRT RFRTTDDALL TGVPLMAIPG FELATLSVYA QSANLHLALL RDAVFFGERW  180
GLTQTNINDL YSRLKNSIRD YTNHCVRFYN IGLGNLNVIR PEYYRFQREL TISVLDLVAL  240
FPNYDIRTYP IPTKSQLTRE IYTDPIISPG AQAGYTLQDV LREPHLMDFL NRLIIYTGEY  300
RGIRHWAGHE VESSRTGMMT NIRFPLYGTA ATAEPTRFIT PSTFPGLNLF YRTLSAPIFR  360
DEPGANIIIR YRTSLVEGVG FIQPNNGEQL YRVRGTLDSL DQLPLEGESS LTEYSHRLCH  420
VRFAQSLRNA EPLDYARVPM FSWTHRSATP TNTIDPDVIT QIPLVKAHTL QSGTTVVKGP  480
GFTGGDILRR TSGGPPAFSN VNLDWNLSQR YRARIRYAST TNLRMYVTIA GERIFAGQFN  540
KTMNTGDPLT FQSFSYATID TAFTFPTKAS SLTVGADTFS SGNEVYVDRF ELIPVTATLE  600

SEQ ID NO: 32            moltype = AA  length = 610
FEATURE                  Location/Qualifiers
REGION                   1..610
                         note = Bt29-1FaTr1
source                   1..610
                         mol_type = protein
                         organism = synthetic construct
SEQUENCE: 32
MEINNQNQCV PYNCLNNPES EILNVAIFSS EQVAEIHLKI TRLILENFLP GGSFAFGLFD   60
LIWGIFNEDQ WSAFLRQVEE LINQRITEFA RGQAIQRLVG FGRSYDEYIL ALKEWENDPD  120
NPASKERVRT RFRTTDDALL TGVPLMAIPG FELATLSVYA QSANLHLALL RDAVFFGERW  180
GLTQTNINDL YSRLKNSIRD YTNHCVRFYN IGLGNLNVIR PEYYRFQREL TISVLDLVAL  240
FPNYDIRTYP IPTKSQLTRE IYTDPIISPG AQAGYTLQDV LREPHLMDFL NRLIIYTGEY  300
RGIRHWAGHE VESSRTGMMT NIRFPLYGTA ATAEPTRFIT PSTFPGLNLF YRTLSAPIFR  360
DEPGANIIIR YRTSLVEGVG FIQPNNGEQL YRVRGTLDSL DQLPLEGESS LTEYSHRLCH  420
VRFAQSLRNA EPLDYARVPM FSWTHRSATP TNTIDPDVIT QIPLVKAHTL QSGTTVVRGP  480
GFTGGDILRR TSGGPPAYTI VNINGQLPQR YRARIRYAST TNLRIYVTVA GERIFAGQFN  540
KTMDTGDPLT FQSFSYATIN TAFTFPMSQS SFTVGADTFS SGNEVYIDRF ELIPVTATFE  600
AEYDLERAQK                                                         610

SEQ ID NO: 33            moltype = AA  length = 607
FEATURE                  Location/Qualifiers
REGION                   1..607
                         note = Bt29-1FaTr2
source                   1..607
                         mol_type = protein
                         organism = synthetic construct
SEQUENCE: 33
MEINNQNQCV PYNCLNNPES EILNVAIFSS EQVAEIHLKI TRLILENFLP GGSFAFGLFD   60
LIWGIFNEDQ WSAFLRQVEE LINQRITEFA RGQAIQRLVG FGRSYDEYIL ALKEWENDPD  120
NPASKERVRT RFRTTDDALL TGVPLMAIPG FELATLSVYA QSANLHLALL RDAVFFGERW  180
GLTQTNINDL YSRLKNSIRD YTNHCVRFYN IGLGNLNVIR PEYYRFQREL TISVLDLVAL  240
FPNYDIRTYP IPTKSQLTRE IYTDPIISPG AQAGYTLQDV LREPHLMDFL NRLIIYTGEY  300
RGIRHWAGHE VESSRTGMMT NIRFPLYGTA ATAEPTRFIT PSTFPGLNLF YRTLSAPIFR  360
DEPGANIIIR YRTSLVEGVG FIQPNNGEQL YRVRGTLDSL DQLPLEGESS LTEYSHRLCH  420
VRFAQSLRNA EPLDYARVPM FSWTHRSATP TNTIDPDVIT QIPLVKAHTL QSGTTVVRGP  480
GFTGGDILRR TSGGPPAYTI VNINGQLPQR YRARIRYAST TNLRIYVTVA GERIFAGQFN  540
KTMDTGDPLT FQSFSYATIN TAFTFPMSQS SFTVGADTFS SGNEVYIDRF ELIPVTATFE  600
AEYDLER                                                            607
```

-continued

```
SEQ ID NO: 34          moltype = AA  length = 603
FEATURE                Location/Qualifiers
REGION                 1..603
                       note = Bt29-1FaTr3
source                 1..603
                       mol_type = protein
                       organism = synthetic construct
SEQUENCE: 34
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVRGP   480
GFTGGDILRR TSGGPFAYTI VNINGQLPQR YRARIRYAST TNLRIYVTVA GERIFAGQFN   540
KTMDTGDPLT FQSFSYATIN TAFTFPMSQS SFTVGADTFS SGNEVYIDRF ELIPVTATFE   600
AEY                                                                603

SEQ ID NO: 35          moltype = AA  length = 600
FEATURE                Location/Qualifiers
REGION                 1..600
                       note = Bt29-1FaTr4
source                 1..600
                       mol_type = protein
                       organism = synthetic construct
SEQUENCE: 35
MEINNQNQCV PYNCLNNPES EILNVAIFSS EQVAEIHLKI TRLILENFLP GGSFAFGLFD    60
LIWGIFNEDQ WSAFLRQVEE LINQRITEFA RGQAIQRLVG FGRSYDEYIL ALKEWENDPD   120
NPASKERVRT RFRTTDDALL TGVPLMAIPG FELATLSVYA QSANLHLALL RDAVFFGERW   180
GLTQTNINDL YSRLKNSIRD YTNHCVRFYN IGLGNLNVIR PEYYRFQREL TISVLDLVAL   240
FPNYDIRTYP IPTKSQLTRE IYTDPIISPG AQAGYTLQDV LREPHLMDFL NRLIIYTGEY   300
RGIRHWAGHE VESSRTGMMT NIRFPLYGTA ATAEPTRFIT PSTFPGLNLF YRTLSAPIFR   360
DEPGANIIIR YRTSLVEGVG FIQPNNGEQL YRVRGTLDSL DQLPLEGESS LTEYSHRLCH   420
VRFAQSLRNA EPLDYARVPM FSWTHRSATP TNTIDPDVIT QIPLVKAHTL QSGTTVVRGP   480
GFTGGDILRR TSGGPFAYTI VNINGQLPQR YRARIRYAST TNLRIYVTVA GERIFAGQFN   540
KTMDTGDPLT FQSFSYATIN TAFTFPMSQS SFTVGADTFS SGNEVYIDRF ELIPVTATFE   600
```

What is claimed is:

1. A polynucleotide comprising a nucleotide sequence encoding a chimeric insecticidal protein comprising the amino acid sequence of SEQ ID NO: 3.

2. The polynucleotide according to claim 1, wherein the polynucleotide comprises a nucleotide sequence that comprises:
   (a) a nucleotide sequence of SEQ ID NO: 4, SEQ ID NO: 5, SEQ ID NO: 6, or SEQ ID NO: 7;
   or
   (b) a nucleotide sequence that differs from the nucleotide sequence of (a) due to the degeneracy of the genetic code.

3. A nucleic acid molecule comprising the polynucleotide according to claim 1 operably associated with a heterologous plant expressible promoter.

4. A vector comprising the nucleic acid molecule according to claim 3.

5. A transgenic cell comprising the polynucleotide according to claim 1, wherein the transgenic cell is a bacterial cell or a plant cell.

6. The transgenic plant cell according to claim 5, wherein the plant cell is:
   (a) a monocot cell selected from the group consisting of a barley cell, a maize cell, an oat cell, a rice cell, a sorghum cell, a sugarcane cell and a wheat cell; or
   (b) a dicot cell selected from the group consisting of a soybean cell, a sunflower cell, a tomato cell, a cole crop cell, a cotton cell, a sugar beet cell and a tobacco cell.

7. A transgenic plant comprising the transgenic plant cell according to claim 6, wherein the plant is:
   (a) a monocot plant selected from the group consisting of a barley plant, a maize plant, an oat plant, a rice plant, a sorghum plant, a sugarcane plant and a wheat plant; or
   (b) a dicot plant selected from the group consisting of a soybean plant, a sunflower plant, a tomato plant, a cole crop plant, a cotton plant, a sugar beet plant and a tobacco plant.

8. The transgenic plant according to claim 7, wherein the transgenic plant further comprises a nucleotide sequence encoding a second insect control agent.

9. A transgenic seed of the transgenic plant according to claim 7, wherein the seed comprises the polynucleotide.

10. A harvested product derived from the transgenic plant according to claim 7, wherein the harvested product comprises the polynucleotide.

11. A processed product derived from the harvested product according to claim 10, wherein the processed product is a flour, a meal, an oil, a starch, or a product derived from any of the foregoing, and wherein the processed product comprises the polynucleotide.

12. A method of producing a transgenic plant with increased resistance to a lepidopteran insect pest, the method comprising:
   (a) introducing into a plant by transforming a plant cell with the polynucleotide of claim 1; or crossing a first plant comprising the polynucleotide, with a second plant, wherein the chimeric insecticidal protein is expressed in the plant, thereby producing a transgenic plant with increased resistance to an insect pest; and optionally obtaining a progeny plant from the transgenic plant, wherein the progeny plant comprises the polynucleotide and has increased resistance to an insect pest; or (b) planting a seed comprising the polynucleotide and growing a transgenic plant from the seed, wherein the transgenic plant comprises the polynucleotide and produces the chimeric insecticidal protein.

13. A method of producing a seed, the method comprising:
   (a) providing a transgenic plant that comprises the polynucleotide according to claim 1; and
   (b) harvesting a seed from the transgenic plant of (a), wherein the harvested seed comprises the chimeric insecticidal protein.

14. A method of producing a hybrid plant seed, the method comprising:
   (a) crossing a first inbred plant, which is a transgenic plant comprising the polynucleotide according to claim 1 with a second inbred plant; and
   (b) allowing a hybrid seed to form.

15. A method of reducing the development of resistance to a Vip3A protein or a Cry1F protein in a population of a target lepidopteran insect pest, the method comprising delivering to the target population or an environment thereof a transgenic plant comprising:
   (i) the polynucleotide according to claim 8; and
   (ii) a polynucleotide comprising a nucleotide sequence encoding a Vip3A protein or a nucleotide sequence encoding a Cry1F protein;
wherein the chimeric insecticidal protein and the Vip3A protein or the Cry1F protein are produced in the transgenic plant.

16. The polynucleotide according to claim 1, wherein the polynucleotide comprises a nucleotide sequence that comprises the nucleotide sequence of SEQ ID NO: 7.

17. A transgenic cell comprising the polynucleotide according to claim 16, wherein the transgenic cell is a plant cell.

18. A transgenic plant comprising the transgenic plant cell according to claim 17.

* * * * *